(12) United States Patent
Hunt et al.

(10) Patent No.: US 8,445,480 B2
(45) Date of Patent: *May 21, 2013

(54) CETP INHIBITORS DERIVED FROM BENZOXAZOLE ARYLAMIDES

(75) Inventors: Julianne A. Hunt, Montclair, NJ (US); Ramzi F. Sweis, Franklin Park, NJ (US); Dooseop Kim, Westfield, NJ (US); Florida Kallashi, Lawrence Harbor, NJ (US); Peter J. Sinclair, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 141 days.

This patent is subject to a terminal disclaimer.

(21) Appl. No.: 12/664,757

(22) PCT Filed: Jun. 16, 2008

(86) PCT No.: PCT/US2008/007467
§ 371 (c)(1),
(2), (4) Date: Aug. 12, 2010

(87) PCT Pub. No.: WO2008/156715
PCT Pub. Date: Dec. 24, 2008

(65) Prior Publication Data
US 2010/0298288 A1 Nov. 25, 2010

Related U.S. Application Data

(60) Provisional application No. 60/936,627, filed on Jun. 20, 2007.

(51) Int. Cl.
| | | |
|---|---|---|
| A61K 31/553 | (2006.01) | |
| A61K 31/5377 | (2006.01) | |
| A61K 31/506 | (2006.01) | |
| A61K 31/443 | (2006.01) | |
| A61K 31/4525 | (2006.01) | |
| A61K 31/423 | (2006.01) | |
| A61K 31/438 | (2006.01) | |
| C07D 239/42 | (2006.01) | |
| C07D 267/10 | (2006.01) | |
| C07D 413/14 | (2006.01) | |
| C07D 401/14 | (2006.01) | |
| C07D 221/20 | (2006.01) | |
| C07D 211/26 | (2006.01) | |
| C07D 263/57 | (2006.01) | |

(52) U.S. Cl.
USPC .......... 514/211.15; 514/233.8; 514/256; 514/273; 514/275; 514/278; 514/318; 514/321; 514/375; 540/544; 544/137; 544/328; 544/331; 546/16; 546/194; 546/198; 548/224

(58) Field of Classification Search .............. None
See application file for complete search history.

(56) References Cited

U.S. PATENT DOCUMENTS

| | | | |
|---|---|---|---|
| 4,831,152 A | 5/1989 | Itoh et al. | |
| 5,412,097 A | 5/1995 | Chakravarty et al. | |
| 5,874,431 A | 2/1999 | Stevens et al. | |
| 6,498,165 B1 | 12/2002 | Armstrong et al. | |
| 2003/0148387 A1 | 8/2003 | Chang et al. | |
| 2006/0040999 A1 | 2/2006 | Ali et al. | |

FOREIGN PATENT DOCUMENTS

| | | | |
|---|---|---|---|
| WO | 95/30659 | 11/1995 | |
| WO | WO 96/11917 | 4/1996 | |
| WO | WO 00/45819 | 8/2000 | |
| WO | WO 01/00587 | * 1/2001 | |
| WO | WO 01/14354 A1 | 3/2001 | |
| WO | 2004/019869 | 3/2004 | |
| WO | WO 2007/070173 A2 | 6/2007 | |
| WO | WO 2008/156717 A1 | 12/2008 | |
| WO | WO 2008/156718 A1 | 12/2008 | |

OTHER PUBLICATIONS

Supplementary European Search Report for EP 08 76 8488; Place of Search: Munich; performed by Lauro Paola; Completed on: Jun. 18, 2010

* cited by examiner

*Primary Examiner* — Rebecca Anderson
*Assistant Examiner* — Alicia L Otton
(74) *Attorney, Agent, or Firm* — James L. McGinnis; Catherine D. Fitch

(57) ABSTRACT

Compounds having the structure of Formula I1 including pharmaceutically acceptable salts of the compounds, are potent CETP (cholesterol ester transfer protein) inhibitors, and are useful for raising HDL-cholesterol, reducing LDL-cholesterol, and for treating or preventing atherosclerosis Atherosclerosis and its clinical consequences, coronary heart disease (CHD), stroke and penpheral vascular disease, represent a truly enormous burden to the health care systems of the industrialized world In formula I, A-B is an arylamide moiety.

14 Claims, No Drawings

US 8,445,480 B2

CETP INHIBITORS DERIVED FROM BENZOXAZOLE ARYLAMIDES

CROSS REFERENCE TO RELATED APPLICATIONS

This application is a U.S. National Phase application under 35 U.S.C. §371 of PCT Application No. PCT/US2008/007467, filed Jun. 16, 2008, which claims priority under 35U.S.C. §119(e) from U.S. Application No. 60/936,627, filed Jun. 20, 2007.

FIELD OF THE INVENTION

This invention relates to a class of chemical compounds that inhibit cholesterol ester transfer protein (CETP) and therefore have utility in raising HDL-cholesterol, lowering LDL-cholesterol, and in the treatment and prevention of atherosclerosis.

BACKGROUND OF THE INVENTION

Atherosclerosis and its clinical consequences, coronary heart disease (CHD), stroke and peripheral vascular disease, represent a truly enormous burden to the health care systems of the industrialized world. In the United States alone, approximately 13 million patients have been diagnosed with CHD, and greater than one half million deaths are attributed to CHD each year. Further, this toll is expected to grow over the next quarter century as an epidemic in obesity and diabetes continues to grow.

It has long been recognized that in mammals, variations in circulating lipoprotein profiles correlate with the risk of atherosclerosis and CHD. The clinical success of HMG-CoA Reductase inhibitors, especially the statins, in reducing coronary events is based on the reduction of circulating Low Density Lipoprotein cholesterol (LDL-C), levels of which correlate directly with increased risk for atherosclerosis. More recently, epidemiologic studies have demonstrated an inverse relationship between High Density Lipoprotein cholesterol (HDL-C) levels and atherosclerosis, leading to the conclusion that low serum HDL-C levels are associated with an increased risk for CHD.

Metabolic control of lipoprotein levels is a complex and dynamic process involving many factors. One important metabolic control in man is the cholesteryl ester transfer protein (CETP), a plasma glycoprotein that catalyzes the movement of cholesteryl esters from HDL to the apoB containing lipoproteins, especially VLDL (see Hesler, C. B., et. al. (1987) *Purification and characterization of human plasma cholesteryl ester transfer protein. J. Biol. Chem.* 262(5), 2275-2282)). Under physiological conditions, the net reaction is a heteroexchange in which CETP carries triglyceride to HDL from the apoB lipoproteins and transports cholesterol ester from HDL to the apoBliprotein.

In humans, CETP plays a role in reverse cholesterol transport, the process whereby cholesterol is returned to the liver from peripheral tissues. Intriguingly, many animals do not possess CETP, including animals that have high HDL levels and are known to be resistant to coronary heart disease, such as rodents (see Guyard-Dangremont, V., et. al., (1998) *Phospholipid and cholesteryl ester transfer activities in plasma from 14 vertebrate species. Relation to atherogenesis susceptibility, Comp. Biochem. Physiol. B Biochem. Mol. Biol.* 120 (3), 517-525). Numerous epidemiologic studies correlating the effects of natural variation in CETP activity with respect to coronary heart disease risk have been performed, including studies on a small number of known human null mutations (see Hirano, K.-I., Yamashita, S, and Matsuzawa, Y. (2000) *Pros and cons of inhibiting cholesteryl ester transfer protein, Curr. Opin. Lipidol.* 11(6), 589-596). These studies have clearly demonstrated an inverse correlation between plasma HDL-C concentration and CETP activity (see Inazu, A., et. al. (2000) *Cholesteryl ester transfer protein and atherosclerosis, Curr. Opin. Lipidol.* 11(4), 389-396), leading to the hypothesis that pharmacologic inhibition of CETP lipid transfer activity may be beneficial to humans by increasing levels of HDL-C while lowering those of LDL.

Despite the significant therapeutic advance that statins such as simvastatin (ZOCOR®) represent, statins only achieve a risk reduction of approximately one-third in the treatment and prevention of atherosclerosis and ensuing atherosclerotic disease events. Currently, few pharmacologic therapies are available that favorably raise circulating levels of HDL-C. Certain statins and some fibrates offer modest HDL-C gains. Niacin, which provides the most effective therapy for raising HDL-C that has been clinically documented, suffers from patient compliance issues, due in part to side effects such as flushing. An agent that safely and effectively raises HDL cholesterol levels can answer a significant, but as yet unmet medical need by offering a means of pharmacologic therapy that can significantly improve circulating lipid profiles through a mechanism that is complementary to existing therapies.

New classes of chemical compounds that inhibit CETP are being investigated at several pharmaceutical companies or are in clinical trials. No CETP inhibitors are currently being marketed. Clinical trials of Pfizer's CETP inhibitor torcetrapib were recently terminated because of increased mortality in patients who were using the drug during outcomes studies. New compounds are needed so that one or more pharmaceutical compounds can be found that are safe and effective. The novel compounds described herein are very potent CETP inhibitors. The compounds are amide derivatives of 2-arylbenzoxazoles and related compounds. A different family of CETP inhibitors based on 2-arylbenzoxazoles is disclosed in WO 2007/070173.

SUMMARY OF THE INVENTION

Compounds having Formula I, including pharmaceutically acceptable salts of the compounds, are CETP inhibitors, and have utility in raising HDL-cholesterol, lowering LDL-cholesterol, and in treating, preventing, and/or reducing the risk of developing atherosclerosis:

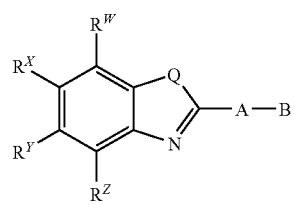

I

In the compounds of Formula I,

Q is selected from the group consisting of O, S, and —N($R^2$)—;

A is a difunctional cyclic group selected from 1,4-phenylene, 2,5-pyridinylene, and 2,5-pyrimidinylene, wherein A is optionally substituted with 1-3 substituent groups $R^1$;

Each $R^1$ is independently selected from the group consisting of halogen, $C_1$-$C_3$alkyl, $C_2$-$C_3$alkenyl, $C_2$-$C_3$alkynyl, and —$OC_1$-$C_3$alkyl, wherein each alkyl, alkenyl, and alkynyl substituent is optionally substituted with 1-5 halogens;

Each $R^2$ is independently selected from the group consisting of H, $C_1$-$C_3$alkyl, $C_2$-$C_3$alkenyl, and $C_2$-$C_3$alkynyl, wherein each alkyl, alkenyl, and alkynyl substituent is optionally substituted with 1-5 halogens;

$R^W$ is selected from the group consisting of (a) $C_1$-$C_5$alkyl which is optionally substituted with 1-5 halogens, (b) $C_{2-5}$ alkenyl which is optionally substituted with 1-5 halogens; (c) —$OC_1$-$C_5$ alkyl which is optionally substituted with 1-5 halogens, (d) —$SC_1$-$C_5$ alkyl which is optionally substituted with 1-5 halogens, (e) —$OC_{2-5}$ alkenyl which is optionally substituted with 1-5 halogens, (f) $C_3$-$C_6$cycloalkyl, (g) phenyl, (h) a 5-6 membered saturated or partly unsaturated heterocyclic group having 1-3 heteroatoms independently selected from N, S and O, (i) a 5-7 membered heteroaromatic group having 1-3 heteroatoms independently selected from N, S, and O, (j) —C(=O)$OC_{1-3}$alkyl which is optionally substituted with 1-5 halogens, and (k) —C(=O)OH, wherein said $C_3$-$C_6$cycloalkyl, phenyl, 5-6 membered saturated or partly unsaturated heterocyclic group, and 5-7 membered heteroaromatic group are optionally substituted with 1-3 substituents independently selected from halogen, $CH_3$, $CF_3$, —$OCH_3$, and —$OCF_3$;

$R^Y$ is selected from the group consisting of halogen, $CH_3$, $CF_3$, —$OCH_3$, —$OCF_3$, —CN, phenyl, and a 6-membered heteroaromatic group having 1-2 N, wherein phenyl and the 6-membered heteroaromatic group are optionally substituted with 1-3 substituents independently selected from halogen, $CH_3$, $CF_3$, —$OCH_3$, and —$OCF_3$;

$R^X$ and $R^Z$ are each selected from the group consisting of H, halogen, $CH_3$, $CF_3$, —$OCH_3$, and —$OCF_3$;

B is selected from the group consisting of:
(a) —C(=O)N($R^3$)($CR^4R^5$)$_x$($CR^6R^7$)$_y$$D^2$,
(b) —C(=O)N($R^3$)($CR^4R^5$)$_p$($CR^6R^7$)$_q$$D^3$, and
(c) —C(=O)$D^3$;

$R^3$ is selected from the group consisting of H and $C_1$-$C_3$alkyl;

$R^4$ is selected from the group consisting of H, $C_1$-$C_3$alkyl, $CF_3$, —C(=O)OH, and —C(=O)$OC_1$-$C_3$alkyl;

$R^5$ is selected from the group consisting of H, $C_1$-$C_3$alkyl, and $CF_3$;

$R^6$ is selected from the group consisting of H, $C_1$-$C_3$alkyl, $CF_3$, —C(=O)OH, and —C(=O)$OC_1$-$C_3$alkyl;

$R^7$ is selected from the group consisting of H, $C_1$-$C_3$alkyl, $CF_3$, and phenyl, which is optionally substituted with 1-3 groups independently selected from halogen, $CH_3$, $CF_3$, —$OCH_3$, and —$OCF_3$;

x is 0 or 1;
y is 0, 1, or 2;
p is 0 or 1;
q is 0, 1, or 2, with the proviso that p and q are not both 0;

$D^2$ is a cyclic group selected from (a) 4-membered and 6-8 membered saturated and partly unsaturated heterocyclic groups, and (b) a spirocyclic group having two rings joined by a spirocyclic linkage through a carbon atom wherein each ring is a 5-7-membered ring, wherein $D^2$ comprises one ring member —N($R^8$)—, optionally 1-2 ring members independently selected from —O— and —S—, optionally one carbonyl group, and optionally 1-2 double bonds, wherein $D^2$ or a ring of $D^2$ is optionally fused to a phenyl ring or to a $C_5$-$C_7$Cycloalkyl, wherein $D^2$ is connected to the remainder of the structure represented by Formula I through a carbon atom of $D^2$, wherein $D^2$ is optionally substituted with 1-3 substituents independently selected from halogen, —CN, —$NO_2$, —N($R^3$)$_2$—, $C_1$-$C_3$alkyl, $CF_3$, —$OCH_3$, phenyl, pyridyl, and —$OCF_3$, and optionally with 1 group $C_1$-$C_5$alkylene-phenyl, wherein phenyl and pyridyl in all uses are optionally substituted with 1-3 substituent groups independently selected from halogen, $CH_3$, $CF_3$, —$OCH_3$, and —$OCF_3$;

$D^3$ is a heterocyclic group selected from (a) a saturated or partly unsaturated 4-8 membered monocyclic heterocyclic group, (b) a saturated or partly unsaturated bicyclic heterocyclic group wherein each ring is a 5-8-membered ring, and (c) a spirocyclic group having two rings joined by a spirocyclic linkage through a carbon atom wherein each ring is a 5-7-membered ring, wherein $D^3$ comprises one N atom which is connected to the remainder of the structure represented by Formula I, and $D^3$ optionally comprises (a) 1-2 heteroatoms independently selected from O and S, (b) optionally one group —N($R^8$)—, (c) optionally 1-2 double bonds, and (d) optionally one carbonyl group, wherein $D^3$ or a ring of $D^3$ is optionally fused to a phenyl group, and $D^3$ is optionally substituted with 1-3 substituents independently selected from halogen, —CN, —$NO_2$, —N($R^3$)$_2$—, $C_1$-$C_3$alkyl, $CF_3$, —$OCH_3$, phenyl, pyridyl, and —$OCF_3$, and optionally with 1 group $C_1$-$C_5$alkylene-phenyl, wherein phenyl and pyridyl in all uses are optionally substituted with 1-3 substituent groups independently selected from halogen, $CH_3$, $CF_3$, —$OCH_3$, and —$OCF_3$;

$R^8$ is selected from the group consisting of $C_1$-$C_9$alkyl, —C(=O)$OC_1$-$C_9$alkyl, —C(=O)$C_1$-$C_9$alkyl, —S(O)$_x$$C_1$-$C_9$alkyl, —C(=O)N($R^9$)$_2$, —$C_1$-$C_3$alkylene-C(=O)$OC_1$-$C_6$alkyl, —$C_1$-$C_5$alkylene-$OC_1$-$C_9$alkyl, and a cyclic group $D^4$ bonded to the N to which $R^8$ is connected or to a difunctional linking group $L^4$ which is bonded to the N to which $R^8$ is connected, wherein the $C_1$-$C_9$alkyl and $C_1$-$C_6$alkyl groups in all uses are optionally substituted with 1-9 halogens;

Wherein $D^4$ is selected from the group consisting of (a) phenyl, (b) naphthyl, (c) $C_3$-$C_8$cycloalkyl optionally having 1-2 double bonds, (d) a saturated or partially unsaturated monocyclic or bicyclic 4-10 membered heterocycle having 1-3 heteroatoms independently selected from N, O, and S and optionally one —C(=O)— group, said heterocycle optionally having 1-2 double bonds, and (e) a monocyclic or bicyclic 5-12 membered heteroaromatic group having 1-3 heteroatoms independently selected from N, S, and O and optionally having one —C(=O)—group;

$L^4$ is selected from the group consisting of —C(=O)—, —C(=O)O—, —S(O)$_2$—, —C(=O)N($R^3$)—, —S(O)$_2$N($R^3$)—, —$C_1$-$C_7$alkylene-, —C(=O)$C_1$-$C_7$alkylene-, —C(=O)$C_1$-$C_7$alkyleneN($R^3$)—, —C(=O)$OC_1$-$C_7$alkylene-, —S(O)$_2$$C_1$-$C_7$alkylene-, —C(=O)N($R^3$)$C_1$-$C_7$alkylene-, —S(O)$_2$N($R^3$)$C_1$-$C_7$alkylene-, —$C_1$-$C_7$alkyleneN($R^3$)S(O)$_2$—, —$C_1$-$C_7$alkyleneS(O)$_2$N($R^3$)—, —$C_1$-$C_7$alkyleneN($R^3$)C(=O)—, and —$C_1$-$C_7$alkyleneC(=O)N($R^3$)—, wherein —$C_1$-$C_7$alkylene- optionally comprises a double bond between two adjacent carbons and optionally comprises a difunctional group selected from O, S, —S(O)$_2$—, —N$R^3$—, —C(=O)—, —N($R^3$)C(=O)—, and —N($R^3$)S(O)$_2$— between two adjacent carbons, wherein $D^4$ is optionally substituted with 1-3 substituents independently selected from halogen, —CN, —$NO_2$, —OH, $C_1$-$C_7$alkyl, $C_2$-$C_7$alkenyl, $CF_3$, —$OC_1$-$C_5$alkyl, —$C_1$-$C_5$alkylene-$OC_1$-$C_5$alkyl, —$OCF_3$, —N($R^3$)$_2$—, —C(=O)OH, and —C(=O)$OC_1$-$C_7$alkyl, and is optionally substituted with one cyclic group $D^6$ bonded directly to $D^4$ or connected to $D^4$ through a linking group $L^6$, wherein $D^6$ has the same selections as $D^4$, $L^6$ has the same selections as $L^4$, and D6 is optionally substituted with 1-3 substituents independently selected from halogen, —CN, —$NO_2$, —OH, $C_1$-$C_7$alkyl, $C_2$-$C_7$alkenyl, $CF_3$, —OC$_1$-C$_5$alkyl, —C$_1$-C$_5$alkylene-OC$_1$-C$_5$alkyl, —OCF$_3$, —N(R$^3$)$_2$—, —C(=O)OH, and —C(=O)OC$_1$-C$_7$alkyl, wherein the C$_1$-C$_7$alkyl, C$_2$-C$_7$alkenyl, and —OC$_1$-C$_5$alkyl groups in all uses in substituents on D4 and D6 are optionally substituted with 1-5 halogens; and Each R$^9$ is independently selected from the group consisting of H, C$_1$-C$_7$alkyl, C$_2$-C$_7$alkenyl, and C$_2$-C$_7$alkynyl, wherein said C$_1$-C$_7$alkyl, C$_2$-C$_7$alkenyl, and C$_2$-C$_7$alkynyl are optionally substituted with 1-9 halogens.

In the compounds of formula I and in compounds described subsequently, alkyl, alkenyl and alkynyl groups can be linear or branched, unless otherwise stated.

DETAILED DESCRIPTION OF THE INVENTION

In embodiments of the invention Q is O.

In embodiments of the invention, A is a difunctional cyclic group selected from 1,4-phenylene, 2,5-pyridinylene, and 2,5-pyrimidinylene, wherein A is optionally substituted with 1-3 substituent groups R$^1$.

In embodiments of the invention, each R$^1$ is independently selected from the group consisting of halogen, CH$_3$, CF$_3$, —OCH$_3$, and —OCF$_3$.

In embodiments of the invention, R$^W$ is selected from the group consisting of (a) C$_1$-C$_5$alkyl which is optionally substituted with 1-5 F, (b) C$_{2-3}$ alkenyl which is optionally substituted with 1-3 F, (c) —OC$_1$-C$_3$alkyl which is optionally substituted with 1-3 F, (d) —SC$_1$-C$_3$alkyl which is optionally substituted with 1-3 F, (e) —OC$_{2-3}$ alkenyl which is optionally substituted with 1-3 F, (f) C$_3$-C$_6$cycloalkyl, (g) phenyl, (h) pyridyl, (i) —C(=O)OC$_{1-3}$alkyl which is optionally substituted with 1-3 F, and (k) —C(=O)OH, wherein said C$_3$-C$_6$cycloalkyl, phenyl, and pyridinyl substituents are optionally substituted with 1-3 substituents independently selected from halogen, CH$_3$, CF$_3$, —OCH$_3$, and —OCF$_3$.

In embodiments of the invention, R$^Y$ is selected from the group consisting of halogen, CH$_3$, CF$_3$, —OCH$_3$, —OCF$_3$, and —CN.

In embodiments of the invention, R$^X$ and R$^Z$ are each selected from the group consisting of H, halogen, CH$_3$, CF$_3$, —OCH$_3$, and —OCF$_3$.

In embodiments of the invention, the compounds are described by Formula Ia, including pharmaceutically acceptable salts thereof:

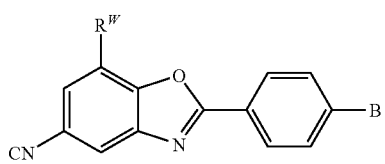

Ia

In embodiments of Formula I and Ia, R$^W$ is selected from the group consisting of C$_1$-C$_4$alkyl which is optionally substituted with 1-3 F, C$_{2-3}$ alkenyl, —OCH$_3$, —OCF$_3$, —SCH$_3$, —SCF$_3$, cyclopropyl, —C(=O)OC$_{1-3}$alkyl, and phenyl which is optionally substituted with 1-3 substituents independently selected from halogen, CH$_3$, CF$_3$, —OCH$_3$, and —OCF$_3$.

In embodiments of Formula I and Ia, R$^3$ is selected from the group consisting of H and CH$_3$.

In embodiments of Formula I and Ia, R$^4$ is selected from the group consisting of H, CH$_3$, —C(=O)OH, and —C(=O)OCH$_3$; and R$^5$ is H.

In embodiments of Formula I and Ia, R$^6$ is H; and R$^7$ is selected from the group consisting of H and phenyl, which is optionally substituted with 1-3 groups independently selected from halogen, CH$_3$, CF$_3$, —OCH$_3$, and —OCF$_3$.

In embodiments of Formula I and Ia, x is 0 or 1; and y is 0.

In embodiments of Formula I and Ia, p is 1; and q is 0 or 1.

In embodiments of formula I and Ia, R$^W$ is isopropyl.

In embodiments of the compounds described above, D$^2$ is selected from the group consisting of azetidine, piperidine, morpholine, a saturated 7-membered heterocyclic ring which comprises one —O— and one —N— in the ring, and a spirocyclic group comprising a cyclopentane ring and a piperidine ring joined by a spirocyclic linkage through a commonly shared carbon atom, wherein D$^2$ is connected to the right hand side of the structure of Formula Ia through a carbon atom of D$^2$, wherein said carbon atom of D$^2$ that is connected to the right hand side of Formula Ia is optionally substituted with one group selected from phenyl, pyridyl, and C$_1$-C$_3$alkyl optionally substituted with 1-3 F, wherein the phenyl and pyridyl groups are optionally substituted with one group selected from CH$_3$, CF$_3$, —OCH$_3$, —OCF$_3$, and halogen, and D$^2$ is optionally also substituted on another carbon atom of the ring with one substitutent selected from CH$_3$, CF$_3$, —OCH$_3$, —OCF$_3$ and halogen, and the nitrogen atom in the ring of D$^2$ is attached to the group R$^8$.

In embodiments of the compounds described above, D$^3$ is selected from the group consisting of (a) a 5-7-membered saturated cyclic amine; (b) a 6-7 membered saturated cyclic diamine; (c) a 5-6 membered saturated cyclic amine connected by a spirocyclic linkage through a shared carbon atom to a 5-6 membered cyclic ether, a 5-6 membered cycloalkyl, or a second 5-6 membered saturated cyclic amine, wherein one N atom of D$^3$ is connected to the right hand side of the structure of Formula Ia, and the second N atom of D$^3$, if present, is connected to the group R$^8$, wherein D$^3$ is optionally substituted with one substitutent group selected from CH$_3$, CF$_3$, —OCH$_3$, —OCF$_3$, halogen, phenyl, and —(CH$_2$)$_{1-3}$phenyl, wherein phenyl and the phenyl group of (CH$_2$)$_{1-3}$phenyl are optionally substituted with one group selected from F, Cl, CH$_3$, CF$_3$, —OCH$_3$ and —OCF$_3$.

In embodiments of the compounds described above, R$^8$ is selected from the group consisting of C$_1$-C$_8$alkyl, optionally substituted with 1-7 F, —C(=O)C$_1$-C$_8$alkyl, —C(=O)OC$_1$-C$_5$alkyl, and a cyclic group D$^4$ which is bonded directly to the N to which R$^8$ is connected or is bonded to a difunctional linking group L$^4$ which is bonded to the N to which R$^8$ is connected.

In embodiments of the compounds described above, D$^4$ is selected from the group consisting of pyrimidinyl, pyridyl, phenyl, C$_3$-C$_6$cycloalkyl, naphthyl, and quinolyl, and is optionally substituted with 1-3 groups independently selected from halogen, C$_1$-C$_4$alkyl, C$_2$-C$_5$alkenyl, CF$_3$, —OC$_1$-C$_4$alkyl, —OCF$_3$, —CO$_2$H, —CO$_2$C$_1$-C$_3$alkyl, —N(CH$_3$)$_2$, —NO$_2$, —CN, and optionally one cyclic group D$^6$ which is bonded directly to D$^4$ or is bonded to a difunctional linking group L$^6$ which is bonded to D$^4$.

In embodiments of the compounds described above, L$^4$ is selected from the group consisting of —(CH$_2$)$_{1-3}$—, —C(=O)—, —C(=O)(CH$_2$)$_{1-3}$—, —C(=O)CH(C$_2$H$_5$)—, —C(=O)CH=CH—, —C(=O)OCH$_2$—, —C(=O)NHCH$_2$—, —C(=O)(CH$_2$)$_{1-2}$NH—, —CH$_2$C(=O)—, —SO$_2$—, and —S(O)$_2$(CH$_2$)$_3$—.

In embodiments of the compounds described above, D$^6$ is selected from the group consisting of piperidinyl, phenyl, cyclopropyl, cyclohexyl, cyclohexenyl, and pyrazolyl, and is optionally substituted with 1-3 substituents independently selected from $C_1$-$C_4$alkyl optionally substituted with 1-3 F, —$OC_1$-$C_4$alkyl optionally substituted with 1-3 F, halogen, and optionally one phenoxy;

and $L^6$ is optionally $C_2$-$C_3$alkenylene.

DEFINITIONS

"Ac" is acetyl, which is $CH_3C(=O)$—.

"Alkyl" means saturated carbon chains which may be linear or branched or combinations thereof, unless the carbon chain is defined otherwise. Other groups having the prefix "alk", such as alkoxy and alkanoyl, also may be linear or branched or combinations thereof, unless the carbon chain is defined otherwise. Examples of alkyl groups include methyl, ethyl, propyl, isopropyl, butyl, sec- and tert-butyl, pentyl, hexyl, heptyl, octyl, nonyl, and the like.

"Alkylene" groups are alkyl groups that are difunctional rather than monofunctional. For example, methyl is an alkyl group and methylene (—$CH_2$—) is the corresponding alkylene group.

"Alkenyl" means carbon chains which contain at least one carbon-carbon double bond, and which may be linear or branched or combinations thereof. Examples of alkenyl include vinyl, allyl, isopropenyl, pentenyl, hexenyl, heptenyl, 1-propenyl, 2-butenyl, 2-methyl-2-butenyl, and the like.

"Alkynyl" means carbon chains which contain at least one carbon-carbon triple bond, and which may be linear or branched or combinations thereof. Examples of alkynyl include ethynyl, propargyl, 3-methyl-1-pentynyl, 2-heptynyl and the like.

"Cycloalkyl" means a saturated carbocyclic ring having from 3 to 8 carbon atoms, unless otherwise stated (e.g., cycloalkyl may be defined as having one or more double bonds). The term also includes a cycloalkyl ring fused to an aryl group. Examples of cycloalkyl include cyclopropyl, cyclopentyl, cyclohexyl, cycloheptyl, and the like. "Cycloalkenyl" means a non-aromatic carbocyclic ring having one or more double binds.

"Aryl" (and "arylene") when used to describe a substituent or group in a structure means a monocyclic or bicyclic compound in which the rings are aromatic and which contains only carbon ring atoms. The term "aryl" can also refer to an aryl group that is fused to a cycloalkyl or heterocycle. Preferred "aryls" are phenyl and naphthyl. Phenyl is generally the most preferred aryl group.

"EDC" is 1-ethyl-3-(3-dimethylaminopropyl)carbodiimide.

"Heterocyclyl," "heterocycle," and "heterocyclic" means a fully or partially saturated or aromatic 5-6 membered ring containing 1-4 heteroatoms independently selected from N, S and O, unless otherwise stated.

"Benzoheterocycle" represents a phenyl ring fused to a 5-6-membered heterocyclic ring having 1-2 heteroatoms, each of which is O, N, or S, where the heterocyclic ring may be saturated or unsaturated. Examples include indole, benzofuran, 2,3-dihydrobenzofuran and quinoline.

"DIPEA" is diisopropylethylamine.

"Halogen" includes fluorine, chlorine, bromine and iodine.

"HOBT" is 1-Hydroxybenzotriazole.

"IPAC" is isopropyl acetate.

"Me" represents methyl.

"Weinreb amine" is N,O-dimethylhydroxylamine.

The term "composition," as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention and a pharmaceutically acceptable carrier.

The substituent "tetrazole" means a 2H-tetrazol-5-yl substituent group and tautomers thereof.

Optical Isomers-Diastereomers-Geometric Isomers-Tautomers

Compounds of Formula I may contain one or more asymmetric centers and can thus occur as racemates, racemic mixtures, single enantiomers, diastereomeric mixtures and individual diastereomers. The present invention is meant to include all such stereoisomeric forms of the compounds of Formula I and all mixtures of the compounds. When structures are shown without a stereochemical representation, all stereochemical structures are included individually and collectively, such as enantiomers, diastereomers (where diastereomers are possible), and mixtures of the enantiomers and/or diastereomers, including racemic mixtures. When a stereochemical structure of a compound is provided, any reference to stereoisomers of the compound includes other enantiomers, diastereomers (when possible), and mixtures of these, including racemic mixtures.

Some of the compounds described herein may contain olefinic double bonds, and unless specified otherwise, are meant to include both E and Z geometric isomers.

Some of the compounds described herein may exist as tautomers. An example is a ketone and its enol form, known as keto-enol tautomers. The individual tautomers as well as mixtures thereof are encompassed with compounds of Formula I.

Compounds of Formula I having one or more asymmetric centers may be separated into diastereoisomers, enantiomers, and the like by methods well known in the art.

Alternatively, enantiomers and other compounds with chiral centers may be synthesized by stereospecific synthesis using optically pure starting materials and/or reagents of known configuration.

Some of the biphenyl and biaryl compounds herein are observed as mixtures of atropisomers (rotamers) in the NMR spectra. The individual atropisomers as well as mixtures thereof are encompassed with the compounds of this invention.

Salts

The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, as used herein, references to the compounds of Formula I are meant to also include the pharmaceutically acceptable salts.

Metabolites—Prodrugs

Therapeutically active metabolites, where the metabolites themselves fall within the scope of the claimed invention, are also compounds of the current invention. Prodrugs, which are compounds that are converted to the claimed compounds as they are being administered to a patient or after they have been administered to a patient, are also compounds of this invention.

Utilities

Compounds of the current invention are potent inhibitors of CETP. They are therefore useful in treating diseases and conditions that are treated by inhibitors of CETP.

One aspect of the present invention provides a method for treating or reducing the risk of developing a disease or condition that may be treated or prevented by inhibition of CETP by administering a therapeutically effective amount of a compound of this invention to a patient in need of treatment. A patient is a human or mammal, and is most often a human. A "therapeutically effective amount" is the amount of compound that is effective in obtaining a desired clinical outcome in the treatment of a specific disease.

Diseases or conditions that may be treated with compounds of this invention, or which the patient may have a reduced risk of developing as a result of being treated with the compounds of this invention, include: atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity, endotoxemia, and metabolic syndrome.

The compounds of this invention are particularly effective in raising HDL-C and/or increasing the ratio of HDL-C to LDL-C. The compounds are also effective in lowering LDL-C. These changes in HDL-C and LDL-C may be beneficial in treating atherosclerosis, reducing or reversing the development of atherosclerosis, reducing the risk of developing atherosclerosis, or preventing atherosclerosis.

Administration and Dose Ranges

Any suitable route of administration may be employed for providing a mammal, especially a human, with an effective dose of a compound of the present invention. For example, oral, rectal, topical, parenteral, ocular, pulmonary, nasal, and the like may be employed. Dosage forms include tablets, troches, dispersions, suspensions, solutions, capsules, creams, ointments, aerosols, and the like. Preferably compounds of Formula I are administered orally.

The effective dosage of active ingredient employed may vary depending on the particular compound employed, the mode of administration, the condition being treated and the severity of the condition being treated. Such dosage may be ascertained readily by a person skilled in the art.

When treating the diseases for which compounds of Formula I are indicated, generally satisfactory results are obtained when the compounds of the present invention are administered at a daily dosage of from about 0.01 milligram to about 100 milligram per kilogram of animal or human body weight, preferably given as a single daily dose or in divided doses two to six times a day, or in sustained release form. In the case of a 70 kg adult human, the total daily dose will generally be from about 0.5 milligram to about 500 milligrams. For a particularly potent compound, the dosage for an adult human may be as low as 0.1 mg. The dosage regimen may be adjusted within this range or even outside of this range to provide the optimal therapeutic response.

Oral administration will usually be carried out using tablets. Examples of doses in tablets are 0.5 mg, 1 mg, 2 mg, 5 mg, 10 mg, 25 mg, 50 mg, 100 mg, 250 mg, and 500 mg. Other oral forms can also have the same dosages (e.g. capsules).

Pharmaceutical Compositions

Another aspect of the present invention provides pharmaceutical compositions which comprise a compound of Formula I and a pharmaceutically acceptable carrier. The pharmaceutical compositions of the present invention comprise a compound of Formula I or a pharmaceutically acceptable salt as an active ingredient, as well as a pharmaceutically acceptable carrier and optionally other therapeutic ingredients. The term "pharmaceutically acceptable salts" refers to salts prepared from pharmaceutically acceptable non-toxic bases or acids including inorganic bases or acids and organic bases or acids. A pharmaceutical composition may also comprise a prodrug, or a pharmaceutically acceptable salt thereof, if a prodrug is administered. Pharmaceutical compositions may also consist essentially of a compound of Formula I and a pharmaceutically acceptable carrier without other therapeutic ingredients.

The compositions include compositions suitable for oral, rectal, topical, parenteral (including subcutaneous, intramuscular, and intravenous), ocular (ophthalmic), pulmonary (nasal or buccal inhalation), or nasal administration, although the most suitable route in any given case will depend on the nature and severity of the conditions being treated and on the nature of the active ingredient. They may be conveniently presented in unit dosage form and prepared by any of the methods well-known in the art of pharmacy.

In practical use, the compounds of Formula I can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets, with the solid oral preparations being preferred over the liquid preparations.

Because of their ease of administration, tablets and capsules represent the most advantageous oral dosage unit form in which case solid pharmaceutical carriers are obviously employed. If desired, tablets may be coated by standard aqueous or nonaqueous techniques. Such compositions and preparations should contain at least 0.1 percent of active compound. The percentage of active compound in these compositions may, of course, be varied and may conveniently be between about 2 percent to about 60 percent of the weight of the unit. The amount of active compound in such therapeutically useful compositions is such that an effective dosage will be obtained. The active compounds can also be administered intranasally as, for example, liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Compounds of formula I may also be administered parenterally. Solutions or suspensions of these active compounds can be prepared in water suitably mixed with a surfactant such as hydroxypropylcellulose. Dispersions can also be prepared in glycerol, liquid polyethylene glycols and mixtures thereof in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g. glycerol, propylene glycol and liquid polyethylene glycol), suitable mixtures thereof, and vegetable oils.

Combination Therapy

Compounds of the invention (e.g. Formula I and Ia-Ij) may be used in combination with other drugs that may also be useful in the treatment or amelioration of the diseases or conditions for which compounds of Formula I are useful. Such other drugs may be administered, by a route and in an amount commonly used therefor, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy also includes therapies in which the compound of Formula I and one or more other drugs are administered on different schedules.

When oral formulations are used, the drugs may be combined into a single combination tablet or other oral dosage form, or the drugs may be packaged together as separate tablets or other oral dosage forms. It is also contemplated that when used in combination with one or more other active ingredients, the compound of the present invention and the other active ingredients may be used in lower doses than when each is used singly. Accordingly, the pharmaceutical compositions of the present invention include those that contain one or more other active ingredients, in addition to a compound of Formula I.

Examples of other active ingredients that may be administered in combination with a compound of this invention (e.g. Formula I), and either administered separately or in the same pharmaceutical composition, include, but are not limited to, other compounds which improve a patient's lipid profile, such as (i) HMG-CoA reductase inhibitors, (which are generally statins, including lovastatin, simvastatin, rosuvastatin, pravastatin, fluvastatin, atorvastatin, rivastatin, itavastatin, pitavastatin, and other statins), (ii) bile acid sequestrants (cholestyramine, colestipol, dialkylaminoalkyl derivatives of a cross-linked dextran, Colestid®, LoCholest®, (iii) niacin and related compounds, such as nicotinyl alcohol, nicotinamide, and nicotinic acid or a salt thereof, (iv) PPARα agonists, such as gemfibrozil and fenofibric acid derivatives (fibrates), including clofibrate, fenofibrate, bezafibrate, ciprofibrate, and etofibrate, (v) cholesterol absorption inhibitors, such as stanol esters, beta-sitosterol, sterol glycosides such as tiqueside; and azetidinones, such as ezetimibe, (vi) acyl CoA:cholesterol acyltransferase (ACAT) inhibitors, such as avasimibe and melinamide, and including selective ACAT-1 and ACAT-2 inhibitors and dual inhibitors, (vii) phenolic anti-oxidants, such as probucol, (viii) microsomal triglyceride transfer protein (MTP)/ApoB secretion inhibitors, (ix) anti-oxidant vitamins, such as vitamins C and E and beta carotene, (x) thyromimetics, (xi) LDL (low density lipoprotein) receptor inducers, (xii) platelet aggregation inhibitors, for example glycoprotein IIb/IIIa fibrinogen receptor antagonists and aspirin, (xiii) vitamin B12 (also known as cyanocobalamin), (xiv) folic acid or a pharmaceutically acceptable salt or ester thereof, such as the sodium salt and the methylglucamine salt, (xv) FXR and LXR ligands, including both inhibitors and agonists, (xvi) agents that enhance ABCA1 gene expression, and (xvii) ileal bile acid transporters.

Preferred classes of therapeutic compounds that can be used with the compounds of this invention for use in improving a patient's lipid profile (i.e. raising HDL-C and lowering LDL-C) include one or both of statins and cholesterol absorption inhibitors. Particularly preferred are combinations of compounds of this invention with simvastatin, ezetimibe, or both simvastatin and ezetimibe. Also preferred are combinations of compounds of this invention with statins other than simvastatin, such as lovastatin, rosuvastatin, pravastatin, fluvastatin, atorvastatin, rivastatin, itavastatin, and ZD-4522.

Finally compounds of this invention can be used with compounds that are useful for treating other diseases, such as diabetes, hypertension and obesity, as well as other anti-atherosclerotic compounds. Such combinations may be used to treat one or more of such diseases as diabetes, obesity, atherosclerosis, and dyslipidemia, or more than one of the diseases associated with metabolic syndrome. The combinations may exhibit synergistic activity in treating these disease, allowing for the possibility of administering reduced doses of active ingredients, such as doses that otherwise might be sub-therapeutic.

Examples of other active ingredients that may be administered in combination with a compound of this invention include, but are not limited to, compounds that are primarily anti-diabetic compounds, including:

(a) PPAR gamma agonists and partial agonists, including glitazones and non-glitazones (e.g. pioglitazone, englitazone, MCC-555, rosiglitazone, balaglitazone, netoglitazone, T-131, LY-300512, and LY-818;

(b) biguanides such as metformin and phenformin;

(c) protein tyrosine phosphatase-1B (PTP-1B) inhibitors;

(d) dipeptidyl peptidase IV (DP-IV) inhibitors, including vildagliptin, sitagliptin, and saxagliptin;

(e) insulin or insulin mimetics, such as for example insulin lispro, insulin glargine, insulin zinc suspension, and inhaled insulin formulations;

(f) sulfonylureas, such as tolbutamide, glipizide, glimepiride, acetohexamide, chlorpropamide, glibenclamide, and related materials;

(g) α-glucosidase inhibitors (such as acarbose, adiposine; camiglibose; emiglitate; miglitol; voglibose; pradimicin-Q; and salbostatin);

(h) PPARα/γ dual agonists, such as muraglitazar, tesaglitazar, farglitazar, and naveglitazar;

(i) PPARδ agonists such as GW501516 and those disclosed in WO97/28149;

(j) glucagon receptor antagonists;

(k) GLP-1; GLP-1 derivatives; GLP-1 analogs, such as exendins, such as for example exenatide (Byetta); and nonpeptidyl GLP-1 receptor agonists;

(l) GIP-1; and (m) Non-sulfonylurea insulin secretagogues, such as the meglitinides (e.g. nateglinide and rapeglinide).

These other active ingredients that may be used in combination with the current invention also include antiobesity compounds, including 5-HT (serotonin) inhibitors, neuropeptide Y5 (NPY5) inhibitors, melanocortin 4 receptor (Mc4r) agonists, cannabinoid receptor 1 (CB-1) antagonists/inverse agonists, and $\beta_3$ adrenergic receptor agonists. These are listed in more detail later in this section.

These other active ingredients also include active ingredients that are used to treat inflammatory conditions, such as aspirin, non-steroidal anti-inflammatory drugs, glucocorticoids, azulfidine, and selective cyclooxygenase-2 (COX-2) inhibitors, including etoricoxib, celecoxib, rofecoxib, and Bextra.

Antihypertensive compounds may also be used advantageously in combination therapy with the compounds of this invention. Examples of antihypertensive compounds that may be used with the compounds of this invention include (1) angiotensin II antagonists, such as losartan; (2) angiotensin converting enzyme inhibitors (ACE inhibitors), such as enalapril and captopril; (3) calcium channel blockers such as nifedipine and diltiazam; and (4) endothelian antagonists.

Anti-obesity compounds may be administered in combination with the compounds of this invention, including: (1) growth hormone secretagogues and growth hormone secretagogue receptor agonists/antagonists, such as NN703, hexarelin, and MK-0677; (2) protein tyrosine phosphatase-1B (PTP-1B) inhibitors; (3) cannabinoid receptor ligands, such as cannabinoid $CB_1$ receptor antagonists or inverse agonists, such as rimonabant (Sanofi Synthelabo), AMT-251, and SR-14778 and SR 141716A (Sanofi Synthelabo), SLV-319 (Solvay), BAY 65-2520 (Bayer); (4) anti-obesity serotonergic agents, such as fenfluramine, dexfenfluramine, phentermine, and sibutramine; (5) γ3-adrenoreceptor agonists, such as AD9677/TAK677 (Dainippon/Takeda), CL-316,243, SB 418790, BRL-37344, L-796568, BMS-196085, BRL-35135A, CGP12177A, BTA-243, Trecadrine, Zeneca D7114, and SR 59119A; (6) pancreatic lipase inhibitors, such as orlistat (Xenical®), Triton WR1339, RHC80267, lipstatin, tetrahydrolipstatin, teasaponin, and diethylumbelliferyl phosphate; (7) neuropeptide Y1 antagonists, such as BIBP3226, J-115814, BIBO 3304, LY-357897, CP-671906, and GI-264879A; (8) neuropeptide Y5 antagonists, such as GW-569180A, GW-594884A, GW-587081X, GW-548118X, FR226928, FR 240662, FR252384, 1229U91, GI-264879A, CGP71683A, LY-377897, PD-160170, SR-120562A, SR-120819A and JCF-104; (9) melanin-concentrating hormone (MCH) receptor antagonists; (10) melanin-concentrating hormone 1 receptor (MCH1R) antagonists, such as T-226296 (Takeda); (11) melanin-concentrating hormone 2 receptor (MCH2R) agonist/antagonists; (12) orexin-1 receptor antagonists, such as SB-334867-A; (13) melanocortin agonists, such as Melanotan II; (14) other Mc4r (melanocortin 4 receptor) agonists, such as CHIR86036 (Chiron), ME-10142, and ME-10145 (Melacure), CHIR86036 (Chiron); PT-141, and PT-14 (Palatin); (15) 5HT-2 agonists; (16) 5HT2C (serotonin receptor 2C) agonists, such as BVT933, DPCA37215, WAY161503, and R-1065; (17) galanin antagonists; (18) CCK agonists; (19) CCK-A (cholecystokinin-A) agonists, such as AR-R 15849, GI 181771, JMV-180, A-71378, A-71623 and SR146131; (20) GLP-1 agonists; (21) corticotropin-releasing hormone agonists; (22) histamine receptor-3 (H3) modulators; (23) histamine receptor-3 (H3) antagonists/inverse agonists, such as hioperamide, 3-(1H-imidazol-4-yl)propyl N-(4-pentenyl)carbamate, clobenpropit, iodophenpropit, imoproxifan, and GT2394 (Gliatech); (24) β-hydroxy steroid dehydrogenase-1 inhibitors (11β-HSD-1 inhibitors), such as BVT 3498 and, BVT 2733, (25) PDE (phosphodiesterase) inhibitors, such as theophylline, pentoxifylline, zaprinast, sildenafil, amrinone, milrinone, cilostamide, rolipram, and cilomilast; (26) phosphodiesterase-3B (PDE3B) inhibitors; (27) NE (norepinephrine) transport inhibitors, such as GW 320659, despiramine, talsupram, and nomifensine; (28) ghrelin receptor antagonists; (29) leptin, including recombinant human leptin (PEG-OB, Hoffman La Roche) and recombinant methionyl human leptin (Amgen); (30) leptin derivatives; (31) BRS3 (bombesin receptor subtype 3) agonists such as [D-Phe6,beta-Ala11,Phe13,Nle14]Bn(6-14) and [D-Phe6,Phe13]Bn(6-13)propylamide; (32) CNTF (Ciliary neurotrophic factors), such as GI-181771 (Glaxo-SmithKline), SR146131 (Sanofi Synthelabo), butabindide, PD170,292, and PD 149164 (Pfizer); (33) CNTF derivatives, such as axokine (Regeneron); (34) monoamine reuptake inhibitors, such as sibutramine; (35) UCP-1 (uncoupling protein-1, 2, or 3) activators, such as phytanic acid, 4-[(E)-2-(5,6,7,8-tetrahydro-5,5,8,8-tetramethyl-2-napthalenyl)-1-propenyl]benzoic acid (TTNPB), and retinoic acid; (36) thyroid hormone β agonists, such as KB-2611 (KaroBioBMS); (37) FAS (fatty acid synthase) inhibitors, such as Cerulenin and C75; (38) DGAT1 (diacylglycerol acyltransferase 1) inhibitors; (39) DGAT2 (diacylglycerol acyltransferase 2) inhibitors; (40) ACC2 (acetyl-CoA carboxylase-2) inhibitors; (41) glucocorticoid antagonists; (42) acyl-estrogens, such as oleoyl-estrone; (43) dicarboxylate transporter inhibitors; (44) peptide YY, PYY 3-36, peptide YY analogs, derivatives, and fragments such as BIM-43073D, BIM-43004C, (45) Neuropeptide Y2 (NPY2) receptor agonists such NPY3-36, N acetyl [Leu(28,31)] NPY 24-36, TASP-V, and cyclo-(28/32)-Ac-[Lys28-Glu32]-(25-36)-pNPY; (46) Neuropeptide Y4 (NPY4) agonists such as pancreatic peptide (PP); (47) Neuropeptide Y1 (NPY1) antagonists such as BIBP3226, J-115814, BIBO 3304, LY-357897, CP-671906, and GI-264879A; (48) Opioid antagonists, such as nalmefene (Revex®), 3-methoxynaltrexone, naloxone, and naltrexone; (49) glucose transporter inhibitors; (50) phosphate transporter inhibitors; (51) 5-HT (serotonin) inhibitors; (52) beta-blockers; (53) Neurokinin-1 receptor antagonists (NK-1 antagonists); (54) clobenzorex; (55) cloforex; (56) clominorex; (57) clortermine; (58) cyclexedrine; (59) dextroamphetamine; (60) diphemethoxidine, (61) N-ethylamphetamine; (62) fenbutrazate; (63) fenisorex; (64) fenproporex; (65) fludorex; (66) fluminorex; (67) furfurylmethylamphetamine; (68) levamfetamine; (69) levophacetoperane; (70) mefenorex; (71) metamfepramone; (72) methamphetamine; (73) norpseudoephedrine; (74) pentorex; (75) phendimetrazine; (76) phenmetrazine; (77) picilorex; (78) phytopharm 57; (79) zonisamide, (80) aminorex, (81) amphechloral; (82) amphetamine; (83) benzphetamine; and (84) chlorphentermine.

The combination therapies described above which use the compounds of this invention may also be useful in the treatment of the metabolic syndrome. According to one widely used definition, a patient having metabolic syndrome is characterized as having three or more symptoms selected from the following group of five symptoms: (1) abdominal obesity; (2) hypertriglyceridemia; (3) low high-density lipoprotein cholesterol (HDL); (4) high blood pressure; and (5) elevated fasting glucose, which may be in the range characteristic of Type 2 diabetes if the patient is also diabetic. Each of these symptoms is defined clinically in the recently released Third Report of the National Cholesterol Education Program Expert Panel on Detection, Evaluation and Treatment of High Blood Cholesterol in Adults (Adult Treatment Panel III, or ATP III), National Institutes of Health, 2001, NIH Publication No. 01-3670. Patients with metabolic syndrome have an increased risk of developing the macrovascular and microvascular complications that are listed above, including atherosclerosis and coronary heart disease. The combinations described above may ameliorate more than one symptom of metabolic syndrome concurrently (e.g. two symptoms, three symptoms, four symptoms, or all five of the symptoms).

CETP Assay

An in vitro continuous assay for determining $IC_{50}$'s to identify compounds that are CETP inhibitors was performed based on a modification of the method described by Epps et al. employing BODIPY®-CE as the cholesteryl ester lipid donor and BODIPY®-TG as the triglyceride lipid donor. See Epps et al. (1995) *Method for measuring the activities of cholesteryl ester transfer protein (lipid transfer protein)*, *Chem. Phys. Lipids.* 77, 51-63.

Particles used in the assay were created from the following materials by probe sonication essentially as described by Epps et al. Synthetic cholesteryl ester (CE) donor HDL particles contained DOPC (Dioleoyl Phosphatidyl Choline), BODIPY®-CE (Molecular Probes C-3927), triolein (a triglyceride), dabcyl dicetylamide, (a non-diffusible quencher molecule to reduce background fluorescence) and apoHDL. Synthetic triglyceride (TG) donor HDL particles contained DOPC, BODIPY®-TG, and apoHDL. BODIPY®-TG was synthesized at room temperature from diolein and the BODIPY containing fatty acid analog 4,4-difluoro-5-(2-thienyl)-4-bora-3a,4a-diaza-s-indacene-3-dodecanoic acid (Molecular Probes) in methylene chloride in the presence of dicyclohexyl carbodimide. Dabcyl dicetylamide was made by heating dabcyl n-succinimide with dicetylamine in DMF at 95° C. overnight in the presence of diisopropylamine catalyst. Native lipoproteins from human blood were used as acceptor particles. Particles having a density less than 1.063 g/ml were collected by ultracentrifugation. These particles include VLDL, IDL, and LDL. Particle concentrations were expressed in terms of protein concentration as determined by BCA assay (Pierce, USA). Particles were stored at 4° C. until use.

Assays were performed in Dynex Microfluor 2 U-bottom black 96-well plates (Cat #7205). An assay cocktail containing CETP, 1×CETP buffer (50 mM Tris, pH 7.4, 100 mM NaCl, 1 mM EDTA), 3% human serum, and half the final concentration of acceptor particles was prepared, and 100 µL of the assay cocktail was added to each well of the plate. Test compounds in DMSO were added in a volume of 3 µL. The plate was mixed on a plate shaker and then incubated at 25° C. for 1 hour. A second assay cocktail containing donor particles, the remaining acceptor particles and 1×CETP buffer was prepared. 47 µL of the second assay cocktail was added to the reaction wells to start the assay. Assays were performed in a final volume of 150 µL. CE transfer reactions were performed as follows: final concentrations of materials were: 2.5 ng/µCE donor particles, 7.5 ng/µL acceptor particles (each expressed by protein content), 1×CETP buffer, 14-30 nM recombinant human CETP (expressed in CHO cells and partially purified), and up to 2% DMSO when testing compounds; reactions were followed in a fluorescence plate reader (Molecular Devices Spectramax GeminiXS) set for a 45 minute kinetic run at 25° C. which read the samples every 45 sec at Ex=480 nm, Em=511 nm, with a cutoff filter at 495 nm, photomultiplier tube setting of medium, calibration on, and 6 reads/well. TG transfer reactions were performed as described above with the exception that 2.5 ng/uL TG donor particles were used. TG transfer was measured at an excitation wavelength of 538 nm while reading emission at 568 nm every 45 sec for 45 min at 37° C. with a cutoff filter at 550 nm.

Data were evaluated by obtaining an initial rate, expressed in relative fluorescence units per second, for the pseudolinear portion of the curve, often 0-500 or 1000 sec. Comparison of the rates of samples with inhibitors to an uninhibited (DMSO only) positive control yielded a percent inhibition. A plot of percent inhibition vs. log of inhibitor concentration, fit to a Sigmoidal 4 parameter equation was used to calculate $IC_{50}$.

EXAMPLES

The following schemes and examples are provided so that the invention will be more fully appreciated and understood. Starting materials are made using known procedures or as shown below.

The examples should not be construed as limiting the invention in any way. The scope of the invention is defined by the appended claims. Compounds of this invention have an $IC_{50}$ value as measured for the CE transfer reaction of less than or equal to 21 µM. IC50 values are in the range of 13 nM to 21 uM. Most of the compounds have an $IC_{50}$ value of 13 nM-200 nM, and the preferred compounds generally have $IC_{50}$ values of 13 nM-100 nM. Each of the following representative compounds, or a stereoisomer thereof, has an $IC_{50}$ value in the range of 13 nM to 60 nM: Examples 1, 3, 19-23, 27-33, and 58.

Intermediate 1

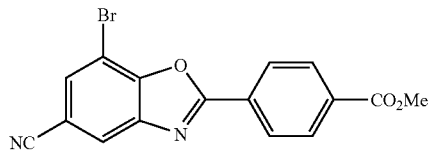

Methyl 4-(7-bromo-5-cyano-1,3-benzoxazol-2-yl)benzoate

Step A. 3-Bromo-4-hydroxy-5-nitrobenzonitrile

To a 5-l, 3-neck round-bottom flask fitted with a thermocouple, stirring paddle, and nitrogen line were added 3,5-dibromo-4-hydroxybenzonitrile (95 g) and glacial acetic acid (3.3 l). Sodium nitrite (120 g) was then added in small portions. The mixture was heated to 50° C. and stirred overnight at this temperature. The mixture was then allowed to cool and poured into a large extractor containing water (10 l). ethyl acetate (10 l) was added and the layers were separated. The aqueous layer was extracted with ethyl acetate (4 l) and the combined organic layers were washed with water and brine, and then dried over magnesium sulfate and concentrated in vacuo to provide 96.9 g of the desired product. Mass spectrum (ESI) 243.0 (M+).

Step B. 3-Amino-5-bromo-4-hydroxybenzonitrile

To a 22-l, 3-neck round-bottom flask fitted with a stirring paddle, a Claisen adapter fitted with a thermocouple and a condenser blanketed with nitrogen, and an addition funnel capped with a septum was added a mixture of 3-bromo-4-hydroxy-5-nitrobenzonitrile (96.9 g, Step A) in methanol (14 l). To this mixture was added iron (III) chloride (9.3 g) and activated charcoal (38 g, Darco 6-60, 100-mesh powder). The mixture was heated to reflux (65° C.) and stirred for 15 min at this temperature. Hydrazine (80 ml) was added to the refluxing mixture dropwise via addition funnel. Once the addition was complete, the mixture was stirred at reflux for 2 h. The mixture was then allowed to cool, filtered through Celite, washing with methanol, and concentrated to a red oil. A mixture of 300 ml of acetic acid and 700 ml of methanol was added and the mixture was concentrated again and then co-concentrated twice with 800 ml of toluene. The residue was purified by flash chromatography on an Isco Companion XL, 1.5 kg column, eluting with 3 column volumes of 30% ethyl acetate in hexanes, followed by a linear gradient of ethyl acetate in hexanes from 30 to 60% over 6 column volumes, followed by 2 column volumes of 60% ethyl acetate in hexanes to provide 40 g (55%) of the title compound. Mass spectrum (ESI) 214.9 (M+1).

Step C. Methyl 4-(7-bromo-5-cyano-1,3-benzoxazol-2-yl)benzoate

To a 3-l round-bottom flask fitted with a stir bar and a Claisen adapter fitted with a thermocouple and a condenser blanketed with nitrogen was added terephthalic acid monomethyl ester chloride (37.3 g) and a solution of 3-amino-5-bromo-4-hydroxybenzonitrile (40 g, Step B) in dioxane (675 ml). The mixture was heated to reflux and stirred at this temperature overnight. The mixture was then cooled to room temperature and the dioxane was removed in vacuo. The flask was fitted with a Dean-Stark trap and p-toluenesulfonic acid monohydrate (35.8 g) and toluene (2.5 l) were added. The mixture was heated to reflux and stirred at this temperature overnight. The mixture was then allowed to cool, transferred to a new 5-l flask, and concentrated to a brown solid. The crude product was triturated with methanol to provide 55.5 g (83%) of the title compound. $^1$H NMR (500 MHz, DMSO-$d_6$): δ 8.50 (s, 1H), 8.34 (d, J=8.0 Hz, 2H), 8.29 (s, 1H), 8.19 (d, J=8.0 Hz, 2H), 3.91 (s, 3H).

Intermediate 2

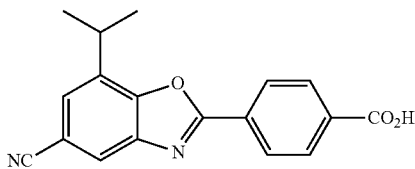 [SMILES: CC(C)c1cc(C#N)cc2nc(-c3ccc(C(=O)O)cc3)oc12]

4-(5-Cyano-7-isopropyl-1,3-benzoxazol-2-yl)benzoic acid

Step A. Methyl 4-(5-cyano-7-isopropenyl-1,3-benzoxazol-2-yl)benzoate

To a 5-l, 3-neck round-bottom flask fitted with a stirring paddle, a condenser blanketed with nitrogen, and a thermocouple, was added 4-(7-bromo-5-cyano-1,3-benzoxazol-2-yl)benzoate (55.5 g, INTERMEDIATE 1) toluene (2 l), water (375 ml), ethanol (150 ml), 2M aqueous sodium carbonate (250 ml), and isoprenylboronic acid (83.4 g, INTERMEDIATE 3). The mixture was purged with nitrogen three times and then tetrakis(triphenylphosphine)palladium(0) (9.1 g) was added, and the mixture was purged three times with nitrogen. The mixture was heated to reflux (91° C.) and stirred at this temperature overnight. The mixture was then cooled to 20° C. and the product was filtered, washed with water, dried, and transferred to a 3-l round-bottom flask and rinsed with toluene (1 l). Residual solvent was removed in vacuo. Mass spectrum (ESI) 319.1 (M+1).

Step B. Methyl 4-(5-cyano-7-isopropyl-1,3-benzoxazol-2-yl)benzoate

To a 5-gallon reaction vessel was added methyl 4-(5-cyano-7-isopropenyl-1,3-benzoxazol-2-yl)benzoate (40.6 g, Step A), tetrahydrofuran (4 l), and 10% palladium on carbon (8 g). The reaction mixture was heated to 60° C. under 10 psi of hydrogen for 3 h, and then filtered through Celite, washing generously with dichloromethane. Concentration of the eluent in vacuo provided 40.5 g (99%) of the title compound. Mass spectrum (ESI) 321.1 (M+).

Step C. 4-(5-Cyano-7-isopropyl-1,3-benzoxazol-2-yl)benzoic acid

To a 5-l, round-bottom flask fitted with a stir bar and a Claisen adapter fitted with a thermocouple and a nitrogen line was added was added methyl 4-(5-cyano-7-isopropyl-1,3-benzoxazol-2-yl)benzoate (40.5 g, Step B) tetrahydrofuran (1.25 l), methanol (630 ml), water (315 ml), and lithium hydroxide monohydrate (10.7 g). The mixture was heated to 50° C. and stirred at this temperature for 1 h. The mixture was then cooled and concentrated to a thick slurry. 1N HCl (3.2 l) was added and an off-white solid formed. The mixture was stirred for 5 min and then filtered, washing with water (2×500 ml). The solid was transferred to a 2-l round-bottom flask, concentrated from toluene (1 l) and then dried in vacuo. Mass spectrum (ESI) 307.0 (M+1). $^1$H NMR (500 MHz, DMSOd$_6$): δ 8.69 (d, J=7.5 Hz, 2H), 8.28 (s, 1H), 8.16 (d, J=8.0 Hz, 2H), 7.81 (s, 1H), 3.46 (septet, J=6.5 Hz, 1H), 1.40 (d, H=7.0 Hz, 6H).

Intermediate 3

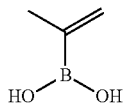

Isoprenylboronic Acid

To a 12-l, 3-neck round-bottom flask fitted with a stirring paddle, an addition funnel capped with a septum, and a Claisen adapter fitted with a thermocouple and a nitrogen line was added trimethyl borate (405 ml) and tetrahydrofuran (2.4 l). To this solution was added isoprenylmagnesium bromide (2.4 l of a 0.5 M solution in tetrahydrofuran) via the addition funnel, keeping the temperature below 30° C. using an ice-water bath. Upon completion of the addition, the mixture was stirred for 3 h at room temperature. The reaction mixture was poured into a large extractor containing 1 N HCl (4 l). Ether (4 l) was added, the layers were separated, and the aqueous layer was extracted with ether (2 l). The combined organic layers were dried over magnesium sulfate and concentrated in vacuo, keeping the temperature below 30° C., to provide 197.3 g of the title compound. $^1$H NMR (500 MHz, CDCl$_3$): δ 6.13 (s, 1H); 5.84 (s, 1H); 5.63 (app. d, J=12.1 Hz, 2H); 4.38 (br. s, 1H); 1.87 (app. d, J=21.7 Hz, 6H).

Intermediate 4

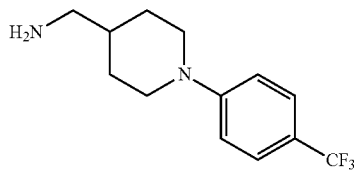

1-{1-[4-(Trifluoromethyl)phenyl]piperidin-4-yl}methanamine

Step A. tert-Butyl({1-[4-(trifluoromethyl)phenyl]piperidin-4-yl}methyl)carbamate To a mixture of sodium tert-butoxide, 1-iodo-4-(trifluoromethyl)benzene (686 µl) and tert-butyl(piperidin-4-ylmethyl)carbamate (1.00 g) in toluene (10 ml) was added 1,1'-binaphthalene-2,2'-diylbis(diphenylphosphine) (286 mg) and tris-dibenzylideneacetone palladium(0) (211 mg). The mixture was heated to 90° C. for 15 h. The mixture was cooled to room temperature, concentrated in vacuo, and diluted with dichloromethane. This solution was filtered through a short plug of silica gel and concentrated. The residue was purified via flash chromatography on a Biotage Horizon, 40M column, eluting with 10 column volumes of 33% ethyl acetate in hexanes to provide 1.36 g (81%) of the title compound. Mass spectrum (ESI) 303.0 (M+1).

Step B. 1-{1-[4-(Trifluoromethyl)phenyl]piperidin-4-yl}methanamine

A mixture of trifluoroacetic acid (10 ml) and dichloromethane (10 ml) was added to tert-butyl({1-[4-(trifluoromethyl)phenyl]piperidin-4-yl}methyl)carbamate (1.36 g). This mixture was stirred at room temperature for 3 h. The sample was concentrated and taken up in dichloromethane (20 ml) and saturated aqueous sodium bicarbonate. The mixture was extracted and the organic layer was dried over sodium sulfate, filtered, and concentrated in vacuo to provide the title compound (1.21 g, 86%). Mass spectrum (ESI) 242.1 (M+1).

Intermediate 5

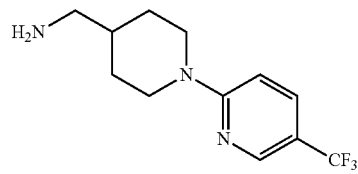 [SMILES: NCC1CCN(c2ccc(C(F)(F)F)cn2)CC1]

1-{1-[5-(Trifluoromethyl)pyridin-2-yl]piperidin-4-yl}methanamine

In a 5-ml microwave vial equipped was placed potassium carbonate (1.38 g), tert-butyl(piperidin-4-ylmethyl)carbamate (1.07 g), and 2-bromo-5-trifluoromethylpyridine (1.13 g) in methanol. This was heated to 120° C. for 30 min in a microwave reactor. The mixture was cooled and concentrated in vacuo, and the residue was taken up in ethyl acetate. This was filtered through a plug of silica gel, and the eluent was concentrated in vacuo to provide tert-butyl({1-[5-(trifluoromethyl)pyridin-2-yl]piperidin-4-yl}methyl)carbamate (1.45 g, 81%). This compound was taken up in 15 ml of dichloromethane and 15 ml of trifluoroacetic acid. The resultant mixture was stirred at room temperature for 2 h, and then concentrated and taken up in dichloromethane (20 ml) and saturated aqueous sodium bicarbonate. The mixture was extracted and the organic layer was dried over sodium sulfate, filtered, and concentrated in vacuo to provide 1.31 g (87%) of the title compound. Mass spectrum (ESI) 260.1 (M+1).

Following the procedure described in INTERMEDIATE 5, the compounds listed in Table 1 were prepared:

TABLE 1

| INTER-MEDIATE | R | MS (M + 1) |
|---|---|---|
| 6 | ![structure] H$_2$N piperidine-pyrimidine-CF$_3$ | 261.1 |
| 7 | ![structure] H$_2$N piperidine-pyrimidine-Cl | 227.1 |

TABLE 1-continued

| INTER-MEDIATE | R | MS (M + 1) |
|---|---|---|
| 8 | H₂N-CH₂-piperidine-N-pyrimidine-OMe | 223.2 |
| 9 | H₂N-CH₂-piperidine-N-pyridine-CO₂Me | 250.3 |
| 10 | H₂N-CH₂-piperidine-N-pyridine-CO₂Me | 250.3 |
| 11 | H₂N-CH₂-piperidine-N-pyridine-CF₃ | 260.1 |
| 12 | H₂N-CH₂-piperidine-N-pyridine-CF₃ | 260.1 |
| 13 | H₂N-CH₂-piperidine-N-pyridine-Br | 272.0 |
| 14 | H₂N-CH₂-piperidine-N-pyrimidine-Br | 273.0 |

Example 1

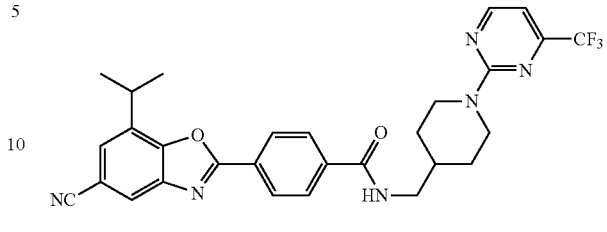

4-(5-Cyano-7-isopropyl-1,3-benzoxazol-2-yl)-N-({1-[4-(trifluoromethyl)pyrimidin-2-yl]piperidin-4-yl}methyl)benzamide Step A. Lithium 4-(5-cyano-7-isopropyl-1,3-benzoxazol-2-yl)benzoate Methyl 4-(5-cyano-7-isopropyl-1,3-benzoxazol-2-yl)benzoate (118 mg, INTERMEDIATE 2, Step A) and lithium hydroxide (18 mg) were combined in 10 ml of a 1:1:1 mixture of tetrahydrofuran, methanol, and water. The solution was stirred at 50° C. for 5 h. The solvents were removed in vacuo to provide the title compound as an off-white solid (123 mg). Mass spectrum (ESI) 307.0 (M+1).

Step B. 4-(5-Cyano-7-isopropyl-1,3-benzoxazol-2-yl)-N-({1-[4-(trifluoromethyl)pyrimidin-2-yl]piperidin-4-yl}methyl)benzamide To lithium 4-(5-cyano-7-isopropyl-1,3-benzoxazol-2-yl)benzoate (46 mg) in 5 ml of dichloromethane was added 2.5 ml of a 2M solution of oxalyl chloride in dichloromethane followed by 10 µl of dimethylformamide. The mixture was warmed and stirred until the solids dissolved (1 h). The mixture was then concentrated in vacuo (with minimal or no heating (<30° C.), and then dried under high vacuum to remove traces of water. To the residue was added 2.5 ml of dichloromethane (1 M in dichloromethane), 43 mg of ({1-[4-(trifluoromethyl)pyrimidin-2-yl]piperidin-4-yl}methyl) amine (INTERMEDIATE 6), and 78 µl of diisopropylethylamine. The mixture was stirred at room temperature for 30 min and then concentrated in vacuo. The residue was dissolved in ethyl acetate and filtered though a short plug of silica gel, eluting with ethyl acetate. The eluent was concentrated in vacuo and the residue transferred directly to a preparative TLC plate with dichloromethane ($R_f$=0.41 in 1:1 hexanes/ethyl acetate). After this purification, the product was still a slightly yellow color. This color was removed by triturating twice with a small amount (0.5 ml) of methanol to provide 25 mg, (30%) of the title compound as a white, insoluble solid. Mass spectrum (ESI) 549.0 (M+1). $^1$H NMR (500 MHz, CDCl₃): δ 8.48 (d, J=4.8 Hz, 1H), 8.34 (m, J=8.5 Hz, 2H), 7.95 (m, 3H), 7.51 (s, 1H), 6.73 (d, J=4.8 Hz, 1H), 6.36 (br s, 1H), 4.87 (d, J=13.5 Hz, 2H), 3.45 (t, J=6.4 Hz, 2H), 2.96 (m, 4H), 1.92 (m, 3H), 1.85, (septet, J=7.5 Hz, 1H), 1.46 (d, J=7.0 Hz, 6H).

Following the procedure described in EXAMPLE 1, the compounds listed in Table 2 were prepared:

TABLE 2

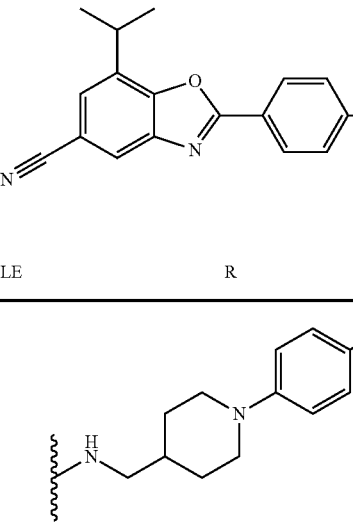

| EXAMPLE | R | MS (M + 1) |
|---|---|---|
| 2 | 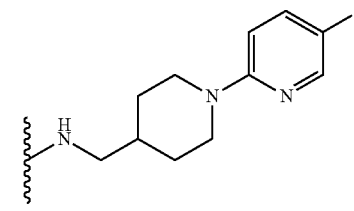 | 547.1 |
| 3 | 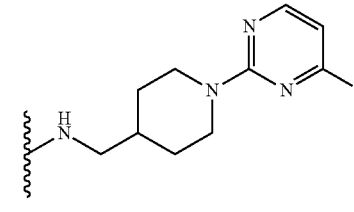 | 548.2 |
| 4 | 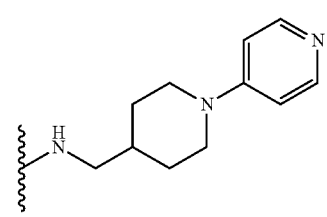 [SMILES: *NCC1CCN(c2ccncc2)CC1] | 549.1 |
| 5 | 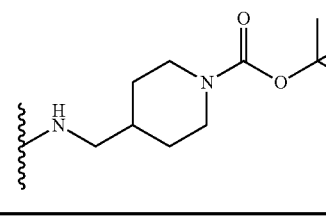 | 480.2 |
| 6 | 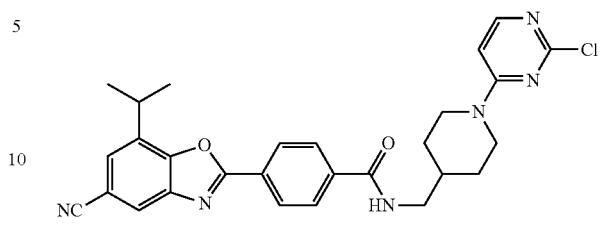 | 503.2 |

Example 7

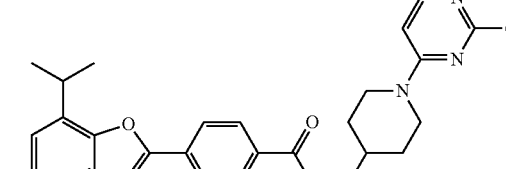

N-{[1-(2-Chloropyrimidin-4-yl)piperidin-4-yl]methyl}-4-(5-cyano-7-isopropyl-1,3-benzoxazol-2-yl)benzamide The title compound was prepared using a procedure analogous to that described in EXAMPLE 1. Mass spectrum (ESI) 515.2 (M+1). $^1$H NMR (500 MHz, CDCl$_3$): δ 8.34 (d, J=8.0 Hz, 2H), 8.14 (d, J=5.1 Hz, 1H), 7.95 (d, J=8.0, 3H), 7.52 (s, 1H), 6.48 (d, J=5.0 Hz, 1H), 6.30 (bs, 1H), 4.80 (d, J=13.5 Hz, 2H), 3.48 (sept, J=6.8 Hz, 1H), 3.45 (t, J=6.4, 2H), 2.91 (m, 2H), 1.89, (m, 1H), 1.88 (m, 2H), 1.46 (d, J=7.0, 6H), 1.39 (m, 2H).

Example 8

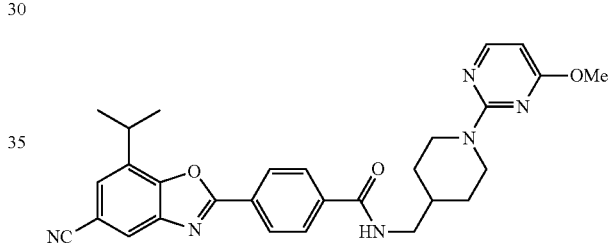

4-(5-Cyano-7-isopropyl-1,3-benzoxazol-2-yl)-N-{[1-(4-methoxypyrimidin-2-yl)piperidin-4-yl]methyl}benzamide The title compound was prepared using a procedure analogous to that described in EXAMPLE 1. Mass spectrum (ESI) 516.4 (M+1). $^1$H NMR (500 MHz, CDCl$_3$): δ 8.28 (d, J=7.9 Hz, 2H), 8.08 (d, J=5.1 Hz, 1H), 7.89 (d, J=7.8 Hz, 2H), 7.74 (d, J=5.1 Hz, 1H), 7.55 (s, 1H), 6.30 (bs, 1H), 6.18 (d, J=5.0 Hz, 1H), 4.81 (d, J=13.3 Hz, 2H), 4.19 (s, 3H), 3.49 (sept, J=6.9 Hz, 1H), 2.91 (m, 2H), 1.88, (m, 3H), 1.45 (d, J=6.9 Hz, 6H), 1.38 (m, 2H).

Example 9

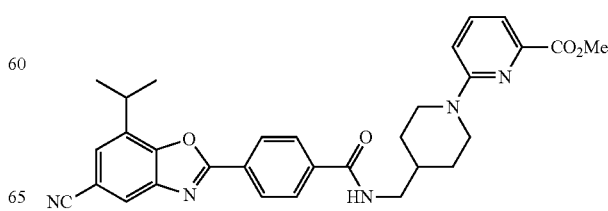

Methyl 6-[4-({[4-(5-cyano-7-isopropyl-1,3-benzoxazol-2-yl)benzoyl]amino methyl)piperidin-1-yl]pyridine-2-carboxylate The title compound was prepared using a procedure analogous to that described in EXAMPLE 1. Mass spectrum (ESI) 538.2 (M+1). $^1$H NMR (500 MHz, CDCl$_3$): δ 8.34 (d, J=8.4 Hz, 2H), 7.95 (d, J=8.8 Hz, 1H), 7.94 (s, 1H), 7.56 (dd, J=8.5, 7.4 Hz, 2H), 7.52 (s, 1H), 6.83 (d, J=8.5 Hz, 2H), 6.32 (t, J=5.8 Hz, 1H), 4.45 (d, J=13.2 Hz, 2H), 3.93 (s, 3H), 3.47 (sept, J=6.9 Hz, 1H), 3.45 (t, J=6.4 Hz, 2H), 2.90 (t, J=13.0 Hz, 2H), 1.88, (m, 3H), 1.46 (d, J=7.1 Hz, 6H), 1.39 (m, 2H).

Example 10

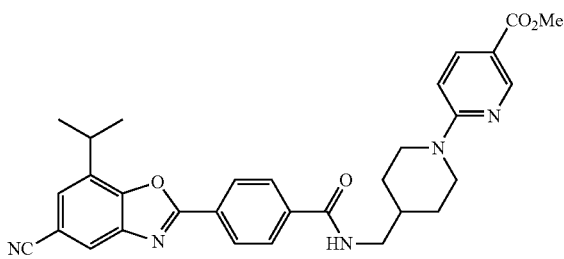 [SMILES: COC(=O)c1ccc(N2CCC(CNC(=O)c3ccc(-c4nc5cc(C#N)cc(C(C)C)c5o4)cc3)CC2)nc1]

Methyl 6-[4-({[4-(5-cyano-7-isopropyl-1,3-benzoxazol-2-yl)benzoyl]amino methyl)piperidin-1-yl]nicotinate The title compound was prepared using a procedure analogous to that described in EXAMPLE 1. Mass spectrum (ESI) 538.3 (M+1). $^1$H NMR (500 MHz, CDCl$_3$): δ 8.34 (d, J=8.4 Hz, 2H), 7.95 (d, J=8.8 Hz, 1H), 7.94 (s, 1H), 7.56 (dd, J=8.5 Hz, 7.4 Hz, 2H), 7.52 (s, 1H), 6.83 (d, J=8.5 Hz, 2H), 6.32 (t, J=5.8 Hz, 1H), 4.45 (d, J=13.2 Hz, 2H), 3.93 (s, 3H), 3.47 (sept, J=6.9 Hz, 1H), 3.45 (t, J=6.4 Hz, 2H), 2.90 (t, J=13.0 Hz, 2H), 1.88, (m, 3H), 1.46 (d, J=7.1 Hz, 6H), 1.39 (m, 2H).

Example 11

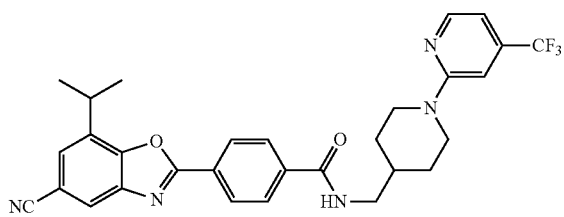 [SMILES: CC(C)c1cc(C#N)cc2nc(-c3ccc(C(=O)NCC4CCN(c5cc(C(F)(F)F)ccn5)CC4)cc3)oc12]

4-(5-Cyano-7-isopropyl-1,3-benzoxazol-2-yl)-N-({1-[4-(trifluoromethyl)pyridin-2-yl]piperidin-4-yl}methyl)benzamide The title compound was prepared using a procedure analogous to that described in EXAMPLE 1. Mass spectrum (ESI) 548.3 (M+1). $^1$H NMR (500 MHz, CDCl$_3$): δ 8.34 (d, J=8.3 Hz, 2H), 7.95 (d, J=8.3 Hz, 1H), 7.95 (s, 1H), 7.56 (t, J=6.8 Hz, 2H), 7.52 (s, 1H), 6.92 (d, J=8.3 Hz, 1H), 6.81 (d, J=8.7 Hz, 1H), 6.33 (t, J=5.8 Hz, 1H), 4.42 (d, J=13.1 Hz, 2H), 3.48 (sept, J=6.8 Hz, 1H), 3.45 (t, J=6.4 Hz, 2H), 2.90 (t, J=13.0 Hz, 2H), 1.92, (m, 3H), 1.46 (d, J=6.8 Hz, 6H), 1.40 (m, 2H).

Example 12

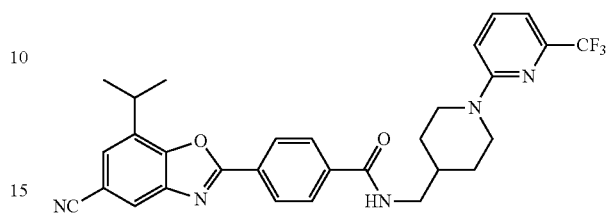

4-(5-Cyano-7-isopropyl-1,3-benzoxazol-2-yl)-N-({1-[4-(trifluoromethyl)pyridin-2-yl]piperidin-4-yl}methyl)benzamide The title compound was prepared using a procedure analogous to that described in EXAMPLE 1. Mass spectrum (ESI) 548.2 (M+1). $^1$H NMR (500 MHz, CDCl$_3$): □ 8.34 (d, J=8.3 Hz, 2H), 7.95 (d, J=8.3 Hz, 1H), 7.95 (s, 1H), 7.56 (t, J=6.8 Hz, 2H), 7.52 (s, 1H), 6.92 (d, J=8.3 Hz, 1H), 6.81 (d, J=8.7 Hz, 1H), 6.33 (t, J=5.8 Hz, 1H), 4.42 (d, J=13.1 Hz, 2H), 3.48 (sept, J=6.8 Hz, 1H), 3.45 (t, J=6.4 Hz, 2H), 2.90 (t, J=13.0 Hz, 2H), 1.92, (m, 3H), 1.46 (d, J=6.8 Hz, 6H), 1.37 (m, 2H).

Example 13

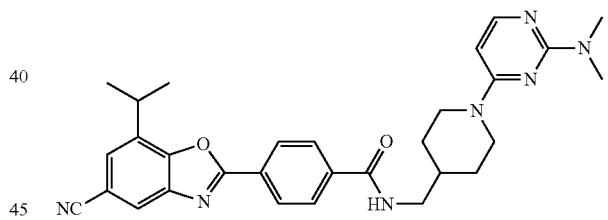

4-(5-Cyano-7-isopropyl-1,3-benzoxazol-2-yl)-N-({1-[2-(dimethylamino)pyrimidin-4-yl]piperidin-4-yl}methyl)benzamide A 5-ml microwave vial was charged with N-{[1-(2-chloropyrimidin-4-yl)piperidin-4-yl]methyl}-4-(5-cyano-7-isopropyl-1,3-benzoxazol-2-yl)benzamide (31 mg, EXAMPLE 7) and dimethylamine (2M in tetrahydrofuran, 3 ml). The resultant mixture was heated to 130° C. for 15 min in a microwave reactor. The mixture was concentrated in vacuo and the residue purified via flash chromatography on a Biotage Horizon 25M column, eluting with 10 column volumes of 100% ethyl acetate, to provide the title compound (15 mg, 48%). Mass spectrum (ESI) 524.3 (M+1). $^1$H NMR (500 MHz, CDCl$_3$): δ 8.34 (d, J=8.2 Hz, 2H), 7.94 (m, 5H), 7.52 (s, 1H), 6.30 (t, J=5.8 Hz, 1H), 5.84 (d, J=6.0 Hz, 1H), 4.43 (d, J=10.8 Hz, 2H), 3.48 (sept, J=6.8 Hz, 1H), 3.45 (t, J=6.4 Hz, 2H), 3.13 (s, 3H), 2.84 (t, J=11.2 Hz, 2H), 1.93, (m, 3H), 1.46 (d, J=7.0 Hz, 6H), 1.37 (m, 2H).

Example 14

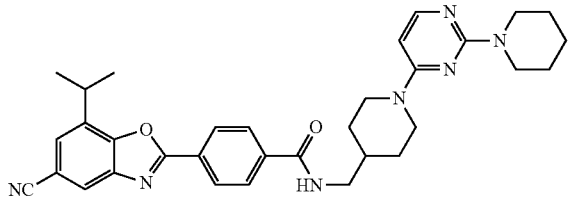 [SMILES: CC(C)c1cc(C#N)cc2nc(-c3ccc(C(=O)NCC4CCN(c5ccnc(N6CCCCC6)n5)CC4)cc3)oc12]

4-(5-Cyano-7-isopropyl-1,3-benzoxazol-2-yl)-N-{[1-(2-piperidin-1-ylpyrimidin-4-yl)piperidin-4-yl]methyl}benzamide The title compound was prepared using a procedure analogous to that described in EXAMPLE RS-13. Mass spectrum (ESI) 564.4 (M+1). $^1$H NMR (500 MHz, CDCl$_3$): δ 8.34 (d, J=8.2 Hz, 2H), 7.94 (m, 5H), 7.52 (s, 1H), 6.29 (t, J=5.8 Hz, 1H), 5.83 (d, J=6.0 Hz, 1H), 4.41 (d, J=10.8 Hz, 2H), 3.72 (m, 4H), 3.48 (sept, J=7.1 Hz, 1H), 3.43 (t, J=6.4 Hz, 2H), 2.84 (t, J=11.0 Hz, 2H), 1.93, (m, 3H), 1.59 (m, 6H), 1.46 (d, J=7.1 Hz, 6H), 1.30 (m, 2H).

Example 15

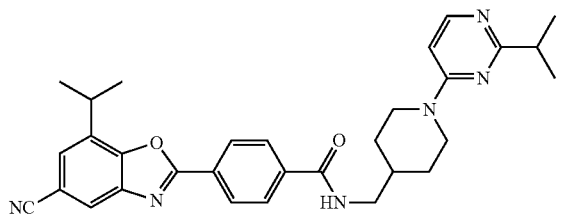 [SMILES: CC(C)c1nccc(N2CCC(CNC(=O)c3ccc(-c4nc5cc(C#N)cc(C(C)C)c5o4)cc3)CC2)n1]

4-(5-Cyano-7-isopropyl-1,3-benzoxazol-2-yl)-N-{[1-(2-isopropylpyrimidin-4-yl)piperidin-4-yl]methyl}benzamide Step. A. 4-(5-Cyano-7-isopropyl-1,3-benzoxazol-2-yl)-N-{[1-(2-isopropenylpyrimidin-4-yl)piperidin-4-yl]methyl}benzamide Sodium carbonate (120 uL, 2M aqueous), isopropenylboronic acid (21 mg), and N-{[1-(2-chloropyrimidin-4-yl)piperidin-4-yl]methyl}-4-(5-cyano-7-isopropyl-1,3-benzoxazol-2-yl)benzamide (31 mg, EXAMPLE 7) were dissolved in toluene (2.1 ml), water (0.6 ml) and ethanol (0.3 ml). To this solution was added palladium tetrakis(triphenylphosphine) (10 mg). The mixture was heated to 150° C. for 25 min in a microwave reactor. Upon cooling, the mixture was then concentrated in vacuo, taken up in dichloromethane, and purified via flash chromatography on a Biotage Horizon, 25 M column, eluting with 10 column volumes of ethyl acetate to provide the title compound (19 mg, 61%). Mass spectrum (ESI) 521.4 (M+1). $^1$H NMR (500 MHz, CDCl$_3$): δ 8.34 (d, J=8.5 Hz, 2H), 8.23 (d, J=6.2 Hz, 1H), 7.95 (d, J=8.0 Hz, 3H), 7.52 (s, 1H), 6.38 (d, J=6.2 Hz, 1H), 6.31 (t, J=6.0 Hz, 1H), 6.30 (s, 1H), 5.41 (s, 1H), 4.52 (d, J=8.7 Hz, 2H), 3.46 (m, 3H), 2.91 (t, J=12.4 Hz, 2H), 2.19 (s, 3H), 2.00 (m, 2H), 1.90 (d, J=12.2 Hz, 2H), 1.46 (d, J=7.0, 6H), 1.33 (m, 2H).

Step B. 4-(5-Cyano-7-isopropyl-1,3-benzoxazol-2-yl)-N-{[1-(2-isopropylpyrimidin-4-yl)piperidin-4-yl]methyl}benzamide To a solution of 4-(5-cyano-7-isopropyl-1,3-benzoxazol-2-yl)-N-{[1-(2-isopropenylpyrimidin-4-yl)piperidin-4-yl]methyl}benzamide (10 mg) in 1.33 ml of methanol and 0.66 ml of tetrahydrofuran was added 3 mg of 10% palladium on carbon. This mixture was evacuated and flushed with a hydrogen-filled balloon ten times. The reaction mixture was stirred at 50° C. for 1 h, and then at room temperature for 15 h. The mixture was then filtered through a plug of Celite, eluting with methanol. After concentration of the eluent in vacuo, the residue was further purified by filtration through a plug of silica gel, eluting with ethyl acetate. Concentration of the residue in vacuo provided the title compound (112 mg, 93%). Mass spectrum (ESI) 523.4 (M+1). $^1$H NMR (500 MHz, CDCl$_3$): δ 8.34 (d, J=8.3 Hz, 2H), 8.16 (d, J=6.2 Hz, 1H), 7.95 (d, J=8.0 Hz, 3H), 7.52 (s, 1H), 6.32 (m, 3H), 4.52 (d, J=9.1 Hz, 2H), 3.46 (m, 3H), 2.97 (sept, J=6.9 Hz, 1H), 2.91 (t, J=11.3 Hz, 2H), 2.00 (s, 1H), 1.88 (d, J=12.1 Hz, 2H), 1.46 (d, J=6.8, 6H), 1.33 (m, 2H), 1.28 (d, J=6.9, 6H).

Example 16

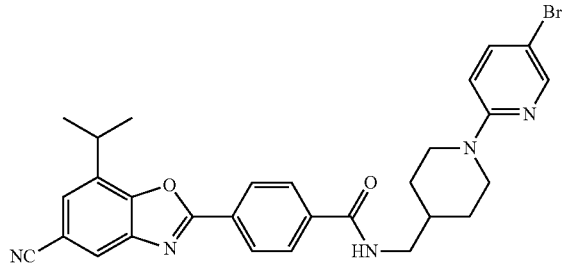 [SMILES: CC(C)c1cc(C#N)cc2nc(-c3ccc(C(=O)NCC4CCN(c5ccc(Br)cn5)CC4)cc3)oc12]

N-{[1-(5-Bromopyridin-2-yl)piperidin-4-yl]methyl}-4-(5-cyano-7-isopropyl-1,3-benzoxazol-2-yl)benzamide The title compound was prepared using a procedure analogous to that described in EXAMPLE 1. Mass spectrum (ESI) 560.0 (M+2). $^1$H NMR (500 MHz, CDCl$_3$): δ 8.34 (d, J=8.5 Hz, 2H), 8.18 (s, 1H), 7.94 (m, 3H), 7.52 (s, 1H), 7.51 (d, J=9.2 Hz, 1H), 6.56 (d, J=9.2 Hz, 1H), 6.30 (t, J=5.0 Hz, 1H), 4.29 (d, J=13.3 Hz, 2H), 3.49 (sept, J=7.1 Hz, 1H), 3.44 (t, J=6.4 Hz, 2H), 2.85 (t, J=13.1 Hz, 2H), 1.94, (m, 1H), 1.87, (d, J=12.8 Hz, 2H), 1.46 (d, J=7.1 Hz, 6H), 1.36 (m, 2H Following the procedure described in EXAMPLE 15, the compounds listed in Table 3 were prepared from N-{[1-(2-chloropyrimidin-4-yl)piperidin-4-yl]methyl}-4-(5-cyano-7-isopropyl-1,3-benzoxazol-2-yl)benzamide (EXAMPLE 7) or N-{[1-(5-bromopyridin-2-yl)piperidin-4-yl]methyl}-4-(5-cyano-7-isopropyl-1,3-benzoxazol-2-yl)benzamide (EXAMPLE 16):

TABLE 3

Core structure: 7-isopropyl-5-cyano-1,3-benzoxazol-2-yl benzamide with N-(piperidin-4-ylmethyl) where piperidine N bears group R.

| EXAMPLE | R | MS (M + 1) |
|---|---|---|
| 17 | 2-phenylpyrimidin-4-yl | 557.3 |
| 18 | pyridin-2-yl | 480.7 |
| 19 | 5-phenylpyridin-2-yl | 556.3 |
| 20 | 5-(5-fluoro-2-isopropoxyphenyl)pyridin-2-yl | 632.2 |
| 21 | 5-(2-isobutoxyphenyl)pyridin-2-yl | 628.4 |
| 22 | 5-(2-isopropylphenyl)pyridin-2-yl | 598.3 |
| 23 | 5-(2-isopropoxy-5-trifluoromethylphenyl)pyridin-2-yl | 682.4 |

TABLE 3-continued

| EXAMPLE | R | MS (M + 1) |
|---|---|---|
| 24 | 5-(2-phenoxy-5-trifluoromethylphenyl)pyridin-2-yl | 730.3 |

Example 25

N-{[1-(5-Bromopyrimidin-2-yl)piperidin-4-yl]methyl}-4-(5-Cyano-7-isopropyl-1,3-benzoxazol-2-yl)benzamide The title compound was prepared using a procedure analogous to that described in EXAMPLE 1. Mass spectrum (ESI) 570.0 (M+1). NMR (500 MHz, CDCl$_3$): δ 8.34 (d, J=8.5 Hz, 2H), 8.27 (s, 2H), 7.95 (d, J=8.0 Hz, 3H), 7.52 (s, 1H), 6.29 (t, J=5.9 Hz, 1H), 4.75 (d, J=13.5 Hz, 2H), 3.48 (sept, J=6.9 Hz, 1H), 3.43 (t, J=6.5 Hz, 2H), 2.89 (t, J=13.1 Hz, 2H), 1.97, (m, 1H), 1.87, (d, J=11.9 Hz, 2H), 1.46 (d, J=7.1 Hz, 6H), 1.29 (m, 2H).

Example 26

4-(5-Cyano-7-isopropyl-1,3-benzoxazol-2-yl)-N-({1-[5-(2-isopropoxy-5-methylphenyl)pyrimidin-2-yl]piperidin-4-yl}methyl)benzamide The title compound was prepared from N-{[1-(5-bromopyrimidin-2-yl)piperidin-4-yl]methyl}-4-(5-cyano-7-isopropyl-1,3-benzoxazol-2-yl)benzamide (EXAMPLE 25) using a procedure analogous to that described in EXAMPLE 15. Mass spectrum (ESI) 629.3 (M+1). NMR (500 MHz, CDCl$_3$): δ 8.53 (s, 1H), 8.35 (d, J=8.2 Hz, 2H), 7.95 (m, 3H), 7.52 (s, 1H), 7.33 (s, 1H), 7.06 (s, 1H), 6.87 (d, J=8.2 Hz, 1H), 6.32 (t, J=6.7 Hz, 1H), 4.87 (d, J=13.2 Hz, 2H), 4.49 (sept, J=5.9 Hz, 1H), 3.48 (m, 4H), 2.94 (t, J=13.7 Hz, 2H), 2.32 (s, 3H), 1.99 (m, 1H), 1.92 (d, J=13.8 Hz, 2H), 1.46 (d, J=6.8, 6H), 1.39 (m, 2H), 1.28 (d, J=6.2, 6H).

Following the procedure described in EXAMPLE 15, the compounds listed in Table 4 were prepared from N-{[1-(5-bromopyrimidin-2-yl)piperidin-4-yl]methyl}-4-(5-cyano-7-isopropyl-1,3-benzoxazol-2-yl)benzamide (EXAMPLE 25):

TABLE 4

| EXAMPLE | R | MS (M + 1) |
|---|---|---|
| 27 | 4-fluoro-α-methylenebenzyl | 601.1 |
| 28 | (E)-2-cyclopropylvinyl | 547.1 |
| 29 | cyclohex-1-en-1-yl | 561.2 |
| 30 | 2,3-dimethylbut-2-en-2-yl | 549.2 |
| 31 | 5-fluoro-4-isopropyl-2-methoxyphenyl | 647.2 |
| 32 | 2-(trifluoromethoxy)phenyl | 641.2 |
| 33 | 5-fluoro-2-isopropoxyphenyl | 633.2 |
| 34 | 1-methyl-1H-pyrazol-4-yl | 561.2 |

Example 35

Benzyl 4-({[4-(5-cyano-7-isopropyl-1,3-benzoxazol-2-yl)benzoyl]amino}methyl)piperidine-1-carboxylate To a suspension of 4-(5-cyano-7-isopropyl-1,3-benzoxazol-2-yl)benzoic acid (2 g, 6.53 mmol, INTERMEDIATE 2) in dichloromethane (25 ml) were added oxalyl chloride (9.79 ml, 19.59 mmol) and a drop (ca. 10 μl) of dimethylformamide. The mixture was stirred for 1 h at 25° C., at which point a clear solution formed. The mixture was concentrated and then co-concentrated with 5 ml of toluene. To a solution of the residue in dichloromethane (25 ml) was added 4-aminomethyl-1-N-Cbz-piperidine (2 g, 8.05 mmol) and diisopropylethylamine (1.711 ml, 9.79 mmol). The mixture was stirred overnight at 25° C. and then concentrated. The residue was purified by flash chromatography on a Biotage Horizon, 65i column, eluting with 1 column volume of 10% ethyl acetate in hexanes followed by a gradient of 10 to 100% ethyl acetate in hexanes over 10 column volumes to provide the title compound (2.53 g, 72.2%). Mass spectrum (ESI) 537.0 (M+1). $^1$H NMR (500 MHz, CDCl$_3$): δ 8.29 (m, 2H), 7.94 (d, J=8.5 Hz 2H), 7.90 (m, 1H), 7.49 (s, 1H), 7.27-7.35 (m, 4H), 6.69

(m, 1H), 5.11 (s, 2H), 4.09-4.30 (m, 2H), 3.31-3.49 (m, 3H), 2.79 (m, 2H), 1.86 (m, 1H), 1.77 (m, 2H), 1.45 (d, J=6.5 Hz, 6H), 1.18-1.30 (m, 2H).

Intermediate 15

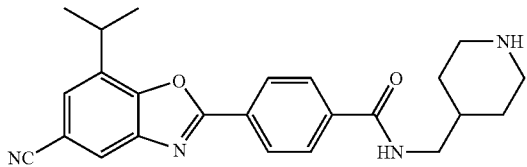

4-(5-Cyano-7-isopropyl-1,3-benzoxazol-2-yl)-N-(piperidin-4-ylmethyl)benzamide

To a solution of benzyl 4-({[4-(5-cyano-7-isopropyl-1,3-benzoxazol-2yl)benzoyl]amino}methyl)piperidine-1-carboxylate (2.19 g, EXAMPLE 35) in methanol (30 ml) and tetrahydrofuran (7 ml) was added 10% palladium on carbon (500 mg, 4.70 mmol). The mixture was flushed with nitrogen, then flushed with hydrogen, and then warmed to 50° C. and stirred for 3 h under a hydrogen balloon at this temperature, at which point LC/MS analysis showed no starting material. The mixture was filtered through a plug of Celite, washing liberally with methanol, and then concentrated to provide the title compound (1.7 g, 103%). Mass spectrum (ESI) 403.6 (M+1). $^1$H NMR (500 MHz, CDCl$_3$): δ 8.32 (d, J=8 Hz, 2H), 7.94 (d, J=8.5 Hz, 2H), 7.93 (s, 1H), 7.51 (s, 1H), 6.33 (br s, 1H), 3.44-3.54 (m, 2H), 3.40 (m, 2H), 3.13 (br d, 2H), 2.63 (br t, 2H), 1.77 (m, 2H), 1.46 (d, J=6.5 Hz, 6H), 1.26 (m, 2H).

Example 36

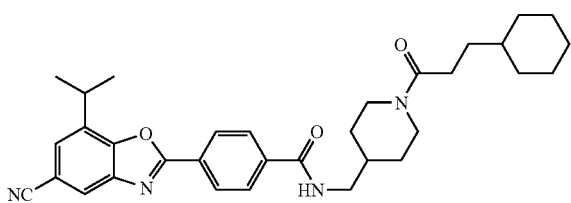

4-(5-Cyano-7-isopropyl-1,3-benzoxazol-2-yl)-N-{[1-(3-cyclohexylpropanoyl)piperidin-4-yl]methyl}benzamide To a solution of 4-(5-cyano-7-isopropyl-1,3-benzoxazol-2-yl)-N-(piperidin-4-ylmethyl)benzamide (20 mg, INTERMEDIATE 15) in 5 ml of dichloromethane was added 3-cyclohexylpropanoyl chloride (13 mg), and then diisopropylethylamine (450 μl). The reaction was stirred for 2 h at room temperature. The mixture was then diluted with 10 ml of ethyl acetate and 10 ml of water. The phases were separated and the aqueous phase was extracted with 10 ml of ethyl acetate. The combined organic phases were washed with 10 ml of brine, dried over Na$_2$SO$_4$, and concentrated. The residue was purified by reverse-phase HPLC on a Biotage Parallex Flex, Kromasil C18 21×100 mm column, eluting at 15 ml/min with 90% water (0.1% TFA) to 95% acetonitrile (0.1% TFA) over 10 min, hold for 2 min, then back to 90% water over 0.5 min, hold for 0.5 min, to provide the title compound (12 mg, 36%). Mass spectrum (ESI) 541.3 (M+1). $^1$H NMR signals are doubled and broadened because of restricted rotation about the amide C—N bond. $^1$H NMR (500 MHz, CDCl$_3$): δ 8.32 (d, J=8 Hz, 2H), 8.19 (s, 1H), 7.95 (d, J=8 Hz, 2H), 7.92 (d, J=1 Hz, 1H), 7.51 (s, 1H), 6.68-6.70 (m, 1H), 6.65 (m, 1H), 3.89-3.98 (m, 1H), 3.44-3.50 (m, 2H), 3.35 (m, 1H), 3.084 (m, 1H), 2.72 (s, 1H), 2.62 (m, 1H), 2.37-2.40 (m, 3H), 1.98 (m, 1H), 1.87 (m, 2H), 1.62-1.70 (m, 7H), 1.48 (m, 3H), 1.45 (d, J=7 Hz, 6H), 1.336 (d, H=7 Hz, 2H), 1.09-1.24 (m, 10H), 0.86-0.93 (m, 3H).

Example 37

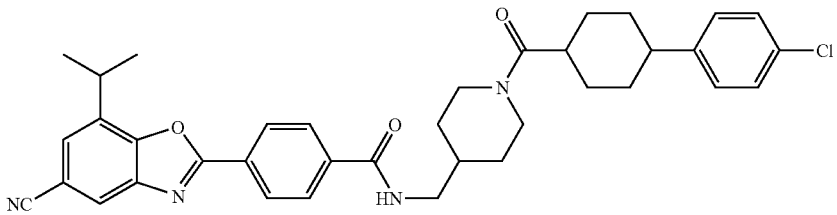

N-[(1-{[4-(4-chlorophenyl)cyclohexyl]carbonyl}piperidin-4-yl)methyl]-4-(5-cyano-7-isopropyl-1,3-benzoxazol-2-yl)benzamide To a solution of 4-(4-chlorophenyl)cyclohexanecarboxylic acid (40 mg) in dichloromethane at 0° C. was added oxalyl chloride (250 μl), and then dimethylformamide (50 μl). The reaction was warmed to room temperature and stirred for 2 h at this temperature. The solution was concentrated and then co-concentrated with toluene. The solid was redissolved in dichloromethane, and 4-(5-cyano-7-isopropyl-1,3-benzoxazol-2-yl)-N-(piperidin-4-ylmethyl)benzamide (20 mg, INTERMEDIATE 15) and diisopropylethylamine (100 □l) were added. The solution was stirred at room temperature for 4 h, and then was concentrated. The residue was purified by reverse-phase HPLC on a Biotage Parallex Flex, Kromasil C18 21×100 mm column, eluting at 15 ml/min with 90% water (0.1% TFA) to 95% acetonitrile (0.1% TFA) over 10 min, hold for 2 min, then back to 90% water over 0.5 min, hold for 0.5 min, to provide the title compound (10 mg, 22%). Mass spectrum (ESI) 623.3 (M+1). $^1$H NMR signals are doubled and broadened because of restricted rotation about the amide C—N bond. $^1$H NMR (500 MHz, CDCl3): δ 8.36 (d, J=8.5 Hz, 2H), 7.99 (d, J=8.5 Hz, 2H), 7.96 (app d, J=1.5 Hz, 1H), 7.55 (app d, J=1.5 Hz, 1H), 7.27-7.29 (m, 3H), 7.15 (m, 2H), 6.64 (app t, 1H), 6.38-6.43 (m, 3H), 4.71-4.74 (m, 1H), 4.05-4.07 (m, 1H), 3.48-3.58 (m, 2H), 3.38 (m, 1H), 3.145 (app tm 1H), 2.77 (s, 3H), 2.54-2.66 (m, 4H), 1.99-2.05

(m, 5H), 1.90 (m, 4H), 1.76 (m, 3H), 1.49 (d, J=7 Hz, 6H), 1.45-1.52 (m, 3H), 1.30 (m, 4H).

Example 38

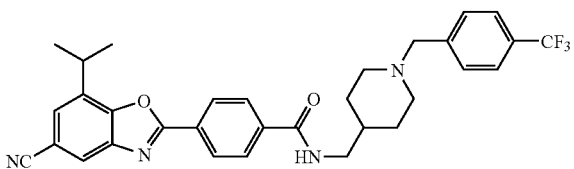

4-(5-Cyano-7-isopropyl-1,3-benzoxazol-2-yl)-N-({1-[4-(trifluoromethyl)benzyl]piperidin-4-yl}methyl)benzamide To a solution of 4-(5-cyano-7-isopropyl-1,3-benzoxazol-2-yl)-N-(piperidin-4-ylmethyl)benzamide (25 mg, INTERMEDIATE 15) in tetrahydrofuran (5 ml) was added sodium hydride (5 mg of a 60% dispersion in oil). The reaction was allowed to stir at room temperature for five min, and then 1-(bromomethyl)-4-(trifluoromethyl)benzene was added. The reaction was stirred for 1 h and then was concentrated. The residue was purified by reverse-phase HPLC on a Biotage Parallex Flex, Kromasil C18 21×100 mm column, eluting at 15 ml/min with 90% water (0.1% TFA) to 95% acetonitrile (0.1% TFA) over 10 min, hold for 2 min, then back to 90% water over 0.5 min, hold for 0.5 min, to provide the title compound (5 mg, 14.4%). Mass spectrum (ESI) 561.2 (M+1). $^1$H NMR (500 MHz, CDCl3): δ 8.31 (d, J=8.5 Hz, 2H), 7.92-7.94 (m, 3H), 7.55 (d, J=8 Hz, 2H), 7.50 (s, 1H), 7.42 (d, J=8 Hz, 2H), 6.37 (m, 1H), 3.54 (s, 2H), 3.44-3.51 (m, 2H), 3.40 (m, 2H), 2.89 (m, 2H), 1.98-2.03 (m, 2H), 1.83 (s, 1H) 1.74-1.77 (m, 2H), 1.67-1.71 (m, 1H), 1.45 (d, J=7 Hz, 6H), 1.36-1.40 (m, 2H), 1.25 (m, 1H).

Example 39

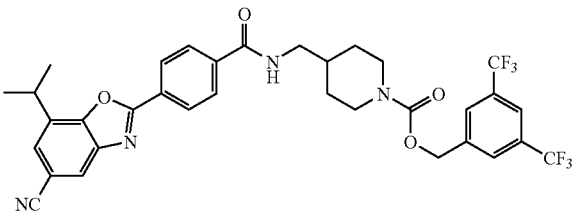

3,5-Bis(trifluoromethyl)benzyl 4-({[4-(5-cyano-7-isopropyl-1,3-benzoxazol-2-yl)benzoyl]amino}methyl)piperidine-1-carboxylate Step A. 4-Nitrobenzyl 4-({[4-(5-cyano-7-isopropyl-1,3-benzoxazol-2-yl)benzoyl]amino}methyl)piperidine-1-carboxylate The title compound was prepared using a procedure analogous to that described in EXAMPLE 37. Mass spectrum (ESI) 568.1 (M+1).

Step B. 3,5-Bis(trifluoromethyl)benzyl 4-({[4-(5-cyano-7-isopropyl-1,3-benzoxazol-2-yl)benzoyl]amino}methyl)piperidine-1-carboxylate To a solution of [3,5-bis(trifluoromethyl)phenyl]methanol (17 mg) in tetrahydrofuran (5 ml) was added sodium hydride (5 mg, 60% dispersion in mineral oil). The mixture was allowed to stir for 5 min, and then 4-nitrobenzyl 4-({[4-(5-cyano-7-isopropyl-1,3-benzoxazol-2-yl)benzoyl]amino}methyl)piperidine-1-carboxylate (20 mg) was added. The reaction mixture was stirred overnight at room temperature, and then was concentrated. The residue was purified by reverse-phase HPLC on a Biotage Parallex Flex, Kromasil C18 21×100 mm column, eluting at 15 mL/min with 90% water (0.1% TFA) to 95% acetonitrile (0.1% TFA) over 10 min, hold for 2 min, then back to 90% water over 0.5 min, hold for 0.5 min, to provide the title compound (5 mg, 21%). Mass spectrum (ESI) 673.1 (M+1). NMR signals are doubled and broadened because of restricted rotation about the amide C—N bond. $^1$H NMR (500 MHz, CDCl$_3$): δ 8.34 (d, J=8 Hz, 2H), 7.95 (m, 2H), 7.93 (s, 1H), 7.83 (s, 1H), 7.80 (s, 2H), 7.52 (s, 1H), 6.316 (app t, 1H), 5.23 (s, 2H), 4.23 (m, 2H), 2.82-2.90 (m, 2H), 1.89-1.93 (m, 1H), 1.83 (m, 3H), 1.73 (m, 3H), 1.46 (d, J=7 Hz, 6H), 1.21-1.31 (m, 4H).

Example 40

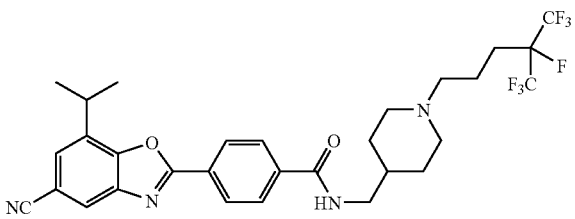

4-(5-Cyano-7-isopropyl-1,3-benzoxazol-2-yl)-N-({1-[4,5,5,5-tetrafluoro-4-(trifluoromethyl)pentyl]piperidin-4-yl}methyl)benzamide To a solution of 4,5,5,5-tetrafluoro-4-trifluoromethyl-1-pentanol (500 mg, 2.192 mmol) in dichloromethane (2 ml) were added ca. 20 mg of crushed 4-Å molecular sieves, N-morpholine-N-oxide (385 mg, 3.29 mmol) and tetra-N-propylammonium perruthenate (VII) (38.5 mg, 0.110 mmol). The mixture was stirred for 1 h at room temperature and then filtered through a Biotage Horizon 25S column eluting with 5 column volumes of 100% CH$_2$Cl$_2$. The filtrate was concentrated to provide the desired crude aldehyde. To a solution of this aldehyde in methanol (2 ml) were added 4-(5-cyano-7-isopropyl-1,3-benzoxazol-2-yl)-N-(piperidin-4-ylmethyl)benzamide (30 mg, 0.075 mmol, INTERMEDIATE 15) and sodium cyanoborohydride (50 mg, 0.796 mmol). The mixture was stirred for 3 h at room temperature, at which point LC/MS analysis showed a new peak at the desired molecular weight, as well as a peak at M-2 (imine). Stirring was continued over the weekend. The reaction mixture was then diluted with saturated sodium bicarbonate solution (10 ml) and ethyl acetate (10 ml). The phases were separated and the aqueous phase was extracted with ethyl acetate (2×10 ml). The combined organics were washed with 10 ml of brine, dried (sodium sulfate), and concentrated. The residue was purified by flash chromatography on a Biotage Horizon, 25S column, eluting with 1 column volume of 100% dichloromethane followed by a gradient of 0 to 50% methanol in dichloromethane over 10 column volumes. The resulting product was repurified by preparative thin-layer chromatography, eluting with 5% methanol in dichloromethane, to provide the title compound (26 mg, 0.042 mmol, 56.9% yield). Mass spectrum (ESI) 613.6 (M+1). $^1$H NMR (500 MHz, CDCl3): δ 8.30 (d, J=8.5 Hz, 2H), 7.94 (d, J=8.5 Hz, 2H), 7.91 (d, J=1.5 Hz, 1H), 7.50 (s, 1H), 6.47 (br s, 1H), 3.40-3.50 (m, 2H), 3.40 (t, J=6.5 Hz, 2H), 2.93 (br d, J=11.5 Hz, 2H), 2.39 (t, J=7.0 Hz, 2H), 2.12 (m, 2H), 1.99 (br t, J=11.0 Hz, 2H), 1.64-1.80 (m, 5H), 1.45 (d, J=7.0 Hz, 6H), 1.34-1.46 (m, 2H).

Example 41

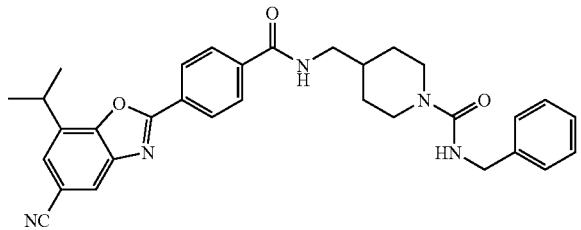

N-Benzyl-4-({[4-(5-cyano-7-isopropyl-1,3-benzoxazol-2-yl)benzoyl]amino}methyl)piperidine-1-carboxamide To a solution of 4-(5-cyano-7-isopropyl-1,3-benzoxazol-2-yl)-N-(piperidin-4-ylmethyl)benzamide (30 mg, 0.075 mmol, INTERMEDIATE 15) in dichloromethane (1 ml) was added benzyl isocyanate (10 µl 0.081 mmol). The mixture was stirred for 2 h at room temperature, at which point LC/MS analysis showed a new peak at the desired molecular weight. The reaction mixture was purified by flash chromatography on a Biotage Horizon, 25S column, eluting with 1 column volume of 100% dichloromethane followed by a gradient of 0 to 100% ethyl acetate in dichloromethane over 10 column volumes. The resulting mixture was repurified by reverse-phase HPLC: Kromasil C18 21×100 mm column, eluting at 15 ml/min with 90% water (0.1% TFA) to 95% acetonitrile (0.1% TFA) over 10 min, hold for 2 min, then back to 90% water over 0.5 min, hold for 0.5 min, to provide the title compound (7.9 mg, 0.015 mmol, 19.79% yield). Mass spectrum (ESI) 536.1 (M+1). $^1$H NMR (500 MHz, CDCl3): δ 8.32 (d, J=7.0 Hz, 2H), 7.94 (d, J=7.0 Hz, 2H), 7.93 (d, J=1.5 Hz, 1H), 7.52 (s, 1H), 7.27-7.35 (m, 4H), 6.55 (br s, 1H), 4.43 (s, 2H), 3.99 (br d, J=11.0 Hz, 2H), 3.47 (septet, J=5.5 Hz, 1H), 3.42 (t, J=5.5 Hz, 2H), 2.86 (br t, J=10.5 Hz, 2H), 2.73 (s, 3H), 1.90 (m, 1H), 1.81 (br d, J=10.0 Hz, 2H), 1.46 (d, J=5.5 Hz, 6H), 1.31 (m, 2H).

Example 42

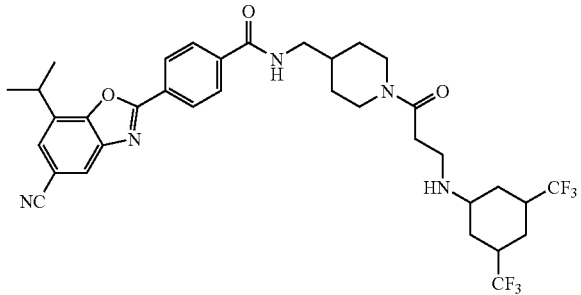

N-[(1-{N-[3,5-Bis(trifluoromethyl)cyclohexyl]-β-alanyl}piperidin-4-yl)methyl]-4-(5-cyano-7-isopropyl-1,3-benzoxazol-2-yl)benzamide Step A. Benzyl {3-[4-({[4-(5-cyano-7-isopropyl-1,3-benzoxazol-2-yl)benzoyl]amino}methyl)piperidin-1-yl]-3-oxopropyl}carbamate To a suspension of N-carbobenzoxy-β-alanine (20 mg, 0.090 mmol) in dichloromethane (2 ml) were added o-benzotriazol-1-yl-tetramethyluronium hexafluorophosphate (65 mg, 0.171 mmol), 1-hydroxybenzotriazole (15 mg, 0.111 mmol), and diisopropylethylamine (0.040 ml, 0.229 mmol). After 5 min, 4-(5-cyano-7-isopropyl-1,3-benzoxazol-2-yl)-N-(piperidin-4-ylmethyl)benzamide (30 mg, 0.075 mmol, INTERMEDIATE 15) was added and the mixture was stirred overnight at 25° C. The mixture was diluted with saturated sodium bicarbonate solution (10 ml) and dichloromethane (10 ml). The phases were separated and the aqueous phase was extracted with dichloromethane (2×10 ml). The combined organics were washed with 10 ml of brine, dried (sodium sulfate), and concentrated. The residue was purified by flash chromatography on a Biotage Horizon, 25S column, eluting with 1 column volume of 100% dichloromethane followed by a gradient of 0 to 50% methanol in dichloromethane over 10 column volumes. The resulting mixture was repurified by preparative thin-layer chromatography, eluting with 5% methanol in dichloromethane provide the title compound (24.8 mg, 0.041 mmol, 54.8% yield). Mass spectrum (ESI) 630.1 (M+1).

Step B. N-[(1-{N-[3,5-Bis(trifluoromethyl)cyclohexyl]-β-alanyl}piperidin-4-yl)methyl]-4-(5-cyano-7-isopropyl-1,3-benzoxazol-2-yl)benzamide The title compound was prepared from deprotected benzyl {3-[4-({[4-(5-cyano-7-isopropyl-1,3-benzoxazol-2-yl)benzoyl]amino}methyl)piperidin-1-yl]-3-oxopropyl}carbamate using a procedure analogous to that described in EXAMPLE 40.

Two diastereomers were isolated.

Diastereomer A: Mass spectrum (ESI) 691.9 (M+1). $^1$H NMR (500 MHz, CDCl3): δ 8.34 (d, J=8.0 Hz, 2H), 7.95 (d, J=8.5 Hz, 2H), 7.94 (s, 1H), 7.52 (s, 1H), 6.36 (br t, J=6.0 Hz, 1H), 4.66 (m, 1H), 3.89 (m, 1H), 3.48 (m, 2H), 3.36 (m, 1H), 3.22 (br s, 1H), 3.04 (br t, J=13.0 Hz, 1H), 2.76-2.86 (m, 2H), 2.46-2.50 (m, 4H), 2.10 (br d, J=12.5 Hz, 1H), 1.80-2.15 (m, 4H), 1.46 (d, J=7.0 Hz, 6H), 1.16-1.50 (m, 5H).

Diastereomer B: Mass spectrum (ESI) 692.2 (M+1). $^1$H NMR (500 MHz, CDCl$_3$): δ 8.34 (d, J=8.5 Hz, 2H), 7.94 (d, J=8.5 Hz, 2H), 7.94 (d, J=1.5 Hz, 1H), 7.52 (d, J=1.0 Hz, 1H), 6.34 (br t, J=6.5 Hz, 1H), 4.65 (br d, J=13.5 Hz, 1H), 3.88 (br d, J=13.5 Hz, 1H), 3.48 (m, 2H), 3.36 (m, 1H), 3.03 (br t, J=12.5 Hz, 1H), 2.93 (t, J=16.0 Hz, 2H), 2.50-2.64 (m, 4H), 2.10-2.26 (m, 4H), 1.95 (m, 1H), 1.85 (br t, J=12.5 Hz, 2H), 1.46 (d, J=7.0 Hz, 6H), 1.09-1.36 (m, 4H).

Following the procedures described in EXAMPLES 36-42 the compounds listed in Table 5 were prepared. The symbol "X1" on each substituent group shows the point of attachment of the substituent group to the structure at the top of the table.

TABLE 5
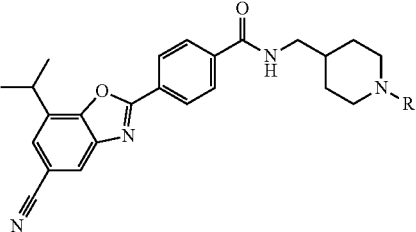
| EXAMPLE | R | MS (M + 1) |
|---|---|---|
| 43 | 3,5-bis(trifluoromethyl)benzoyl | 643.1 |
| 44 | 3,3-dimethylbutanoyl | 501.2 |
| 45 | 2-phenylbutanoyl | 549.3 |
| 46 | 4-phenylbutanoyl | 549.2 |
| 47 | 2-phenylcyclopropanecarbonyl | 547.2 |
| 48 | [3,5-bis(trifluoromethyl)phenyl]acetyl | 657.1 |
| 49 | 4-cyclohexylbutanoyl | 549.2 |
| 50 | nonanoyl | 543.3 |
| 51 | 3-cyclohexylpropyl | 527.3 |
| 52 | 3,5-bis(trifluoromethyl)phenylsulfonyl | 680.3 |

TABLE 5-continued

[Structure: isopropyl-cyano-benzoxazole-benzamide-CH2-piperidine-N-R]

| EXAMPLE | R | MS (M + 1) |
|---------|---|------------|
| 53 | X₁–SO₂–CH₂CH₂CH₂–phenyl | 585.1 |
| 54 | X₁–C(O)–CH=CH–phenyl | 533.2 |
| 55 | X₁–SO₂–(4-butylphenyl) | 599.3 |
| 56 | X₁–C(O)–CH₂CH₂–(3,5-bis(trifluoromethyl)phenyl) | 671.1 |
| 57 | X₁–CH₂–(2-trifluoromethylphenyl) | 561.4 |
| 58 | X₁–CH₂–(3-trifluoromethylphenyl) | 561.2 |
| 59 | X₁–CH₂–(3-chlorophenyl) | 528.5 |
| 60 | X₁–CH₂–(3-cyanophenyl) | 518.2 (M+) |
| 61 | X₁–(6-methoxypyridin-2-yl) | 510.2 |
| 62 | X₁–(4,6-dimethylpyrimidin-2-yl) | 509.2 |
| 63 | X₁–(trans-4-trifluoromethylcyclohexyl) | 553.2 |
| 64 | X₁–(3-trifluoromethylcyclohexyl) | 553.2 |

Example 65

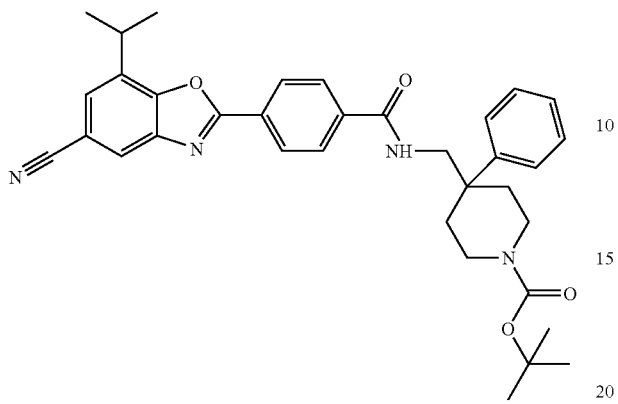

tert-Butyl 4-({[4-(5-cyano-7-isopropyl-1,3-benzoxazol-2-yl)benzoyl]amino}methyl)-4-phenylpiperidine-1-carboxylate The title compound was prepared from 4-(5-cyano-7-isopropyl-1,3-benzoxazol-2-yl)-N-(piperidin-4-ylmethyl)benzamide (30 mg, 0.075 mmol, INTERMEDIATE 15) as described in Example 35. Mass spectrum (ESI) 479.2 (M-Boc).

Example 66

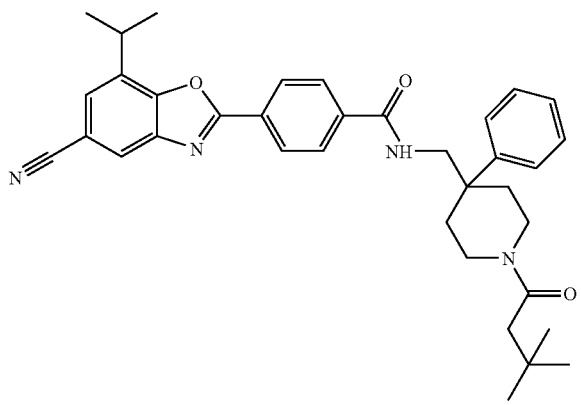 [SMILES: CC(C)c1cc(C#N)cc2nc(-c3ccc(C(=O)NCC4(c5ccccc5)CCN(C(=O)CC(C)(C)C)CC4)cc3)oc12]

4-(5-Cyano-7-isopropyl-1,3-benzoxazol-2-yl)-N-{[1-(3,3-dimethylbutanoyl)-4-phenylpiperidin-4-yl]methyl}benzamide To a solution of tert-butyl 4-({[4-(5-cyano-7-isopropyl-1,3-benzoxazol-2-yl)benzoyl]amino}methyl)-4-phenylpiperidine-1-carboxylate (30 mg, EXAMPLE 65) in dichloromethane was added trifluoroacetic acid. The mixture was stirred for 1 h at room temperature and then concentrated. The residue was redissolved in dichloromethane and 3,3-dimethylbutanoyl chloride (12 mg) and diisopropylethylamine (100 µl) were added. The mixture was stirred overnight at room temperature and then concentrated. The residue was purified by mass-directed reverse-phase HPLC on a Sunfire 19×100 mm column, eluting at 40 ml/min with 90% water (0.1% formic acid) to 100% acetonitrile (0.1% formic acid) over 6 min, to provide the title compound (20 mg, 83%). Mass spectrum (ESI) 577.4 (M+1). NMR signals are doubled and broadened because of restricted rotation about the amide C—N bond. $^1$H NMR (500 MHz, CDCl$_3$): 8.28 (d, J=8 Hz, 2H), 7.93 (d, J=1.5 Hz, 1H), 7.74 (d, J=8.5 Hz, 2H), 7.47-7.51 (m, 3H), 7.31-7.40 (m, 3H), 5.80 (m, 1H), 4.02-4.06 (m, 1H), 3.86-3.89 (m, 1H), 3.80-3.83 (m, 1H), 3.62-3.66 (m, 1H), 3.43-3.51 (m, 3H), 2.27-2.30 (m, 2H), 1.98-2.04 (m, 2H), 1.56-1.62 (m, 1H), 1.45 (d, J=7.5 Hz, 6H).

Example 67

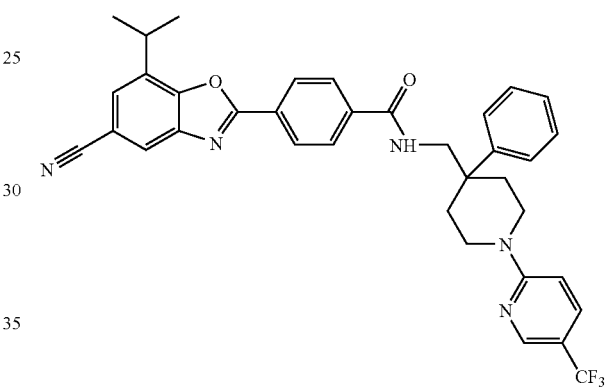

4-(5-Cyano-7-isopropyl-1,3-benzoxazol-2-yl)-N-({4-phenyl-1-[5-(trifluoromethyl)pyridin-2-yl]piperidin-4-yl}methyl)benzamide To a solution of 4-(5-cyano-7-isopropyl-1,3-benzoxazol-2-yl)benzoic acid (25 mg, INTERMEDIATE 2) in dichloromethane (5 ml) at 0° C. was added oxalyl chloride (200 □l), and then dimethylformamide (50 µl). The reaction was allowed to warm to room temperature and then stirred for 2 h. The solution was concentrated and then co-concentrated with toluene. The solid was redissolved in dichloromethane, and then ({4-phenyl-1-[5-(trifluoromethyl)pyridin-2-yl]piperidin-4-yl}methyl)amine (50 mg) was added. The reaction stirred at room temperature for 4 h, and then was concentrated. The residue was purified by mass-directed reverse-phase HPLC on a Sunfire 19×100 mm column, eluting at 40 ml/min with 90% water (0.1% formic acid) to 100% acetonitrile (0.1% formic acid) over 6 min, to provide the title compound (20 mg, 34%). Mass spectrum (ESI) 622.4 (M+1). $^1$H NMR (500 MHz, CDCl$_3$): 8.25 (m, 1H), 8.16 (d, J=8.5 Hz, 2H), 7.81 (d, J=1.5 Hz, 1H), 7.70 (d, J=8.5 Hz, 2H), 7.47-2.49 (app dd, 1H), 7.40 (d, J=1 Hz, 1H), 7.35-7.36 (m, 4H), 7.21-7.24 (m, 1H), 6.55 (d, J=9 Hz, 1H), 6.36-6.39 (m, 1H), 3.89-3.94 (m, 2H), 3.60 (d, J=6.5 Hz, 2H), 3.31-3.39 (m, 3H), 2.20-2.23 (m, 2H), 1.91-1.96 (m, 2H), 1.35 (d, J=7 Hz, 6H).

Example 68

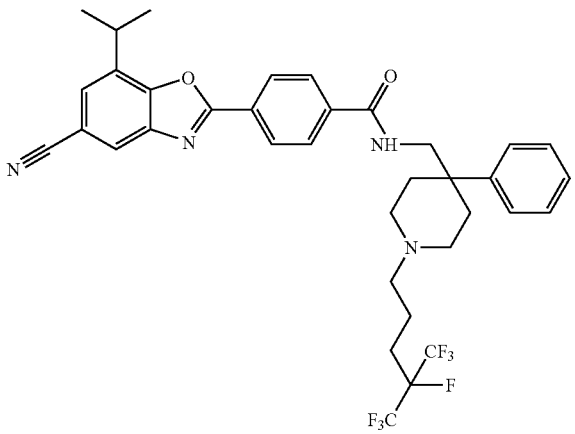 [SMILES: CC(C)c1cc(C#N)cc2nc(-c3ccc(C(=O)NCC4(c5ccccc5)CCN(CCCC(F)(C(F)(F)F)C(F)(F)F)CC4)cc3)oc12]

4-(5-Cyano-7-isopropyl-1,3-benzoxazol-2-yl)-N-({4-phenyl-1-[4,5,5,5-tetrafluoro-4-(trifluoromethyl)pentyl]piperidin-4-yl}methyl)benzamide The title compound was prepared from tert-butyl 4-({[4-(5-cyano-7-isopropyl-1,3-benzoxazol-2-yl)benzoyl]amino}methyl)-4-phenylpiperidine-1-carboxylate (30 mg, EXAMPLE 65) as described in EXAMPLE 40. Mass spectrum (ESI) 689.5 (M+1). $^1$H NMR (500 MHz, CDCl$_3$): δ 8.33 (s, 1H), 8.27 (d, J=, 2H), 7.92 (d, J=1 Hz, 1H), 7.80 (d, J=8.5 Hz, 2H), 7.50 (m, 1H), 7.45-7.48 (m, 2H), 7.33-7.39 (m, 3H), 6.17 (m, 1H), 4.21-4.41 (m, 4H), 3.69 (d, J=6 Hz, 2H), 3.43-3.49 (m, 1H), 3.09 (m, 2H), 2.28-2.37 (m, 4H), 2.09-2.16 (m, 2H), 1.89-1.95 (m, 2H), 1.44 (d, J=7 Hz, 6H).

Example 69

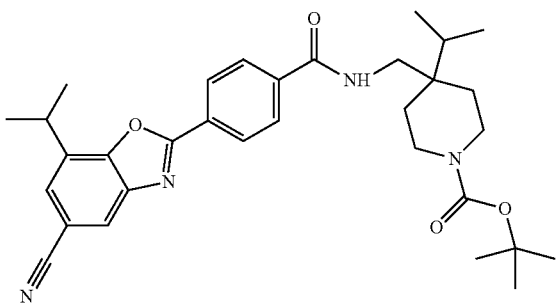 [SMILES: CC(C)c1cc(C#N)cc2nc(-c3ccc(C(=O)NCC4(C(C)C)CCN(C(=O)OC(C)(C)C)CC4)cc3)oc12]

tert-Butyl 4-({[4-(5-cyano-7-isopropyl-1,3-benzoxazol-2-yl)benzoyl]amino}methyl)-4-isopropylpiperidine-1-carboxylate

Step A. tert-Butyl 4-(aminocarbonyl)-4-isopropylpiperidine-1-carboxylate

To a solution of 1-(tert-butoxycarbonyl)-4-isopropylpiperidine-4-carboxylic acid (500 mg, 1.843 mmol) in dichloromethane (5 ml) were added oxalyl chloride (2.76 ml, 5.53 mmol) and a drop (ca. 10 µl) of dimethylformamide. After stirring 1 h at room temperature, the mixture was concentrated and then dissolved in tetrahydrofuran (5 ml). Concentrated ammonium hydroxide (5 ml, 36.0 mmol) was added and the mixture was stirred overnight at room temperature, and then concentrated to a small volume, poured into 50 ml of 1 M NaOH, and diluted with 50 ml of ethyl acetate. The phases were separated, the aqueous was extracted with 2×25 ml of ethyl acetate, and then the combined organics were washed with 25 ml of brine, dried (Na$_2$SO$_4$), and concentrated to provide the title compound (411 mg, 1.520 mmol, 82% yield). Mass spectrum (ESI) 174.0 (M-Boc).

Step B. tert-Butyl 4-cyano-4-isopropylpiperidine-1-carboxylate

To a solution of tert-butyl 4-(aminocarbonyl)-4-isopropylpiperidine-1-carboxylate (100 mg, 0.370 mmol) in dimethylformamide (2 ml) was added cyanuric chloride (34.1 mg, 0.185 mmol). After stirring over the weekend at room temperature, the mixture was diluted with 10 ml of water, and 20 ml of ethyl acetate. The phases were separated and the aqueous phase was extracted with ethyl acetate (2×15 ml). The combined organics were washed with 10 ml each of saturated sodium bicarbonate solution and brine, dried (sodium sulfate), and then concentrated to provide the title compound (93 mg, 0.369 mmol, 100% yield). Mass spectrum (ESI) 153.2.0 (M-Boc).

Step C. tert-Butyl 4-({[4-(5-cyano-7-isopropyl-1,3-benzoxazol-2-yl)benzoyl]amino}methyl)-4-isopropylpiperidine-1-carboxylate To a solution of tert-butyl 4-cyano-4-isopropylpiperidine-1-carboxylate (90 mg, 0.357 mmol) in ammonium hydroxide (2 ml) and ethanol (4 ml) was added Raney nickel (100 mg, 1.167 mmol). The mixture was flushed with nitrogen, then flushed with hydrogen and stirred overnight under a hydrogen balloon, at which point LC/MS analysis showed the desired product. The mixture was filtered through a plug of Celite, washing liberally with methanol, and then concentrated to a small volume and partitioned between 20 ml of 1 N sodium hydroxide and 25 ml of ethyl acetate. The aqueous phase was extracted with 2×20 ml of ethyl acetate, and then the combined organics were washed with brine, dried (sodium sulfate), and concentrated. The residue was purified by flash chromatography on a Biotage Horizon, 25M column, eluting with 1 column volume of 100% dichloromethane followed by a gradient of 0 to 50% methanol in dichloromethane over 10 column volumes to provide tert-butyl 4-(aminomethyl)-4-isopropylpiperidine-1-carboxylate (48 mg). The title compound was then prepared from tert-butyl 4-(aminomethyl)-4-isopropylpiperidine-1-carboxylate (48 mg) and 4-(5-cyano-7-isopropyl-1,3-benzoxazol-2-yl)benzoic acid (57 mg, INTERMEDIATE 2) as described in EXAMPLE 35. Mass spectrum (ESI) 545.3 (M+1). $^1$H NMR (500 MHz, CDCl$_3$): 8.33 (d, J=8.0 Hz, 1H), 7.94 (s, 1H), 7.92 (d, J=8.5 Hz, 2H), 7.51 (s, 1H), 6.14 (br t, J=6.0 Hz, 1H), 3.63 (m, 4H), 3.47 (septet, J=7.0 Hz, 1H), 3.33 (br t, J=10.5 Hz, 2H), 1.83 (septet, J=7.0 Hz, 1H), 1.54-1.66 (m, 4H), 1.46 (d, J=7.0 Hz, 6H), 1.45 (s, 9H), 0.99 (d, J=7.0 Hz, 6H).

Example 70

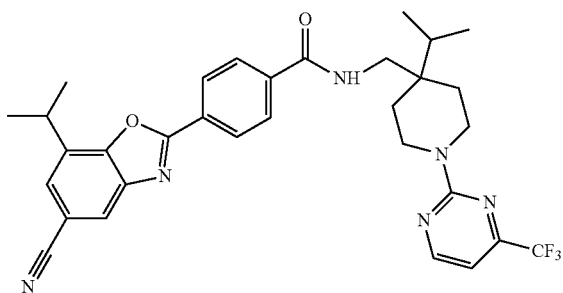 [SMILES: CC(C)c1cc(C#N)cc2nc(-c3ccc(C(=O)NCC4(C(C)C)CCN(c5nccc(C(F)(F)F)n5)CC4)cc3)oc12]

4-(5-cyano-7-isopropyl-1,3-benzoxazol-2-yl)-N-({4-isopropyl-1-[4-(trifluoromethyl)pyrimidin-2-yl]piperidin-4-yl}methyl)benzamide To a solution of tert-butyl 4-({[4-(5-cyano-7-isopropyl-1,3-benzoxazol-2-yl)benzoyl]amino}methyl)-4-isopropylpiperidine-1-carboxylate (35 mg, 0.064 mmol) in dichloromethane was added trifluoroacetic acid. The mixture was stirred overnight at room temperature and then concentrated in vacuo. To the residue were added of methanol (2 ml), potassium carbonate (45 mg, 0.326 mmol) and 2-chloro-4-(trifluoromethyl)pyrimidine (16 μl, 0.133 mmol). The mixture was heated to 50° C. and stirred at this temperature for 4 h, at which point LC/MS analysis showed a peak at the desired molecular weight. The reaction mixture was concentrated and then purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (33 mg, 0.056 mmol, 87% yield). Mass spectrum (ESI) 591.1 (M+1). $^1$H NMR (500 MHz, CDCl$_3$): 8.47 (d, J=4.5 Hz, 1H), 8.33 (d, J=8.5 Hz, 1H), 7.93 (s, 1H), 7.92 (d, J=8.5 Hz, 2H), 7.51 (s, 1H), 6.71 (d, J=5.0 Hz, 1H), 6.18 (br t, J=6.0 Hz, 1H), 4.18 (m, 2H), 3.65-3.75 (m, 4H), 3.47 (septet, J=7.0 Hz, 1H), 1.89 (septet, J=6.5 Hz, 1H), 1.70 (m, 2H), 1.50-1.60 (m, 2H), 1.46 (d, J=6.5 Hz, 6H), 1.02 (d, J=7.0 Hz, 6H).

Following the procedures described in EXAMPLES 65-70, the compounds listed in Table 6 were prepared. The symbol "X1" on each substituent group shows the point of attachment of the substituent group to the structure at the top of the table.

TABLE 6

| EXAMPLE | R | MS (M+1) |
|---|---|---|
| 71 | (4-phenyl-1-methylpiperidin-4-yl)methyl | 493.2 |
| 72 | {4-phenyl-1-[4-(trifluoromethyl)pyrimidin-2-yl]piperidin-4-yl}methyl | 625.4 |
| 73 | [1-(benzyloxycarbonyl)-4-phenylpiperidin-4-yl]methyl | 613.3 |
| 74 | [1-(methoxycarbonyl)-4-phenylpiperidin-4-yl]methyl | 537.3 |
| 75 | (1-acetyl-4-phenylpiperidin-4-yl)methyl | 521.3 |

TABLE 6-continued

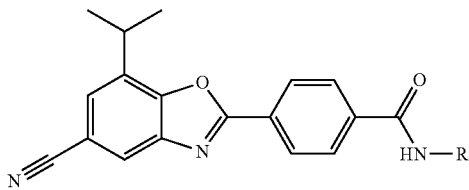

| EX-AMPLE | R | MS (M + 1) |
|---|---|---|
| 76 | 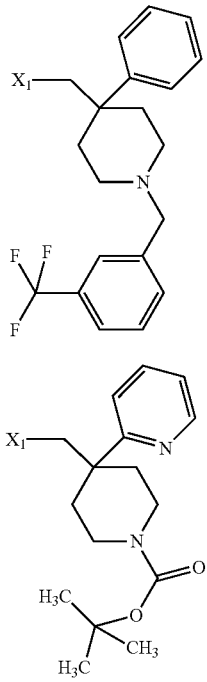 | 637.1 |
| 77 | 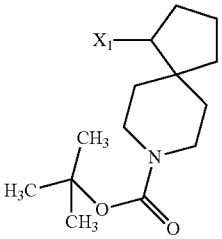 | 580.3 |
| 78 | 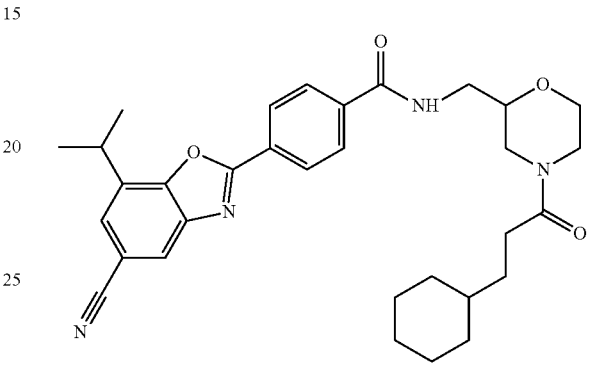 | 443.2 (M-Boc) |

Intermediate 16

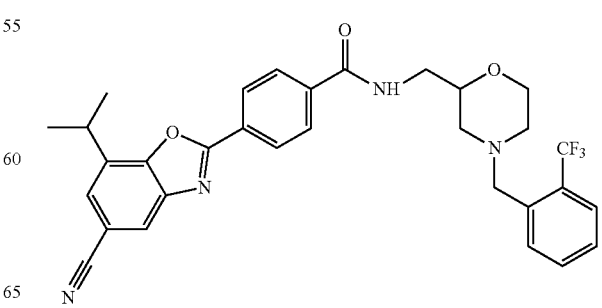

tert-Butyl 2-({[4-(5-cyano-7-isopropyl-1,3-benzoxazol-2-yl)benzoyl]amino}methyl)morpholine-4-carboxylate The title compound was then prepared from tert-butyl 2-(aminomethyl)morpholine-4-carboxylate (48 mg) and 4-(5-cyano-7-isopropyl-1,3-benzoxazol-2-yl)benzoic acid, INTERMEDIATE 2) as described in EXAMPLE 35. Mass spectrum (ESI) 505.3 (M+1).

Example 79

4-(5-Cyano-7-isopropyl-1,3-benzoxazol-2-yl)-N-{[4-(3-cyclohexylpropanoyl)morpholin-2-yl]methyl}benzamide The title compound was prepared from tert-butyl 2-({[4-(5-cyano-7-isopropyl-1,3-benzoxazol-2-yl)benzoyl]amino}methyl)morpholine-4-carboxylate (INTERMEDIATE 15) using the procedure described in EXAMPLE 36. Mass spectrum (ESI) 543.3 (M+1). $^1$H NMR signals are doubled and broadened because of restricted rotation about the amide C—N bond. NMR (500 MHz, CDCl3): 8.31-8.35 (m, 2H), 7.94-7.98 (m, 3H), 7.51 (s, 1H), 6.67-6.73 (m, 1H), 4.89-518 (bs, 1H), 4.44-4.54 (m, 1H), 3.97-3.99 (m, 1H), 3.83-3.86 (m, 1H), 3.77-3.79 (m, 1H), 3.61-3.68 (m, 1H), 3.55-3.58 (m, 1H), 3.44-3.50 (m, 2H), 3.01-3.32 (m, 1H), 2.33-2.38 (m, 2H), 1.63-1.71 (m, 6H), 1.49-1.53 (m, 2H), 1.45 (d, J=7 Hz, 6H), 1.12-1.27 (m, 5H), 0.87-0.94 (m, 2H).

Example 80

4-(5-Cyano-7-isopropyl-1,3-benzoxazol-2-yl)-N-({4-[2-(trifluoromethyl)benzyl]morpholin-2-yl}methyl)benzamide The title compound was prepared from deprotected tert-butyl 2-({[4-(5-cyano-7-isopropyl-1,3-benzoxazol-2-yl)benzoyl]amino}methyl)morpholine-4-carboxylate (INTERMEDIATE 15) using the procedure described in EXAMPLE 38. Mass spectrum (ESI) 563.3 (M+1). $^1$H NMR (500 MHz, CDCl$_3$): δ 8.33 (d, J=8 Hz, 2H), 7.96 (d, H=8 Hz, 2H), 7.93 (d, J=1 Hz, 1H), 7.76 (d, H=8 Hz, 1H), 7.63 (d, J=7.5 Hz, 1H), 7.51-7.53 (m, 2H), 7.34-7.36 (m, 1H), 6.64-6.66 (m, 1H), 3.89-3.92 (m, 1H), 3.74-3.81 (m, 2H), 3.70-3.72 (m, 1H), 3.67 (m, 2H), 3.45-3.50 (m, 1H), 3.33-3.38 (m, 1H), 2.79 (d, J=11.5 Hz, 1H), 2.66 (d, J=11.5 Hz, 1H), 2.26-2.31 (m, 1H), 2.05-2.10 (m, 1H), 1.66 (s, 1H), 1.46 (d, H=7 Hz, 6H).

Intermediate 17

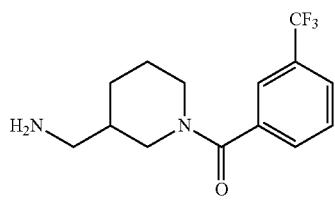 [SMILES: NCC1CCCN(C(=O)c2cccc(C(F)(F)F)c2)C1]

1-{1-[3-(Trifluoromethyl)benzoyl]piperidin-3-yl}methanamine

To a solution of the tert-butyl(piperidin-3-ylmethyl)carbamate (429 mg) in 10 ml dichloromethane was added triethylamine (558 μl) followed by 417 mg of 3-(trifluoromethyl)benzoyl chloride. The mixture was stirred at room temperature for 1 h, and then concentrated in vacuo. The residue was filtered through a plug of silica gel (eluting with ethyl acetate) to provide tert-butyl({1-[3-(trifluoromethyl)benzoyl]piperidin-3-yl}methyl)carbamate (665 mg, 86%). To a solution of this in 10 ml of dichloromethane was added trifluoroacetic acid (10 ml). The mixture was stirred at 60° C. for 1 h, and then concentrated in vacuo. The residue was diluted with 30 ml of ethyl acetate and basified by slow and cautious addition of 30 ml of a saturated aqueous solution of sodium bicarbonate. The aqueous layer was separated and extracted once with 30 ml of ethyl acetate. The combined organic layers were dried over sodium sulfate, filtered, and concentrated in vacuo to provide the title compound (401 mg, 82%). Mass spectrum (ESI) 287.3 (M+1).

Intermediate 18

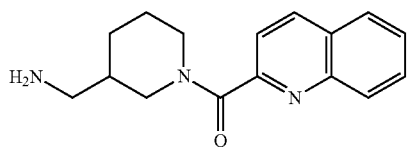 [SMILES: NCC1CCCN(C(=O)c2ccc3ccccc3n2)C1]

1-[1-(Quinolin-2-ylcarbonyl)piperidin-3-yl]methanamine

The title compound was prepared using a procedure analogous to that described in INTERMEDIATE 17. Mass spectrum (ESI) 270.2 (M+1).

Intermediate 19

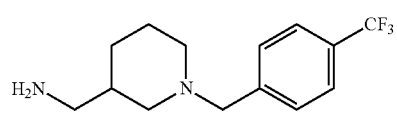 [SMILES: NCC1CCCN(Cc2ccc(C(F)(F)F)cc2)C1]

1-{1-[4-(Trifluoromethyl)benzyl]piperidin-3-yl}methanamine

To a mixture of 830 mg of potassium carbonate in 50 ml of methanol was added tert-butyl(piperidin-3-ylmethyl)carbamate (643 mg), followed by 1-(bromomethyl)-4-(trifluoromethyl)benzene (717 mg). The mixture was heated to 70° C. and stirred for 0.5 h. The sample was filtered through a small plug of silica gel and concentrated in vacuo to provide tert-butyl({1-[4-(trifluoromethyl)benzyl]piperidin-3-yl}methyl)carbamate (640 mg). To a solution of this protected amine in 10 ml of dichloromethane was added trifluoroacetic acid (5 ml). The mixture was stirred at 70° C. for 1.5 h, and then concentrated in vacuo. The residue was diluted with 30 ml of ethyl acetate and basified by slow and cautious addition of 30 ml of a saturated aqueous solution of sodium bicarbonate. The aqueous layer was separated and extracted once with 30 ml of ethyl acetate. The combined organic layers were dried over sodium sulfate, filtered, and concentrated in vacuo to provide the title compound (418 mg, 89%). Mass spectrum (ESI) 273.2 (M+1).

Example 81

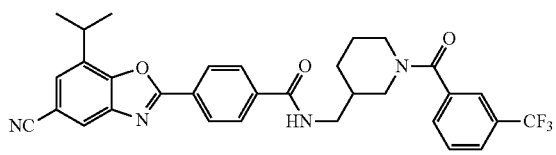 [SMILES: CC(C)c1cc(C#N)cc2nc(-c3ccc(C(=O)NCC4CCCN(C(=O)c5cccc(C(F)(F)F)c5)C4)cc3)oc12]

4-(5-cyano-7-isopropyl-1,3-benzoxazol-2-yl)-N-({1-[3-(trifluoromethyl)benzoyl]piperidin-3-yl}methyl)benzamide The title compound was prepared using a procedure analogous to that described in EXAMPLE 1. Mass spectrum (ESI) 575.2 (M+1). $^1$H NMR (500 MHz, CDCl$_3$): δ 8.32 (d, J=7.5 Hz, 2H), 8.08 (d, J=7.4 Hz, 2H), 7.92 (s, 1H), 7.70 (s, 1H), 7.58 (m, 3H), 7.50 (s, 1H), 6.31 (t, J=5.9 Hz, 1H), 3.87 (m, 2H), 3.69 (dd, J=13.3, 2.3 Hz, 2H), 3.43 (m, 5H), 2.19 (m, 1H), 1.93 (m, 2H), 1.45 (d, J=7.1 Hz, 3H).

Following the procedures described in EXAMPLES 35, and 79-81, the compounds listed in Table 7 were prepared. The symbol "X1" on each substituent group shows the point of attachment of the substituent group to the structure at the top of the table.

TABLE 7

| EXAMPLE | R | MS (M + 1) |
|---|---|---|
| 82 | X₁—CH₂-(4-phenyl-morpholin-2-yl) | 482.2 |
| 83 | X₁—CH₂-(4-benzyl-morpholin-2-yl) | 495.3 |
| 84 | X₁—CH₂-(4-benzyl-5-methyl-morpholin-2-yl) | 509.2 |
| 85 | X₁—CH₂-(4-benzyl-5-methyl-morpholin-2-yl) | 509.3 |
| 86 | X₁—CH₂-(4-benzyloxycarbonyl-morpholin-2-yl) | 539.2 |
| 87 | X₁—CH₂-(4-(2-(naphthalen-2-yl)-2-oxoethyl)-morpholin-2-yl) | 573.3 |
| 88 | X₁—CH₂-(4-phenethyl-morpholin-2-yl) | 509.3 |
| 89 | X₁—CH₂-(4-(2-(trifluoromethyl)benzyl)-morpholin-2-yl) | 563.3 |
| 90 | X₁—CH₂-(4-(2-(4-nitrophenyl)ethyl)-morpholin-2-yl) | 555.33 |

TABLE 7-continued

| EXAMPLE | R | MS (M + 1) |
|---|---|---|
| 91 | 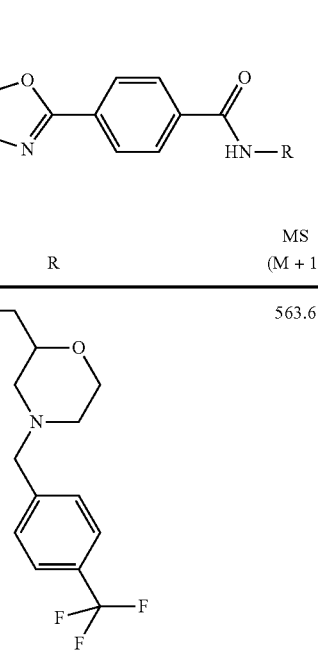 | 563.6 |
| 92 | 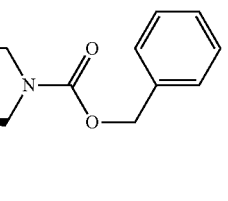 | 551.2 |
| 93 | 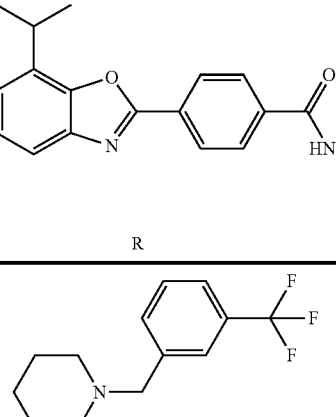 | 403.3 |
| 94 | 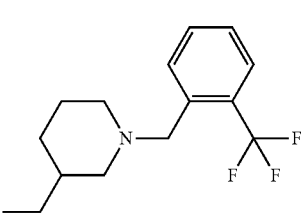 | 403.3 |
| 95 | 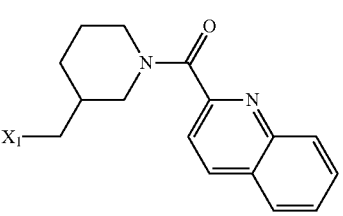 | 561.3 |
| 96 | 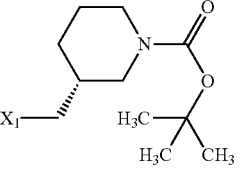 | 561.3 |
| 97 | 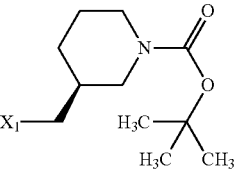 | 561.2 |
| 98 | 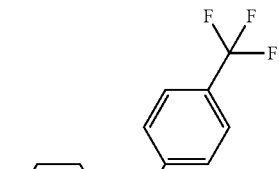 | 558.6 |

Example 99

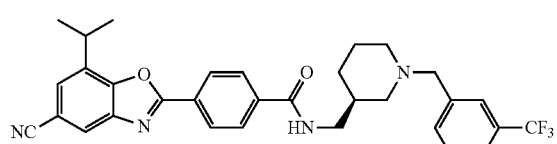

4-(5-Cyano-7-isopropyl-1,3-benzoxazol-2-yl)-N-({(3R)-1-[3-(trifluoromethyl)benzyl]piperidin-3-yl}methyl)benzamide Step A. 4-(5-Cyano-7-isopropyl-1,3-benzoxazol-2-yl)-N-[(3S)-piperidin-3-ylmethyl]benzamide To a solution of tert-butyl(3R)-3-({[4-(5-cyano-7-isopropyl-1,3-benzoxazol-2-yl)benzoyl]amino}methyl)piperidine-1-carboxylate benzoxazole (201 mg, EXAMPLE 94) in 15 ml dichloromethane was added trifluoroacetic acid (5 ml). The mixture was stirred at room temperature for 30 min. The mixture was concentrated in vacuo, diluted with 40 ml of ethyl acetate, and basified by slow and cautious addition of 40 ml of saturated aqueous sodium carbonate. The phases were separated and the aqueous phase was extracted with 40 ml of ethyl acetate. The combined organic layers were dried over sodium sulfate, filtered, and concentrated in vacuo to provide the title compound (144 mg, 89%). Mass spectrum (ESI) 403.3 (M+1).

Step B: 4-(5-Cyano-7-isopropyl-1,3-benzoxazol-2-yl)-N-({(3R)-1-[3-(trifluoromethyl)benzyl]piperidin-3-yl}methyl)benzamide 4-(5-Cyano-7-isopropyl-1,3-benzoxazol-2-yl)-N-[(3S)-piperidin-3-ylmethyl]benzamide (20 mg) was taken up in methanol (3 ml) and then potassium carbonate (14 mg) and 1-(bromomethyl)-3-(trifluoromethyl)benzene (14 □l) were added. The mixture was stirred for 1.5 h and then added directly to a Biotage 40M samplet for purification via column chromatography on a Biotage Horizon 40M column, eluting with 1 column volume of 100% hexanes followed by a gradient of 0 to 100% ethyl acetate in hexanes over 10 column volumes to provide the title compound (20 mg, 71%). Mass spectrum (ESI) 561.4 (M+1). $^1$H NMR (500 MHz, CDCl$_3$): δ 8.31 (d, J=8.4 Hz, 1H), 7.95 (s, 1H), 7.85 (d, J=8.4 Hz, 2H), 7.59 (s, 1H), 7.55 (m, 3H), 7.41 (t, J=7.7 Hz, 2H), 6.43 (t, J=5.8 Hz, 1H), 3.47 (m, 3H), 2.72 (m, 3H), 2.34 (s, 3H), 2.03 (m, 2H), 1.90 (t, J=11.4 Hz, 2H), 1.47 (d, J=6.9 Hz, 6H), 1.31 (m, 1H).

Example 100

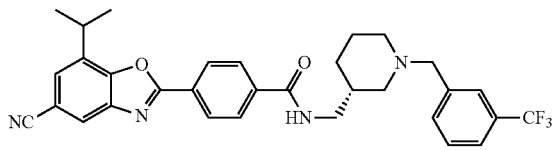 [SMILES: CC(C)c1cc(C#N)cc2nc(-c3ccc(C(=O)NC[C@@H]4CCCN(Cc5cccc(C(F)(F)F)c5)C4)cc3)oc12]

4-(5-cyano-7-isopropyl-1,3-benzoxazol-2-yl)-N-({(3S)-1-[3-(trifluoromethyl)benzyl]piperidin-3-yl}methyl)benzamide The title compound was prepared in a procedure analogous to that described in EXAMPLE 99. Mass spectrum (ESI) 561.4 (M+1). $^1$H NMR (500 MHz, CDCl$_3$): δ 8.31 (d, J=8.4 Hz, 1H), 7.95 (s, 1H), 7.85 (d, J=8.4 Hz, 2H), 7.59 (s, 1H), 7.55 (m, 3H), 7.41 (t, J=7.7 Hz, 2H), 6.43 (t, J=5.8 Hz, 1H), 3.47 (m, 3H), 2.72 (m, 3H), 2.34 (s, 3H), 2.03 (m, 2H), 1.90 (t, J=11.4 Hz, 2H), 1.47 (d, J=6.9 Hz, 6H), 1.31 (m, 1H).

Intermediate 20

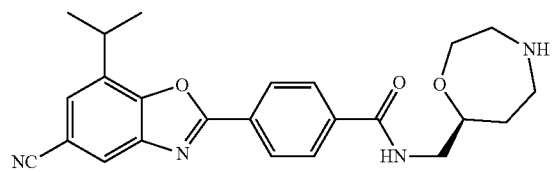 [SMILES: CC(C)c1cc(C#N)cc2nc(-c3ccc(C(=O)NC[C@@H]4CCNCCO4)cc3)oc12]

4-(5-Cyano-7-isopropyl-1,3-benzoxazol-2-yl)-N-[(7S)-1,4-oxazepan-7-ylmethyl]benzamide Step A: Benzyl (7S)-7-({[4-(5-cyano-7-isopropyl-1,3-benzoxazol-2-yl)benzoxazol-2-yl]amino}methyl-1,4-oxazepane-4-carboxylate The title compound was prepared using a procedure analogous to that described for EXAMPLE 1. Mass spectrum (ESI) 553.3 (M+1).

Step B: 4-(5-Cyano-7-isopropyl-1,3-benzoxazol-2-yl)-N-[(7S)-1,4-oxazepan-7-ylmethyl]benzamide To a solution of benzyl(7S)-7-({[4-(5-cyano-7-isopropyl-1,3-benzoxazol-2-yl)benzoyl]amino}methyl-1,4-oxazepane-4-carboxylate (211 mg) in 30 ml methanol was added 10% palladium on carbon (40 mg). The mixture was stirred under an atmosphere of hydrogen (via balloon) overnight at room temperature. The mixture was then filtered through a small plug of Celite and concentrated in vacuo to provide the title compound (133 mg, 83%). Mass spectrum (ESI) 419.3 (M+1).

Example 101

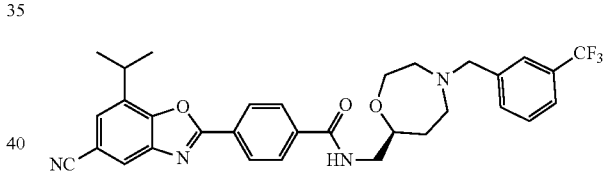

4-(5-Cyano-7-isopropyl-1,3-benzoxazol-2-yl)-N-({(7S)-4-[3-(trifluoromethyl)benzyl]-1,4-oxazepan-7-yl}methyl)benzamide To a mixture of 36 mg of potassium carbonate in methanol (3 ml) was added 37 mg of 4-(5-cyano-7-isopropyl-1,3-benzoxazol-2-yl)-N-[(7S)-1,4-oxazepan-7-ylmethyl]benzamide (INTERMEDIATE 20) followed by 1-(bromomethyl)-3-(trifluoromethyl)benzene (13 μl). The mixture was heated to 70° C. and stirred for 8 h, and then cooled and added directly to a 40M samplet for purification via column chromatography on a Biotage Horizon 40M column, eluting with 1 column volume of 100% hexanes, followed by a gradient of 0 to 100% ethyl acetate in hexanes over 10 column volumes, followed by 4 column volumes of 100% ethyl acetate, to provide the title compound (28 mg, 56%). Mass spectrum (ESI) 577.2 (M+1). $^1$H NMR (500 MHz, CDCl$_3$): δ 8.33 (d, J=8.4 Hz, 2H), 7.96 (d, J=6.0 Hz, 2H), 7.94 (s, 1H), 7.61 (s, 1H), 7.52 (m, 3H), 7.44 (t, J=7.5 Hz, 1H), 6.65 (bs, 1H), 3.96 (m, 2H), 3.81 (m, 2H), 3.70 (s, 2H), 3.68 (m, 2H), 3.48 (sept, J=7.0 Hz, 1H), 3.25 (m, 1H), 2.74 (m, 2H), 2.01 (m, 1H), 1.82 (m, 1H), 1.46 (d, J=7.0 Hz, 6H).

Example 102

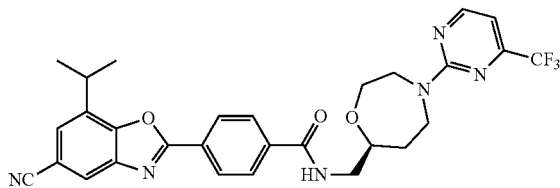 [SMILES: CC(C)c1cc(C#N)cc2nc(-c3ccc(C(=O)NC[C@@H]4CCN(c5nccc(C(F)(F)F)n5)CCO4)cc3)oc12]

4-(5-Cyano-7-isopropyl-1,3-benzoxazol-2-yl)-
N-({(7S)-4-[4-(trifluoromethyl)pyrimidin-2-yl]-1,4-
oxazepan-7-yl}methyl)benzamide To a mixture of 48 mg of potassium carbonate in methanol (3 ml) was added 37 mg of 4-(5-cyano-7-isopropyl-1,3-benzoxazol-2-yl)-N-[(7S)-1,4-oxazepan-7-ylmethyl]benzamide (INTERMEDIATE 20) followed by 2-chloro-4-(trifluoromethyl)pyrimidine (16 mg). The mixture was heated via microwave at 120° C. for 35 min, and then cooled and added directly to a 40M samplet for purification via column chromatography on a Biotage Horizon 40M column, eluting with 1 column volume of 100% hexanes, followed by a gradient of 0 to 100% ethyl acetate in hexanes over 10 column volumes, followed by 4 column volumes of 100% ethyl acetate, to provide the title compound (37 mg, 76%). Mass spectrum (ESI) 565.2 (M+1). $^1$H NMR (500 MHz, CDCl$_3$): δ 8.52 (s, 1H), 8.35 (d, J=8.5 Hz, 2H), 7.96 (d, J=8.3 Hz, 2H), 7.95 (s, 1H), 7.54 (s, 1H), 6.81 (d, J=4.8 Hz, 1H), 6.65 (bs, 1H), 4.26 (m, 2H), 3.98 (m, 3H), 3.70 (s, 2H), 3.69 (m, 2H), 3.48 (sept, J=7.0 Hz, 1H), 3.25 (m, 1H), 2.19 (m, 1H), 1.83 (m, 1H), 1.48 (d, J=7.1 Hz, 6H).

Intermediate 21

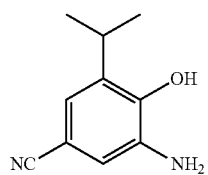

3-Amino-4-hydroxy-5-isopropylbenzonitrile

Step A. 3-Bromo-4-methoxy-5-nitrobenzonitrile 3-bromo-4-methoxybenzonitrile (5.22 g, 24.62 mmol) was added to rapidly stirring fuming nitric acid (10 ml, 201 mmol) at 0° C. The ice bath was removed and the reaction mixture was stirred for 2 h at room temperature. The reaction mixture was diluted with ethyl acetate and water, and then the organic layer was washed with water and brine, dried (sodium sulfate), filtered, and concentrated in vacuo to afford the title compound, which was carried on without further purification.

Step B. 3-Isopropenyl-4-methoxy-5-nitrobenzonitrile

To a mixture of 3-bromo-4-methoxy-5-nitrobenzonitrile (6.26 g, 24.35 mmol) in dimethoxyethane (61 ml) was added water (16 ml), isopropenyl boronic acid (6.28 g, 73.1 mmol), potassium carbonate (10.10 g, 73.1 mmol), and tetrakis(triphenylphosphine) palladium(0) (0.281 g, 0.244 mmol). The resulting mixture was heated to reflux and stirred at this temperature overnight under nitrogen. The reaction mixture was then concentrated, diluted with water, and extracted with ethyl acetate (3×). The combined organics were washed with brine, dried over sodium sulfate, filtered, and concentrated in vacuo. The residue was purified by flash column chromatography using a Horizon Biotage, 65i Si column, eluting with 1 column volume of hexanes, followed by a linear gradient of ethyl acetate in hexanes from 0% to 100% over 10 column volumes to afford the title compound as a red oil.

Step C. 4-Hydroxy-3-isopropenyl-5-nitrobenzonitrile

A mixture of 3-isopropenyl-4-methoxy-5-nitrobenzonitrile (5.06 g, 23.19 mmol) and pyridine hydrochloride (10 g, 87 mmol) was placed in an oil bath at 200° C. for 4 min. The reaction mixture was then cooled to room temperature, added 1M HCl, and extracted 3 times with ethyl acetate. The combined organics were washed with brine, dried over sodium sulfate, filtered, and concentrated in vacuo. The residue was purified by flash column chromatography using a Horizon Biotage, 65i Si column, eluting with 1 column volume of 1% ethyl acetate in hexanes, followed by a linear gradient of ethyl acetate in hexanes from 1% to 100% over 10 column volumes to afford the title compound. Mass spectrum (ESI) 203.1 (M−1).

Step D. 3-Amino-4-hydroxy-5-isopropylbenzonitrile

To a solution of 4-hydroxy-3-isopropenyl-5-nitrobenzonitrile (4.135 g, 20.25 mmol) in ethyl acetate (100 ml) was added 1.2 g of Pd/C. The resulting mixture was degassed and flushed with nitrogen, and then degassed and flushed with hydrogen using a double balloon. The reaction was stirred under hydrogen for 14 h, and then diluted with ethyl acetate, filtered through a pad of Celite and concentrated. The residue was purified by flash column chromatography using a Horizon Biotage, 65i Si column, eluting with 1 column volume of dichloromethane, followed by a linear gradient of ethyl acetate in dichloromethane from 0% to 50% over 10 column volume. It was then repurified by flash column chromatography using a Horizon Biotage, 65i Si column, eluting with 1 column volume of 5% ethyl acetate in hexanes, followed by a linear gradient of ethyl acetate in hexanes from 5% to 100% over 10 column volumes to afford the title compound. Mass spectrum (ESI) 177.4 (M+1).

Example 103

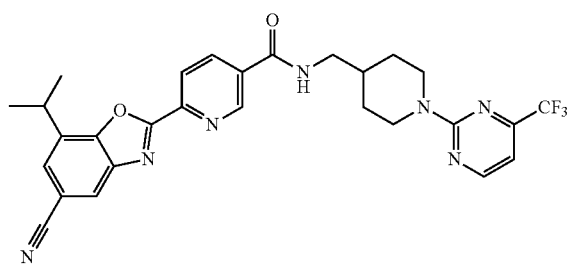 [SMILES: CC(C)c1cc(C#N)cc2nc(-c3ccc(C(=O)NCC4CCN(c5nccc(C(F)(F)F)n5)CC4)cn3)oc12]

6-(5-Cyano-7-isopropyl-1,3-benzoxazol-2-yl)-N-({1-[4-(trifluoromethyl)pyrimidin-2-yl]piperidin-4-yl}methyl)nicotinamide

Step A: 6-(Methoxycarbonyl)nicotinic acid

To a suspension of 2,5-pyridinecarboxylic acid (20.0 g, 0.131 mol) in methanol (238 ml) was added concentrated sulfuric acid (7.14 g). The reaction was heated to reflux and stirred at this temperature for 2 h. After cooling to room temperature, reaction was poured into water (1000 ml). The light yellow precipitate was filtered, washed with water (2×100 ml), and dried in vacuo to afford the title compound (14.2 g). Mass spectrum (ESI) 182 (M+1).

Step B: Methyl-5-{[({1-[4-(trifluoromethyl)pyrimidin-2-yl]piperidin-4-yl}methyl)amino]carbonyl}pyridine-2-carboxylate To a solution of 6-(methoxycarbonyl)nicotinic acid (250 mg, 1.39 mmol) and 1-{1-[4-(trifluoromethyl)pyrimidin-2-yl]piperidin-4-yl}methanamine (INTERMEDIATE 6, 361 mg, 1.39 mmol) in dimethylformamide (5.0 ml) were added hydroxybenzotriazole (225 mg, 1.67 mmol), 1-(3-dimethylaminopropyl)-3-ethylcarbodiimide hydrochloride (320 mg, 1.67 mmol), and N,N-diisopropylethylamine (291 μl, 1.67 mmol). The reaction was allowed to stir at ambient temperature for 18 h. After removal of the solvent by evaporation, the residue was purified by flash chromatography on a silica gel column, eluting with a gradient of 0-100% ethyl acetate in hexanes to give the title compound as a white solid (272.2 mg). Mass spectrum (ESI) 425 (M+1). $^1$H NMR (500 MHz, CDCl$_3$) δ 9.13 (s, 1H), 8.49 (d, 1H, J=4.8 Hz), 8.33 (d, 1H, J=8.0 Hz), 8.24 (d, 1H, J=8 Hz), 6.73-6.77 (m, 2H), 4.87 (d, 2H, J=13.5 Hz), 4.05 (s, 3H), 3.44-3.47 (m, 2H), 2.90-2.98 (m, 2H), 1.90-2.00 (m, 1H), 1.90 (d, 2H, J=12.6 Hz), 1.27-1.36 (m, 2H).

Step C: 5-{[({1-[4-(Trifluoromethyl)pyrimidin-2-yl]piperidin-4-yl}methyl)amino]carbonyl}pyridine-2-carboxylic acid To a suspension of methyl-5-{[({1-[4-(trifluoromethyl)pyrimidin-2-yl]piperidin-4-yl}methyl)amino]carbonyl}pyridine-2-carboxylate (272 mg, 0.643 mmol) in tetrahydrofuran, methanol, and water (5 ml, in a ratio of 3:2:1, respectively) was added lithium hydroxide (108 mg, 2.57 mmol). The reaction was stirred at ambient temperature for 18 h and then concentrated in vacuo to afford the title compound as a white solid (230 mg). Mass spectrum (ESI) 410 (M+1). $^1$H NMR (500 MHz, CD$_3$OD) δ 8.96 (s, 1H), 8.54 (d, 1H, J=4.8 Hz), 8.24 (d, 1H, J=8.3 Hz), 8.05 (d, 1H, J=8 Hz), 6.81 (d, 1H, J=4.8 Hz), 4.70-5.0 (m, 2H), 2.94-3.01 (m, 2H), 1.97-2.03 (m, 1H), 1.88 (d, 2H, J=12.8 Hz), 1.21-1.34 (m, 4H).

Step D: N-(5-Cyano-2-hydroxy-3-isopropylphenyl)-N-({1-[4-(trifluoromethyl)pyrimidin-2-yl]piperidin-4-yl}methyl)pyridine-2,5-dicarboxamide To a suspension of 5-{[({1-[4-(trifluoromethyl)pyrimidin-2-yl]piperidin-4-yl}methyl)amino]carbonyl}pyridine-2-carboxylic acid (182 mg, 0.45 mmol) in dichloromethane (8.0 ml) was added oxalyl chloride (58.0 μl, 0.66 mmol) and dimethylformamide (2 μl). The reaction stirred at ambient temperature for 2.5 h. The mixture was then concentrated in vacuo, and co-concentrated with toluene (3×8 ml). The mixture was diluted with 1,4-dioxane (8.0 ml). 3-Amino-4-hydroxy-5-isopropylbenzonitrile (79.3 mg, 0.45 mmol, INTERMEDIATE 21) was added, and the mixture was heated to reflux for 18 h. After cooling to room temperature, reaction was partitioned between water and ethyl acetate, extracted with ethyl acetate three times, dried over magnesium sulfate, filtered, and concentrated in vacuo. Purification by preparative TLC (silica gel, mobile phase 10% methanol in dichloromethane) afforded the title compound as a yellow solid (121.7 mg). Mass spectrum (ESI) 568 (M+1). $^1$H NMR (500 MHz, CD$_3$OD) δ 9.10 (s, 1H), 8.54 (d, 1H, J=4.8 Hz), 8.39-8.45 (m, 2H), 8.32 (d, 1H, J=8 Hz), 7.39 (d, 1H, J=1.8 Hz), 6.82 (d, 1H, J=4.8 Hz), 4.70-5.0 (m, 2H), 4.58 (s, 1H), 3.35-3.4 (m, 3H), 2.95-3.05 (m, 2H), 2.00-2.05 (m, 1H), 1.85-1.90 (m, 2H), 1.31 (d, 6H, J=4.6 Hz).

Step E: 6-(5-Cyano-7-isopropyl-1,3-benzoxazol-2-yl)-N-({1-[4-(trifluoromethyl)pyrimidin-2-yl]piperidin-4-yl}methyl)nicotinamide To a solution of N-(5-cyano-2-hydroxy-3-isopropylphenyl)-N-({1-[4-(trifluoromethyl)pyrimidin-2-yl]piperidin-4-yl}methyl)pyridine-2,5-dicarboxamide (121 mg, 0.213 mmol) in toluene (10.0 ml) was added p-toluenesulfonic acid (122 mg, 0.640 mmol). The reaction was heated to reflux for 7 h. The mixture was partitioned between saturated sodium bicarbonate and ethyl acetate, extracted with ethyl acetate, dried over magnesium sulfate, filtered, and concentrated in vacuo. The aqueous layer was then also extracted with dichloromethane 3 times, dried over magnesium sulfate, filtered, and concentrated in vacuo. The two organic extractions were combined and purified by preparative TLC (silica gel, mobile phase 10% methanol in dichloromethane) to afford the title compound as a white solid (84 mg). Mass spectrum (ESI) 550 (M+1). $^1$H NMR (500 MHz, DMSO) δ 9.22 (s, 1H), 8.92-8.95 (m, 1H), 8.66 (d, 1H, J=4.6 Hz), 8.45-8.49 (m, 2H), 8.36 (s, 1H), 7.87 (s, 1H), 6.97 (d, 1H, J=4.8 Hz), 4.61-4.75 (m, 2H), 3.42-3.55 (m, 1H), 3.21-3.29 (m, 2H), 2.92-3.02 (m, 2H), 1.90-2.00 (m, 1H), 1.80 (d, 2H, J=13.2 Hz), 1.41 (d, 6H, J=6.9 Hz), 1.12-1.27 (m, 2H).

Example 104

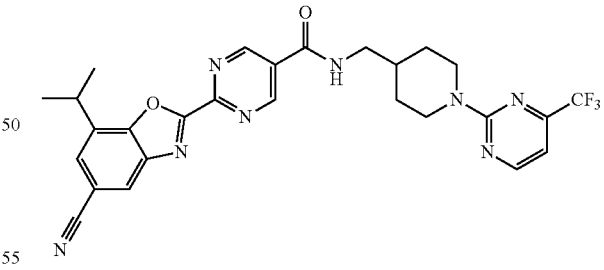

2-(5-Cyano-7-isopropyl-1,3-benzoxazol-2yl)-N-({1-[4-(trifluoromethyl)pyrimidine-2-yl]piperidi-4-yl}methyl)pyrimidine-5-carboxamide

Step A: Methyl-2-chloropyrimidine-5-carboxylate

To a solution 2-chloropyrimidine-5-carboxylic acid (1.63 g, 10.28 mmol) in a mixture of methanol (20 ml) and benzene (50 ml) was added a solution of (trimethylsilyl)diazomethane in hexanes (2.0 M, 10 ml) at room temperature. The mixture was stirred for 30 min, and then was concentrated to give the title compound (1.77 g) as a yellow solid. Mass spectrum (ESI) 173.2 (M+1). $^1$H NMR (500 MHz, CDCl$_3$) δ 9.18 (s, 2H), 4.02 (s, 3H).

Step B: Methyl-2-vinylpyrimidine-5-carboxylate

To a solution of methyl-2-chloropyrimidine-5-carboxylate (2.084 g, 12.08 mmol) and tributyl(vinyl)tin (3.635 g, 11.46 mmol) in toluene (15 ml) was added triphenylphosphine (94.9 mg, 0.362 mmol) followed by tetrakis(triphenylphosphine) palladium(0) (418.5 mg, 0.362 mmol). The mixture was stirred at 110° C. for 10 h under anhydrous argon. After evaporation of solvent, the residue was purified by flash chromatography (hexanes-ethyl acetate=4:1, then 1:1) to give the title compound (0.842 g) as a white solid. Mass spectrum (ESI) 166.2 (M+1). $^1$H NMR (500 MHz, CDCl$_3$) δ 9.26 (s, 2H), 6.95-7.01 (m, 1H), 6.82 (dd, 1H, J=1.4, 17.2 Hz), 5.92 (dd, 1H, J=1.4, 10.5 Hz), 4.01 (s, 3H).

Step C: Methyl-2-formylpyrimidine-5-carboxylate

A solution of methyl-2-vinylpyrimidine-5-carboxylate (2.18 g, 13.29 mmol) in dichloromethane (70 ml) was cooled to −78° C. Ozone was bubbled through the cold reaction mixture for 20 min, and then dimethyl sulfide (10 ml) was added. The mixture was stirred at room temperature for 18 h, and then the white precipitate was filtered. The filtrate was concentrated to give the title compound (3.064 g) as viscous greenish yellow oil. $^1$H NMR (500 MHz, CDCl$_3$) δ 10.21 (s, 1H), 9.53 (s, 2H), 4.02 (s, 3H).

Step D: Methyl-2-(5-cyano-7-isopropyl-1,3-benzoxazol-2-yl)pyrimidine-5-carboxylate Methyl-2-formylpyrimidine-5-carboxylate (200 mg, 1.205 mmol) and 3-amino-4-hydroxy-5-isopropylbenzonitrile (212 mg, 1.205 mmol) were dissolved in methanol (5 ml). The mixture was concentrated, and then the residue was dissolved in dichloromethane (5 ml). To the above solution was added 2,3-dichloro-5,6-dicyano-p-benzoquinone (300.9 mg, 1.325 mmol) at room temperature. The solution was stirred at room temperature for 30 min, and then concentrated. The residue was partitioned between ethyl acetate and saturated aqueous sodium bicarbonate solution. The aqueous layer was extracted with ethyl acetate (3×). The combined organics were washed with brine, dried over magnesium sulfate, and concentrated. The residue was purified by flash chromatography (hexanes-ethyl acetate=4:1, then 1:1) to provide of the title compound (139 mg) as a yellow solid. Mass spectrum (ESI) 322.8 (M+1). $^1$H NMR (500 MHz, CDCl$_3$) δ 9.55 (s, 2H), 8.13 (s, 1H), 7.66 (s, 1H), 4.09 (s, 3H), 3.65 (m, 1H), 1.50 (d, 6H, J=6.8 Hz).

Step E: 2-(5-Cyano-7-isopropyl-1,3-benzoxazol-2yl)pyrimidine-5-carboxylic acid

To a solution of methyl-2-(5-cyano-7-isopropyl-1,3-benzoxazol-2yl)pyrimidine-5-carboxylate (429 mg, 1.332 mmol) in tetrahydrofuran (30 ml) was added 1N lithium hydroxide (1.466 ml) dropwise at 60° C. The reaction mixture was stirred at room temperature for 4 h, and then the solution was concentrated and the residue was partitioned between ethyl acetate and water. The aqueous layer was acidified with 1N HCl to pH=4~5. The white solid was filtered and dissolved in a mixture of dichloromethane and methanol (9:1). This solution was dried over magnesium sulfate and then concentrated to provide the title compound (74 mg) as a yellow solid. Mass spectrum (ESI) 308.8 (M+1). $^1$H NMR (500 MHz, DMSO) δ 9.45 (s, 2H), 8.42 (s, 1H), 7.92 (s, 1H), 3.20~3.60 (m, 1H, overlapped with H$_2$O peak), 1.41 (s, 6H).

Step F: 2-(5-Cyano-7-isopropyl-1,3-benzoxazol-2yl)-N-({1-[4-(trifluoromethyl)pyrimidine-2-yl]piperidi-4-yl}methyl)pyrimidine-5-carboxamide To a solution of 2-(5-cyano-7-isopropyl-1,3-benzoxazol-2yl)pyrimidine-5-carboxylic acid (30 mg, 0.097 mmol) and 1-{1-[4-(trifluoromethyl)pyrimidine-2-yl]piperidi-4-yl}methanamine (INTERMEDIATE 6, 25.3 mg, 0.097 mmol) in dimethylformamide (2 ml) were added hydroxybenzotriazole (15.7 mg, 0.116 mmol), 1-(3-dimethylaminopropyl)-3-ethylcarbodiimide hydrochloride (27.9 mg, 0.146 mmol), and N,N-diisopropylethylamine (25.4 μL, 0.146 mmol) sequentially at room temperature. The solution was stirred at room temperature for 18 h, and then concentrated. The residue was partitioned between ethyl acetate and saturated aqueous sodium bicarbonate. The aqueous layer was extracted with ethyl acetate (3×), washed with brine, dried over magnesium sulfate, and concentrated. The residue was purified on a 1000-micron preparative TLC plate eluting with a mixture of hexanes and ethyl acetate (1:1), to provide 21.4 mg of the title compound as a white solid. Mass spectrum (ESI) 550.9 (M+1). $^1$H NMR (500 MHz, CDCl$_3$) δ 9.41 (s, 2H), 8.54 (d, 1H, d=4.8 Hz), 8.13 (s, 1H), 7.66 (s, 1H), 6.81 (d, 1H, d=4.8 Hz), 6.68 (br s, 1H), 4.93 (d, 2H, d=13.8 Hz), 3.65 (m, 1H), 3.52 (t, 2H, d=6.1 Hz), 3.01 (t, 2H, d=12.1 Hz), 2.00-2.15 (m, 1H), 1.96 (d, 2H, d=12.6 Hz), 1.50 (d, 6H, d=6.8 Hz), 1.38 (q, 2H, J=9.2 Hz).

Intermediate 22

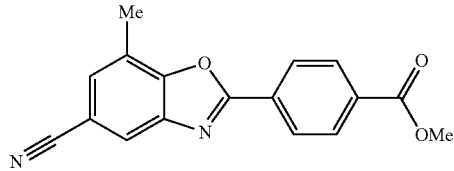 [SMILES: COC(=O)c1ccc(-c2nc3cc(C#N)cc(C)c3o2)cc1]

Methyl 4-(5-cyano-7-methyl-1,3-benzoxazol-2-yl)benzoate

Step A. 4-Hydroxy-3-methyl-5-nitrobenzonitrile

To a solution of 4.0 g of 4-hydroxy-3-iodo-5-nitrobenzonitrile in 240 ml dimethylformamide was added 4.13 g of methyl boronic acid, and 8.99 g of cesium carbonate. The mixture was then degassed by bubbling argon gas through it for 30 min. Tris(dibenzylidineacetone)dipalladium (1.38 g) was added, and the mixture was then heated to 130° C. for 15 h. Analysis of the crude mixture via LC/MS showed complete formation of the desired product with ca. 14% reduction of the iodide. The mixture was cooled to room temperature, diluted with water (300 ml) and acetic acid (~50 ml), and then extracted with ethyl acetate (5×300 ml). The organic layers were dark red-brown to light green-yellow in succession. The combined organic layers were extracted with water (2×300 ml) and then 2M sodium hydroxide (3×300 ml). The aqueous layers were red to yellow in succession. The combined aqueous layers (containing the phenol), were made slightly acidic by addition of 100 ml of acetic acid and then extracted with ethyl acetate (3×300 ml). These organic layers were combined, dried over sodium sulfate, filtered and concentrated in vacuo. The residue was purified via flash chromatography ($R_f$=0.17 in 2/1 hexanes/ethyl acetate) on a Biotage Horizon, 65i column, eluting with 1 column volume of 5% ethyl acetate in hexanes, followed by a linear gradient from 5 to 80% of ethyl acetate in hexanes over 10 column volumes to provide 1.01 g (41%) of the title compound. The base-extracted organic layer was concentrated in vacuo and purified via flash chromatography on a Biotage Horizon in the same way to provide an additional 305 mg (12%) of the title compound. Mass spectrum (ESI) 177.0 (M−1). $^1$H NMR (500 MHz, CDCl$_3$): δ 11.23 (s, 1H), 8.33 (s, 1H), 7.68 (s, 1H), 2.39 (s, 3H).

Step B. 3-Amino-4-hydroxy-5-methylbenzonitrile

Iron chloride hexahydrate (9.6 mg), 4-hydroxy-3-methyl-5-nitrobenzonitrile (126 mg), and 77 mg of activated carbon were suspended in 5 ml of methanol and heated under N$_2$ at 70° C. for 10 min. Hydrazine (0.11 ml) was then added slowly and the mixture was stirred for 2 h at 70° C. The mixture was then cooled to room temperature and filtered through a plug of Celite, eluting with methanol. The eluent was concentrated in vacuo and the residue was purified on a 2×1500 micron preparative TLC plate, eluting with ethyl acetate ($R_f$=0.24), to provide 101 mg (96%) of the title compound. Mass spectrum (ESI) 150.1 (M+1). $^1$H NMR (500 MHz, CDCl$_3$): □ 6.93 (s, 1H), 6.91 (s, 1H), 5.21 (bs, 1H), 3.76 (bs, 2H), 2.42 (s, 3H).

Step C. Methyl 4-(5-cyano-7-methyl-1,3-benzoxazol-2-yl)benzoate

To a solution of 117 mg of toluenesulfonic acid in 40 ml of dioxane was added 3-amino-4-hydroxy-5-methylbenzonitrile (101 mg) and methyl 4-(chlorocarbonyl)benzoate (149 mg) The mixture was heated to reflux under N$_2$ for 15 h. The mixture was then cooled to room temperature and the dioxane was removed in vacuo. To the residue was added 80 ml of toluene and the solution was heated to reflux overnight (15 h). Purification by flash chromatography ($R_f$ in 2/1 hexanes/ethyl acetate=0.58) on a Biotage Horizon, 65i column, eluting with 1 column volume of 30% ethyl acetate in hexanes, followed by a linear gradient of ethyl acetate in hexanes from 30 to 100% over 10 column volumes provided 134 mg (67%) of the title compound. Mass spectrum (ESI) 293.0 (M+1). $^1$H NMR (500 MHz, CDCl$_3$): δ 8.35 (d, J=8.2 Hz, 2H), 8.22 (d, J=8.4 Hz, 2H), 7.95 (s, 1H), 7.49 (s, 1H), 3.98 (s, 3H), 2.65 (s, 3H).

Example 105

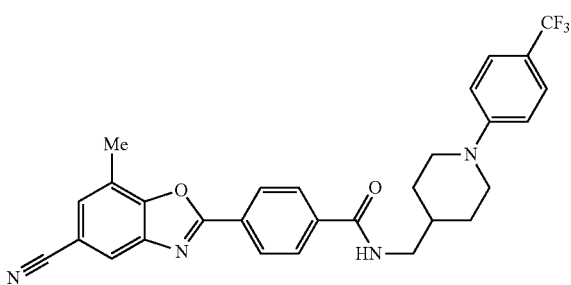 [SMILES: Cc1cc(C#N)cc2nc(-c3ccc(C(=O)NCC4CCN(c5ccc(C(F)(F)F)cc5)CC4)cc3)oc12]

4-(5-Cyano-7-methyl-1,3-benzoxazol-2-yl)-N-({1-[4-(trifluoromethyl)phenyl]piperidin-4-yl}methyl)benzamide Methyl 4-(5-cyano-7-methyl-1,3-benzoxazol-2-yl)benzoate (134 mg, INTERMEDIATE 22) and lithium hydroxide (22 mg) were combined in 10 ml of a 1:1:1 mixture of tetrahydrofuran, methanol, and water. The solution was stirred overnight. The solvents were removed in vacuo to provide the desired intermediate, lithium 4-(5-cyano-7-methyl-1,3-benzoxazol-2-yl)benzoate, as an off-white solid (140 mg). Mass spectrum (ESI) 279.0 (M+1). To a solution of lithium 4-(5-cyano-7-methyl-1,3-benzoxazol-2-yl)benzoate (28 mg) in 2 ml of dichloromethane was added 2.5 ml of a 2M solution of oxalyl chloride in dichloromethane followed by 10 µl of dimethylformamide. The mixture was warmed and stirred until the solids dissolved (about 0.5 h). The mixture was concentrated in vacuo with minimal or no heating (<30° C.) and then dried under high vacuum to remove traces of water. To the residue was added 2 ml of dichloromethane, 28 mg of ({1-[4-(trifluoromethyl)phenyl]piperidin-4-yl}methyl)amine, and 87 µl of diisopropylethylamine. The mixture was stirred at room temperature for 15 min and then was added directly to a 40M samplet. The product was purified via flash chromatography on a Biotage Horizon, 40M column, eluting with 1 column volume of 10% ethyl acetate in hexanes, followed by a linear gradient of ethyl acetate in hexanes from 10 to 100% over 10 column volumes to provide the title compound (38 mg, 73%). Mass spectrum (ESI) 519.0 (M+1). $^1$H NMR (500 MHz, CDCl$_3$): δ 8.35 (d, J=8.5 Hz, 2H), 7.95 (m, 4H), 7.49 (m, 4H), 6.37 (bs, 2H), 3.83 (d, J=12.6 Hz, 2H), 3.49 (m, 2H), 3.47 (t, J=6.4 Hz, 2H), 2.87 (m, 2H), 2.65 (s, 3H), 1.92 (m, 3H).

Example 106

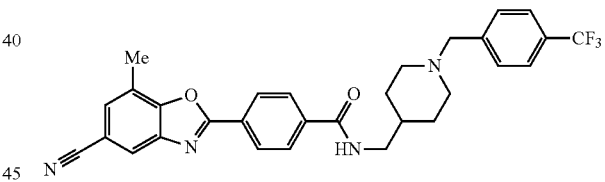

4-(5-Cyano-7-methyl-1,3-benzoxazol-2-yl)-N-({1-[4-(trifluoromethyl)benzyl]piperidin-4-yl}methyl)benzamide Step A. 4 tert-Butyl-4-({[4-(5-cyano-7-methyl-1,3-benzoxazol-2-yl)benzoyl]amino}methyl)piperidine-1-carboxylate The title compound was synthesized from methyl 4-(5-cyano-7-methyl-1,3-benzoxazol-2-yl)benzoate (INTERMEDIATE 22) following the procedure described in EXAMPLE 105. Mass spectrum (ESI) 475.1 (M+1).

Step B. 4-(5-Cyano-7-methyl-1,3-benzoxazol-2-yl)-N-({1-[4-(trifluoromethyl)benzyl]piperidin-4-yl}methyl)benzamide To a solution of trifluoroacetic acid (2 ml) in dichloromethane (2 ml) was added 4 tert-butyl-4-({[4-(5-cyano-7-methyl-1,3-benzoxazol-2-yl)benzoyl]amino}methyl)piperidine-1-carboxylate (68 mg). The mixture was stirred for 1 h, and then concentrated in vacuo to provide 4-(5-cyano-7-methyl-1,3-benzoxazol-2-yl)-N-(piperidin-4-ylmethyl)benzamide (67 mg. 99%). Half of this sample was added to potassium carbonate (19 mg) in ethanol. 4-Trifluoromethylbenzyl bromide (17 mg) was added and the mixture was heated to 70° C. for 4 h. The sample was cooled to room temperature, concentrated in vacuo, and was purified via preparative thin-layer chromatography (R$_f$=0.58 in 1:1 hexanes-ethyl acetate) to provide the title compound (31 mg, 84%). Mass spectrum (ESI) 533.2 (M+1). $^1$H NMR (500 MHz, CDCl$_3$): δ 8.34 (d, J=8.5 Hz, 2H), 7.94 (d, J=8.4 Hz, 2H), 7.94 (s, 1H), 7.57 (d, J=7.6 Hz, 2H), 7.48 (s, 1H), 7.44 (d, J=7.6 Hz, 2H), 6.23 (t, J=6.4 Hz, 1H), 3.55 (s, 2H), 3.42 (t, J=6.2 Hz, 2H), 2.99 (m, 2H), 2.65 (s, 6H), 2.03 (m, 2H), 1.76, m (2H), 1.42 (m, 3H).

Intermediate 23

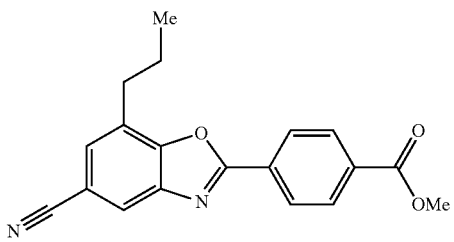 [SMILES: CCCc1cc(C#N)cc2nc(-c3ccc(C(=O)OC)cc3)oc12]

Methyl 4-(5-cyano-7-propyl-1,3-benzoxazol-2-yl)benzoate

Step A. 4-Hydroxy-3-nitro-5-[(1E)-prop-1-en-1-yl] benzonitrile

To a solution of 2.61 g of 4-hydroxy-3-iodo-5-nitrobenzonitrile in 315 ml of dioxane and 18 ml of water was added potassium carbonate (2.49 g), isopropenyl boronic acid (3.09 g), and tris(dibenzylideneacetone)dipalladium(0) (824 mg). This mixture was heated to reflux for 72 h. LC/MS analysis of the crude reaction mixture showed formation of a ca. 1:1 mixture of the desired product and the isopropenyl isomer. The mixture was cooled to room temperature, acidified by addition of 10 ml of acetic acid, loaded onto a silica gel column, eluted with ethyl acetate, and concentrated in vacuo. The residue was dissolved in dichloromethane and a small amount of ethyl acetate and was purified by column chromatography (2×) on a Biotage Horizon instrument (65i column), eluting with 1 column volume of 100% hexanes followed by a gradient of 0-20% ethyl acetate in hexanes over 10 column volumes to provide the title compound (1.78 g, 97%) contaminated with a small amount of dibenzylideneacetone. Mass spectrum (ESI) 203.1 (M−1).

Step B. 3-Amino-4-hydroxy-5-propylbenzonitrile

To a solution of 1.78 g of 4-hydroxy-3-nitro-5-[(1E)-prop-1-en-1-yl]benzonitrile in ethyl acetate (10 ml) was added palladium on carbon (100 mg). This mixture was evacuated and flushed with hydrogen (via balloon) 10 times. The reaction was stirred at room temperature for 14 h under hydrogen. The mixture was then filtered through a plug of Celite, eluting with methanol. After concentration of the eluent in vacuo, the residue was further purified by column chromatography on a Biotage Horizon, eluting with 1 column volume of 100% hexanes followed by a gradient of 0-20% ethyl acetate in hexanes over 10 column volumes to provide the title compound (400 mg, 26%). Mass spectrum (ESI) 177.2 (M+1).

Step C. Methyl 4-(5-cyano-7-propyl-1,3-benzoxazol-2-yl)benzoate

The title compound was prepared following a procedure analogous to that described for INTERMEDIATE 22. Mass spectrum (ESI) 321.1 (M+1).

Example 107

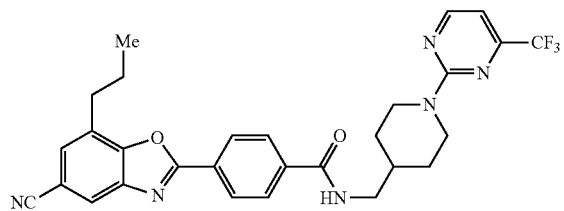 [SMILES: CCCc1cc(C#N)cc2nc(-c3ccc(C(=O)NCC4CCN(c5nccc(C(F)(F)F)n5)CC4)cc3)oc12]

Methyl 4-(5-cyano-7-propyl-1,3-benzoxazol-2-yl)benzoate

The title compound was prepared following a procedure analogous to that described for EXAMPLE 1. Mass spectrum (ESI) 549.2 (M+1). $^1$H NMR (500 MHz, CDCl$_3$): δ 8.48 (d, J=4.8 Hz, 1H), 8.34 (d, J=8.5 Hz, 2H), 7.95 (d, J=8.0 Hz, 2H), 7.94 (s, 1H), 7.49 (s, 1H), 6.72 (d, J=4.8 Hz, 1H), 6.31 (t, J=5.9 Hz, 1H), 4.87 (d, J=13.3 Hz, 2H), 3.45 (t, J=6.4 Hz, 2H), 2.97 (t, J=7.6 Hz, 2H), 2.96 (m, 2H), 2.03 (m, 1H), 1.90 (d, J=12.5 Hz, 2H), 1.85 (sext, J=7.6 Hz, 2H), 1.31 (qd, J=12.3, 3.9 Hz, 2H), 1.04 (t, J=7.3 Hz, 3H).

Example 108

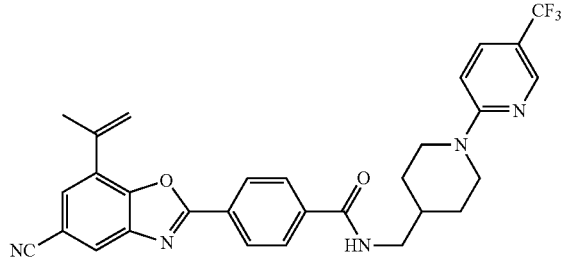 [SMILES: C=C(C)c1cc(C#N)cc2nc(-c3ccc(C(=O)NCC4CCN(c5ccc(C(F)(F)F)cn5)CC4)cc3)oc12]

4-(5-Cyano-7-isopropenyl-1,3-benzoxazol-2-yl)-N-({1-[5-(trifluoromethyl)pyridin-2-yl]piperidin-4-yl}methyl)benzamide Step A. Methyl 4-(7-isopropenyl-5-methoxy-1,3-benzoxazol-2-yl)benzoate The title compound was prepared using a procedure analogous to that described in EXAMPLE 15, Step A. Mass spectrum (ESI) 324.2 (M+1).

Step B. 4-(5-Cyano-7-isopropenyl-1,3-benzoxazol-2-yl)-N-({1-[5-(trifluoromethyl)pyridin-2-yl]piperidin-4-yl}methyl)benzamide The title compound was prepared following a procedure analogous to that described for EXAMPLE 107. Mass spectrum (ESI) 546.2 (M+1). $^1$H NMR (500 MHz, CDCl$_3$): δ 8.39 (s, 1H), 8.33 (d, J=8.4 Hz, 2H), 8.00 (s, 1H), 7.95 (d, J=8.5 Hz, 2H), 7.67 (s, 1H), 7.61 (d, J=9.0 Hz, 1H), 6.65 (d, J=8.9 Hz, 1H), 6.30 (t, J=6.0 Hz, 1H), 5.98 (s, 1H), 5.60 (s, 1H), 4.46 (d, J=13.3 Hz, 2H), 3.44 (t, J=6.4 Hz, 2H), 2.94 (t, J=10.9 Hz, 2H), 2.34 (s, 3H), 2.03 (m, 1H), 1.90 (d, J=11.2 Hz, 2H), 1.31 (qd, J=12.8, 4.2 Hz, 2H).

Intermediate 24

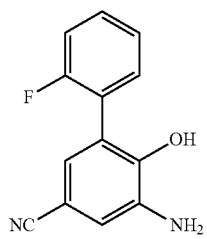 [SMILES: N#Cc1cc(N)c(O)c(-c2ccccc2F)c1]

5-Amino-2'-fluoro-6-hydroxybiphenyl-3-carbonitrile

Step A. 2'-Fluoro-6-hydroxy-5-nitrobiphenyl-3-carbonitrile

To a mixture of 4-hydroxy-3-iodo-5-nitrobenzonitrile (870 mg) and 2-fluorophenylboronic acid (630 mg) in acetone (50 ml) and water (12.5 ml) was added the palladium(II) acetate (73 mg) and potassium carbonate (830 mg). The reaction was then heated for 18 h at 60° C. The mixture was then concentrated in vacuo and filtered through a plug of silica gel, eluting with ethyl acetate. The eluent was concentrated in vacuo and the residue was purified via flash chromatography on a Biotage Horizon, 40 M column, eluting with 1 column volume of 100% hexanes, followed by a gradient of 0-40% ethyl acetate in hexanes over 10 column volumes to provide the title compound (668 mg, 86%). Mass spectrum (ESI) 257.1 (M-1).

Step B. 5-Amino-2'-fluoro-6-hydroxybiphenyl-3-carbonitrile

To a suspension of charcoal (283 mg) in 25 ml of methanol was added iron (III) chloride hexahydrate (35 mg), and 2'-fluoro-6-hydroxy-5-nitrobiphenyl-3-carbonitrile (668 mg). The resultant green mixture was heated under nitrogen at 70° C. for 10 min. Hydrazine (403 μl) was added slowly, and the mixture was stirred for 2 h at 70° C. The mixture was then cooled to room temperature and filtered through a plug of Celite. The eluent was concentrated in vacuo to provide the title compound (543 mg, 92%). Mass spectrum (ESI) 229.1 (M+1).

Intermediate 25

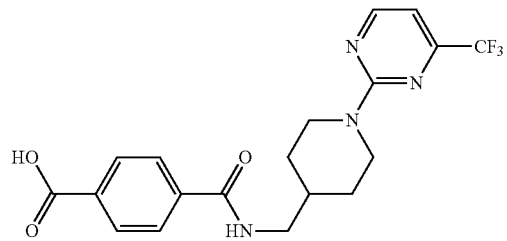 [SMILES: O=C(O)c1ccc(C(=O)NCC2CCN(c3nccc(C(F)(F)F)n3)CC2)cc1]

4-{[({1-[4-(Trifluoromethyl)pyrimidin-2-yl]piperidin-4-yl}methyl)amino]carbonyl}benzoic acid Step A. Methyl 4-{[({1-[4-(trifluoromethyl)pyrimidin-2-yl]piperidin-4-yl}methyl)amino]carbonyl}benzoate 1-{1-[4-(Trifluoromethyl)pyrimidine-2-yl]piperidi-4-yl}methanamine (INTERMEDIATE 6, 1.48 g) and 4-acetylbenzoyl chloride (1.13 g) were dissolved in 200 ml of dioxane and heated to 80° C. for 1 h. The mixture then was cooled to room temperature, and the dioxane was removed in vacuo. The residue was dissolved in 150 ml of ethyl acetate and extracted with a 150 ml of a saturated aqueous solution of potassium carbonate. The product was extracted from the aqueous layer with ethyl acetate (3×100 ml). The organic layers were combined and concentrated in vacuo and the residue was purified via flash chromatography on a Biotage Horizon, 65i column, eluting with 1 column volume of 100% hexanes, followed by a gradient of 0-100% ethyl acetate in hexanes over 10 column volumes to provide the title compound (1.23 g, 51%). Mass spectrum (ESI) 423.3 (M+1).

Step B. 4-{[({1-[4-(Trifluoromethyl)pyrimidin-2-yl]piperidin-4-yl}methyl)amino]carbonyl}benzoic acid Methyl 4-{[({1-[4-(trifluoromethyl)pyrimidin-2-yl]piperidin-4-yl}methyl)amino]carbonyl}benzoate was dissolved in 24 ml of tetrahydrofuran, 23 ml of methanol, and 23 ml of water. To this solution was added lithium hydroxide (817 mg) and the mixture was stirred at 50° C. for 1.25 h. The solvents were removed in vacuo and the residue was taken up in 1 N HCl (70 ml) and 70 ml of ethyl acetate. The mixture was sonicated until the solid residue mostly dissolved in the ethyl acetate. The two phases were separated, and any remaining product in the aqueous layer was extracted out with ethyl acetate (70 ml). The organic layers were combined, washed with brine (20 ml), and concentrated in vacuo to yield the title compound (1.09 g, 81%). Mass spectrum (ESI) 409.1 (M+1).

Example 109

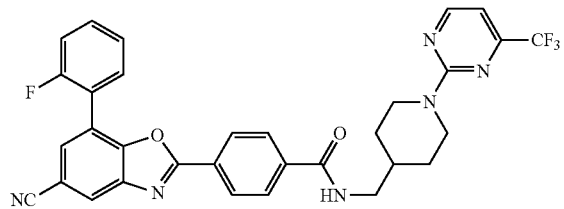 [SMILES: N#Cc1cc(-c2ccccc2F)c2oc(-c3ccc(C(=O)NCC4CCN(c5nccc(C(F)(F)F)n5)CC4)cc3)nc2c1]

4-[5-Cyano-7-(2-fluorophenyl)-1,3-benzoxazol-2-yl]-N-({1-[4-(trifluoromethyl)pyrimidin-2-yl]piperidin-4-yl}methyl)benzamide To of 4-{[({1-[4-(trifluoromethyl)pyrimidin-2-yl]piperidin-4-yl}methyl)amino]carbonyl}benzoic acid (INTERMEDIATE 25, 100 mg) in 4 ml of dichloromethane was slowly added oxalyl chloride (600 μl, 2M in dichloromethane) followed by dimethylformamide (10 □l). The mixture was stirred for 15 min to completely dissolve the carboxylic acid. The solution was then concentrated in vacuo and redissolved in 35 ml of dioxane. To the resultant acyl chloride was added 5-amino-2'-fluoro-6-hydroxybiphenyl-3-carbonitrile (INTERMEDIATE 24, 59 mg). The mixture was heated at 80° C. for 1 h, and then cooled to room temperature. The dioxane was removed in vacuo, and to the residue was added 45 ml of toluene and 46 mg of p-toluenesulfonic acid monohydrate (46 mg). The solution was heated to 140° C. and stirred at this temperature for 15 h. The reaction mixture was then cooled to room temperature, and the solvent was removed in vacuo. The residue was purified via column chromatography using a Biotage Horizon, 40 M column, eluting with 1 column volume of 100% hexanes followed by a gradient of 0 to 50% ethyl acetate in hexanes over 10 column volumes, followed by 100% ethyl acetate for 4 column volumes to provide the title compound (20 mg, 14%). Mass spectrum (ESI) 601.2 (M+2). $^1$H NMR (500 MHz, CDCl$_3$): δ 8.48 (d, J=4.8 Hz, 1H), 8.31 (d, J=8.2 Hz, 2H), 8.12 (s, 1H), 7.93 (d, J=8.4 Hz, 2H), 7.80 (s, 1H), 7.65 (t, J=5.7 Hz, 1H), 7.54 (m, 1H), 7.37 (t, J=7.6 Hz, 1H), 7.32 (t, J=9.7 Hz, 1H), 6.73 (d, J=4.8 Hz, 1H), 6.30 (bs, 1H), 4.87 (d, J=13.5 Hz, 2H), 3.44 (t, J=6.5 Hz, 2H), 2.94 (t, J=13.5 Hz, 2H), 2.01 (m, 1H), 1.90, (d, J=13.0 Hz, 2H), 1.31 (qd, J=12.5 Hz, 3.9 Hz, 2H).

Intermediate 26

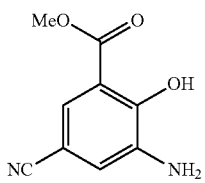 [SMILES: COC(=O)c1cc(C#N)cc(N)c1O]

Methyl 3-amino-5-cyano-2-hydroxybenzoate

Step A. Methyl 5-cyano-2-hydroxy-3-nitrobenzoate

To 25 ml of fuming nitric acid was added 2.50 g of methyl 5-cyano-2-hydroxybenzoate. This solution quickly turned dark orange, and the reaction was complete after stirring for 1 h. The solution was slowly transferred to 100 ml of ice-cold water. To the resultant suspension was added 100 ml of ethyl acetate and the biphasic mixture was shaken and separated. The aqueous layer was extracted with ethyl acetate (2×60 ml), and the combined organics were dried over sodium sulfate, filtered, and concentrated in vacuo. The residue was taken up in ethyl acetate (100 ml) and filtered through a small plug of silica gel, eluting with more ethyl acetate (50 ml). The eluent was concentrated in vacuo to provide the title compound (2.71 g, 87%). Mass spectrum (ESI) 221.2 (M−1).

Step B. Methyl 3-amino-5-cyano-2-hydroxybenzoate

To a mixture of 2.71 g of methyl 5-cyano-2-hydroxy-3-nitrobenzoate in a 60 ml of methanol and 40 ml of tetrahydrofuran was added palladium on carbon (500 mg, 10% wet). This suspension was purged with, and stirred under, an atmosphere of hydrogen (via balloon) for 4 h at 50° C. The mixture was then filtered through a plug of Celite, eluting with ethyl acetate (75 ml). The eluent was concentrated in vacuo and the residue was taken up in ethyl acetate (50 ml) and methanol (as needed to dissolve) and was then filtered through a plug of silica gel. The eluent was concentrated in vacuo again and purified via column chromatography using a Biotage Horizon, 65i column, eluting with 1 column volume of 100% hexanes followed by a gradient of 0 to 100% ethyl acetate in hexanes over 10 column volumes, followed by 2 column volumes of 100% ethyl acetate to provide the title compound (1.83 g, 78%). Mass spectrum (ESI) 190.9 (M−1).

Intermediate 27

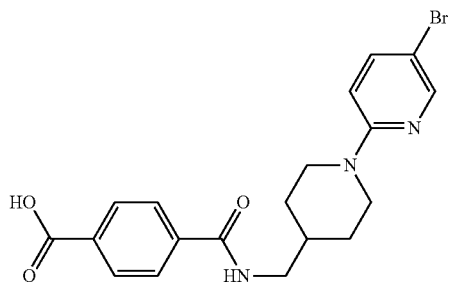 [SMILES: O=C(O)c1ccc(C(=O)NCC2CCN(c3ccc(Br)cn3)CC2)cc1]

4-[({[1-(5-bromopyridin-2-yl)piperidin-4-yl]methyl}amino)carbonyl]benzoic acid

The title compound was prepared using a procedure analogous to that described for INTERMEDIATE 25. Mass spectrum (ESI) 419.8 (M+1).

Example 110

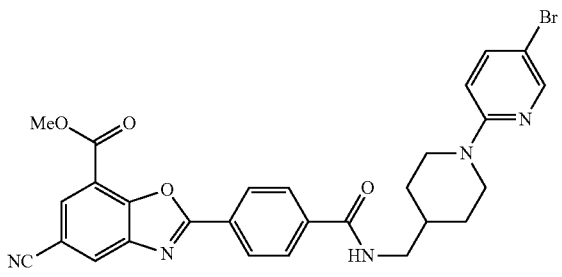 [SMILES: COC(=O)c1cc(C#N)cc2nc(-c3ccc(C(=O)NCC4CCN(c5ccc(Br)cn5)CC4)cc3)oc12]

Methyl 2-{4-[({[1-(5-bromopyridin-2-yl)piperidin-4-yl]methyl}amino)carbonyl]phenyl}-5-cyano-1,3-benzoxazole-7-carboxylate The title compound was prepared following a procedure analogous to that described for EXAMPLE 109. Mass spectrum (ESI) 576.0 (M+2). $^1$H NMR (500 MHz, CDCl$_3$): δ 8.40 (d, J=8.5 Hz, 2H), 8.32 (s, 1H), 8.26 (s, 1H), 7.97 (d, J=8.5 Hz, 2H), 7.93 (s, 1H), 7.50 (d, J=9.3 Hz, 1H), 6.55 (d, J=9.2 Hz, 1H), 6.32 (t, J=5.4 Hz, 1H), 4.43 (d, J=13.4 Hz, 2H), 4.09 (s, 3H), 3.44 (t, J=6.5 Hz, 3H), 2.88 (td, J=13.4 Hz, 2.1 Hz, 2H), 1.96 (m, 1H), 1.90, (d, J=12.8 Hz, 2H), 1.34 (qd, J=12.6 Hz, 3.9 Hz, 2H).

Example 111

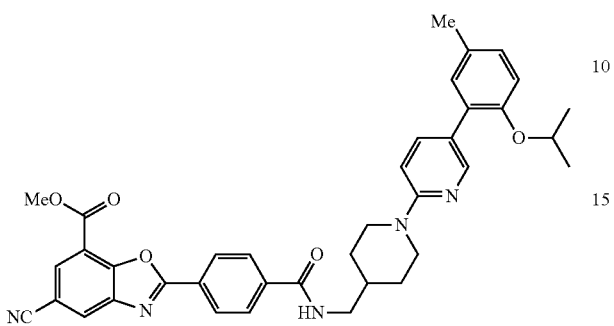

Methyl 5-cyano-2-(4-{[({1-[5-(2-isopropoxy-5-methylphenyl)pyridin-2-yl]piperidin-4-yl}methyl)amino]carbonyl}phenyl)-1,3-benzoxazole-7-carboxylate The title compound was prepared in a procedure analogous to that described for EXAMPLE 15, using only toluene and methanol as co-solvents. Mass spectrum (ESI) 644.3 (M+2). $^1$H NMR (500 MHz, CDCl$_3$): δ 8.41 (d, J=8.5 Hz, 2H), 8.37 (d, J=2.3 Hz, 1H), 8.32 (s, 1H), 8.26 (s, 1H), 7.98 (d, J=8.5 Hz, 2H), 7.73 (dd, J=8.9 Hz, 2.3 Hz, 1H), 7.10 (s, 1H), 7.04 (t, J=5.0 Hz, 1H), 6.87 (d, J=8.3 Hz, 1H), 6.71 (d, J=8.9 Hz, 1H), 6.32 (bs, 1H), 4.39 (m, 3H), 4.10 (s, 3H), 3.47 (t, J=6.4 Hz, 2H), 2.89 (td, J=13.2 Hz, 2.3 Hz, 2H), 2.32 (s, 3H), 1.92 (m, 1H), 1.91, (d, J=13.5 Hz, 2H), 1.43 (qd, J=12.9 Hz, 3.2 Hz, 2H), 1.24 (d, 6.2 Hz, 6H).

Example 112

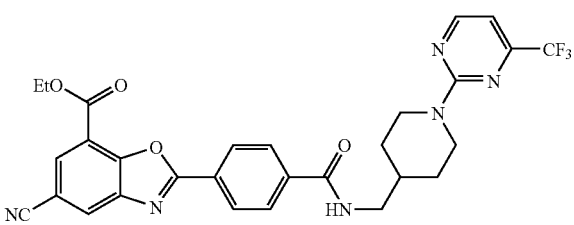

Ethyl 5-cyano-2-(4-{[({1-[4-(trifluoromethyl)pyrimidin-2-yl]piperidin-4-yl}methyl)amino]carbonyl}phenyl)-1,3-benzoxazole-7-carboxylate Step A. Ethyl 3-amino-5-cyano-2-hydroxybenzoate The title compound was prepared using a procedure analogous to that described for INTERMEDIATE 26. Mass spectrum (ESI) 205.2 (M−1).

Step B. Ethyl 5-cyano-2-(4-{[({1-[4-(trifluoromethyl)pyrimidin-2-yl]piperidin-4-yl}methyl)amino]carbonyl}phenyl)-1,3-benzoxazole-7-carboxylate The title compound was prepared using a procedure analogous to that described for EXAMPLE 109. Mass spectrum (ESI) 579.2 (M+2). $^1$H NMR (500 MHz, CDCl$_3$): δ 8.49 (d, J=4.6 Hz, 1H), 8.40 (d, J=8.4 Hz, 2H), 8.32 (s, 1H), 8.24 (s, 1H), 7.98 (d, J=8.5 Hz, 2H), 6.75 (d, J=4.8 Hz, 1H), 6.33 (t, J=5.8 Hz, 1H), 4.88 (d, J=13.5 Hz, 2H), 4.68 (q, J=7.1 Hz, 2H), 3.44 (t, J=6.6 Hz, 3H), 2.96 (td, J=13.4 Hz, 2.7 Hz, 2H), 2.00 (m, 1H), 1.89, (d, J=13.0 Hz, 2H), 1.49 (t, J=7.1 Hz, 3H), 1.32 (qd, J=12.8 Hz, 3.4 Hz, 2H).

Example 113

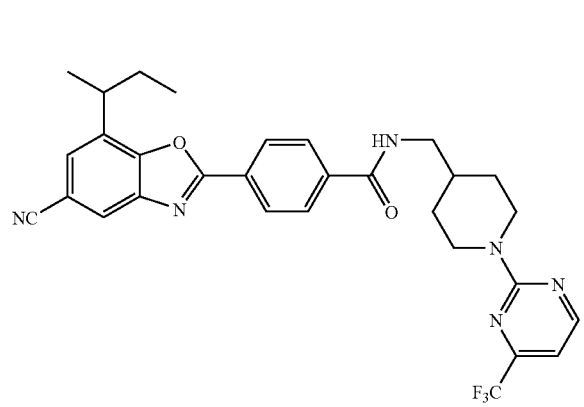

4-(7-sec-Butyl-5-cyano-1,3-benzoxazol-2-yl)-N-({1-[4-(trifluoromethyl)pyrimidin-2-yl]piperidin-4-yl}methyl)benzamide Step A: 4-(7-Bromo-5-cyano-1,3-benzoxazol-2-yl)-N-({1-[4-(trifluoromethyl)pyrimidin-2-yl]piperidin-4-yl}methyl)benzamide The title compound was prepared from 4-{[({1-[4-(trifluoromethyl)pyrimidin-2-yl]piperidin-4-yl}methyl)amino]carbonyl}benzoic acid (INTERMEDIATE 25) and 3-amino-5-bromo-4-hydroxybenzonitrile (INTERMEDIATE 1, Step B) by a procedure analogous to that described in Example 109. Mass spectrum (ESI) 587.0 (M+3).

Step B: 4-{5-Cyano-7-[(1Z)-1-methylprop-1-en-1-yl]-1,3-benzoxazol-2-yl}-N-({1-[4-(trifluoromethyl)pyrimidin-2-yl]piperidin-4-yl}methyl)benzamide A mixture of 4-(7-bromo-5-cyano-1,3-benzoxazol-2-yl)-N-({1-[4-(trifluoromethyl)pyrimidin-2-yl]piperidin-4-yl}methyl)benzamide (30 mg, 0.051 mmol), [(1E)-1-methylprop-1-en-1-yl]boronic acid (18 mg, 0.18 mmol), potassium carbonate (3M solution in water) (150 µl), and 1,1'-bis(di-t-butylphosphino)-ferrocene palladium chloride (2 mg, 0.0031 mmol) in tetrahydrofuran (5 ml) was heated at reflux overnight. The mixture was diluted with ethyl acetate, filtered, and concentrated in vacuo. The residue was purified by flash column chromatography to afford the title compound. Mass spectrum (ESI) 561.2 (M+1).

Step C: 4-(7-sec-Butyl-5-cyano-1,3-benzoxazol-2-yl)-N-({1-[4-(trifluoromethyl)pyrimidin-2-yl]piperidin-4-yl}methyl)benzamide To a mixture of 4-{5-cyano-7-[(1Z)-1-methylprop-1-en-1-yl]-1,3-benzoxazol-2-yl}-N-({1-[4-(trifluoromethyl)pyrimidin-2-yl]piperidin-4-yl}methyl)benzamide (18 mg) in ethyl acetate (5 ml)/dichloromethane (5 ml)/methanol (5 ml) at 40° C. was added 15 mg of 10% Pd/C and the resulting mixture was degassed and flushed with nitrogen, followed by degassing and flushing with hydrogen using a double balloon. The mixture was stirred under hydrogen at 40° C. overnight, and then filtered, washing with ethyl acetate. The filtrate was concentrated and purified by flash column chromatography on a Biotage Horizon, 25M Si column, eluting with 1 column volume of 10% ethyl acetate in hexanes, followed by a linear gradient of ethyl acetate in hexanes from 10% to 100% over 10 column volumes to afford the title compound. Mass spectrum (ESI) 563.2 (M+1). $^1$H NMR (500 MHz, CDCl$_3$) δ: 8.47 (d, J=4.8 Hz, 1H), 8.34 (d, J=8.2 Hz, 2H), 7.95 (d, J=8.7 Hz, 2H), 7.49 (s, 1H), 6.73 (d, J=4.8 Hz, 1H), 6.32 (t, J=5.9 Hz, 1H), 4.87 (d, J=13.3 Hz, 2H), 3.44 (t, J=6.7 Hz, 2H), 3.21 (m, 1H), 2.93 (m, 2H), 2.01 (m, 1H), 1.90 (m, 2H), 1.84 (m, 2H), 1.44 (d, J=7.1 Hz, 3H), 1.31 (m, 2H), 0.91 (t, J=8.0 Hz, 3H).

Example 114

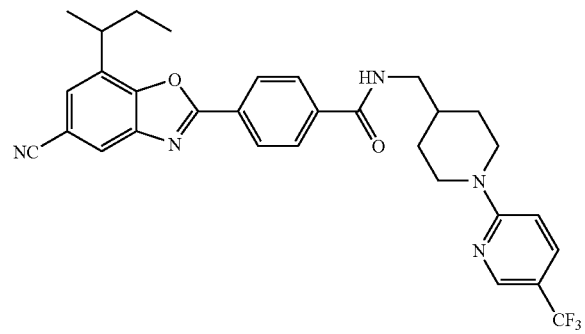

4-(7-sec-Butyl-5-cyano-1,3-benzoxazol-2-yl)-N-({1-[5-(trifluoromethyl)pyridin-2-yl]piperidin-4-yl}methyl)benzamide Step A: 4-{[(4-Carboxybenzoyl)amino]methyl}-1-[5-(trifluoromethyl)pyridin-2-yl]piperidinium chloride The title compound was prepared by a procedure analogous to that described in INTERMEDIATE 25. Mass spectrum (ESI) 408.2 (M+1).

Step B: 4-(7-Bromo-5-cyano-1,3-benzoxazol-2-yl)-N-({1-[5-(trifluoromethyl)pyridin-2-yl]piperidin-4-yl}methyl)benzamide The title compound was prepared from 4-{[(4-carboxybenzoyl)amino]methyl}-1-[5-(trifluoromethyl)pyridin-2-yl]piperidinium chloride and 3-amino-5-bromo-4-hydroxybenzonitrile (INTERMEDIATE 1, Step B) by a procedure analogous to that described in EXAMPLE 109. Mass spectrum (ESI) 585.9 (M+3).

Step C: 4-{5-Cyano-7-[(1Z)-1-methylprop-1-en-1-yl]-1,3-benzoxazol-2-yl}-N-({1-[5-(trifluoromethyl)pyridin-2-yl]piperidin-4-yl}methyl)benzamide The title compound was prepared from 4-(7-bromo-5-cyano-1,3-benzoxazol-2-yl)-N-({1-[5-(trifluoromethyl)pyridin-2-yl]piperidin-4-yl}methyl)benzamide and [(1E)-1-methylprop-1-en-1-yl]boronic acid by a procedure analogous to that described in EXAMPLE 113, Step B. Mass spectrum (ESI) 560.2 (M+1).

Step D: 4-(7-sec-Butyl-5-cyano-1,3-benzoxazol-2-yl)-N-({1-[5-(trifluoromethyl)pyridin-2-yl]piperidin-4-yl}methyl)benzamide The title compound was prepared from 4-{5-cyano-7-[(1Z)-1-methylprop-1-en-1-yl]-1,3-benzoxazol-2-yl}-N-({1-[5-(trifluoromethyl)pyridin-2-yl]piperidin-4-yl}methyl)benzamide by a procedure analogous to that described in EXAMPLE 113, Step C. Mass spectrum (ESI) 562.2 (M+1). $^1$H NMR (500 MHz, CDCl$_3$) δ: 8.38 (s, 1H), 8.35 (d, J=8.5 Hz, 2H), 7.95 (m, 3H), 7.61 (dd, J=2.3 Hz, J=8.9 Hz, 1H), 7.49 (s, 1H), 6.65 (d, J=9.2 Hz, 1H), 6.32 (t, J=5.9 Hz, 1H), 4.46 (d, J=13.5 Hz, 2H), 3.44 (t, J=6.6 Hz, 2H), 3.21 (m, 1H), 2.94 (m, 2H), 2.00 (m, 1H), 1.90 (m, 2H), 1.83 (m, 2H), 1.44 (d, J=7.1 Hz, 3H), 1.36 (m, 2H), 0.91 (t, J=7.6 Hz, 3H).

Example 115

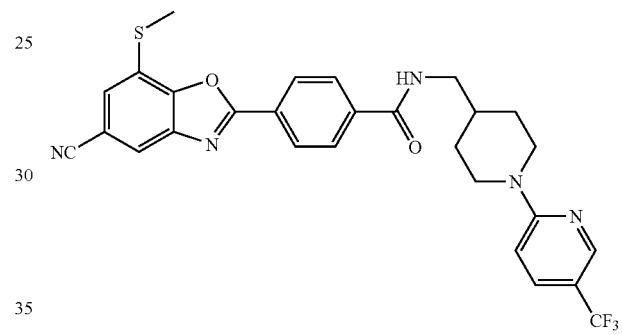

4-[5-Cyano-7-(methylthio)-1,3-benzoxazol-2-yl]-N-({1-[5-(trifluoromethyl)pyridin-2-yl]piperidin-4-yl}methyl)benzamide Step A: 4-Hydroxy-3-(methylthio)benzonitrile To a solution of 3-amino-4-hydroxybenzonitrile (1.00 g, 7.46 mmol) in dioxane (15 ml) was added t-butyl nitrite (1.12 ml, 14.9 mmol) and the resulting mixture was stirred under nitrogen at room temperature for 15 min. Dimethyl disulfide (5 ml) was then added and the resulting mixture was heated to 90° C. for 3 h. The reaction mixture was purified by flash column chromatography to afford the title compound. Mass spectrum (ESI) 164.1 (−1).

Step B: 4-Hydroxy-3-(methylthio)-5-nitrobenzonitrile

The title compound was prepared from 4-hydroxy-3-(methylthio)benzonitrile by a procedure analogous to that described in INTERMEDIATE 1, Step A. Mass spectrum (ESI) 210.1 (M−1).

Step C: 3-Amino-4-hydroxy-5-(methylthio)benzonitrile

The title compound was prepared from 4-hydroxy-3-(methylthio)-5-nitrobenzonitrile by a procedure analogous to that described in EXAMPLE 113, Step C. Mass spectrum (ESI) 210.1 (M−1).

77

Step D: Methyl 4-[5-cyano-7-(methylthio)-1,3-benzoxazol-2-yl]benzoate

The title compound was prepared from 3-amino-4-hydroxy-5-(methylthio)benzonitrile and methyl 4-(chlorocarbonyl)benzoate by a procedure analogous to that described in INTERMEDIATE 1, Step C. Mass spectrum (ESI) 325.0 (M+1).

Step E: 4-[5-Cyano-7-(methylthio)-1,3-benzoxazol-2-yl]benzoic acid

The title compound was prepared from methyl 4-[5-cyano-7-(methylthio)-1,3-benzoxazol-2-yl]benzoate by a procedure analogous to that described in INTERMEDIATE 2, Step C. Mass spectrum (ESI) 311.0 (M+1).

Step F: 4-[5-Cyano-7-(methylthio)-1,3-benzoxazol-2-yl]-N-({1-[5-(trifluoromethyl)pyridin-2-yl]piperidin-4-yl}methyl)benzamide The title compound was prepared from 4-[5-cyano-7-(methylthio)-1,3-benzoxazol-2-yl]benzoic acid and 1-{1-[5-(trifluoromethyl)pyridin-2-yl]piperidin-4-yl}methanamine (INTERMEDIATE 5) by a procedure analogous to that described in EXAMPLE 35. Mass spectrum (ESI) 552.0 (M+1). $^1$H NMR (500 MHz, CDCl$_3$) δ: 8.38 (s, 1H), 8.35 (d, J=8.3 Hz, 2H), 7.94 (d, J=8.3 Hz, 2H), 7.89 (s, 1H), 7.60 (dd, J=2.3 Hz, J=9.2 Hz, 1H), 7.45 (s, 1H), 6.65 (d, J=9.1 Hz, 1H), 6.32 (t, J=5.9 Hz, 1H), 4.46 (d, J=13.3 Hz, 2H), 3.44 (t, J=6.4 Hz, 2H), 2.94 (m, 2H), 2.70 (s, 3H), 1.99 (m, 1H), 1.90 (br d, J=11.6 Hz, 2H), 1.34 (m, 2H).

Example 116

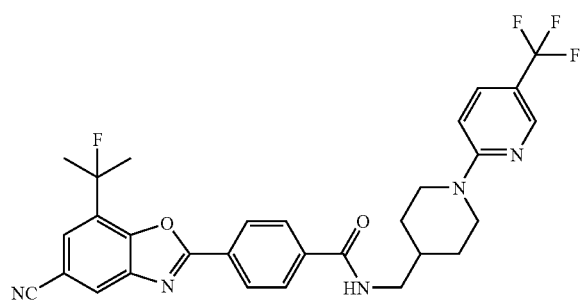

4-[5-Cyano-7-(1-fluoro-1-methylethyl)-1,3-benzoxazol-2-yl]-N-({1-[5-(trifluoromethyl)pyridin-2-yl]piperidin-4-yl}methyl)benzamide Step A: Methyl 2-(4-bromophenyl)-5-cyano-1,3-benzoxazole-7-carboxylate The title compound was prepared from 4-bromobenzoyl chloride and methyl 3-amino-5-cyano-2-hydroxybenzoate (INTERMEDIATE 26) by a procedure analogous to that described in INTERMEDIATE 1, Step C. Mass spectrum (ESI) 358.9 (M+3).

Step B: 2-(4-Bromophenyl)-7-(1-hydroxy-1-methylethyl)-1,3-benzoxazole-5-carbonitrile To a solution of 2-(4-bromophenyl)-5-cyano-1,3-benzoxazole-7-carboxylate (451 mg, 1.263 mmol) in tetrahydrofuran (60 ml) at 0° C. was added methyl magnesium bromide (3.16 ml, 4.42 mmol). The resulting solution was warmed slowly to room temperature and stirred at this temperature overnight. The reaction mixture was concentrated, and the residue was preadsorbed on silica gel and purified by flash column chromatography eluting with ethyl acetate in hexanes to afford the title compound. Mass spectrum (ESI) 358.9 (M+3).

Step C: 2-(4-Bromophenyl)-7-(1-fluoro-1-methylethyl)-1,3-benzoxazole-5-carbonitrile To a mixture of 4-bromophenyl)-7-(1-hydroxy-1-methylethyl)-1,3-benzoxazole-5-carbonitrile (327 mg, 0.915 mmol) in dichloromethane (50 ml) was added diethylaminosulfur trifluoride (0.605 ml, 4.58 mmol), and the resulting solution was stirred under nitrogen overnight. The reaction mixture was concentrated and purified by flash column chromatography eluting with ethyl acetate in hexanes. The product was crystallized from hexanes-ethyl acetate to afford the title compound. Mass spectrum (ESI) 360.9 (M+3).

Step D: Methyl 4-[5-cyano-7-(1-fluoro-1-methylethyl)-1,3-benzoxazol-2-yl]benzoate A mixture of 2-(4-bromophenyl)-7-(1-fluoro-1-methylethyl)-1,3-benzoxazole-5-carbonitrile (66.9 mg, 0.186 mmol), palladium acetate (8.36 mg, 0.037 mmol), triethylamine (0.194 ml, 1.38 mmol), and 1,3-bis(diphenylphosphino)propane (17.67 mg, 0.043 mmol) in dimethylformamide (3 ml) and methanol (3 ml) was stirred for 71 h at 60° C. under 50-66 psi of carbon monoxide. The product precipitated upon cooling. The precipitate was filtered, washing with methanol to afford the title compound. Mass spectrum (ESI) 339.0 (M+1).

Step E: 4-[5-Cyano-7-(1-fluoro-1-methylethyl)-1,3-benzoxazol-2-yl]-N-({1-[5-(trifluoromethyl)pyridin-2-yl]piperidin-4-yl}methyl)benzamide To a stirred solution of methyl 4-[5-cyano-7-(1-fluoro-1-methylethyl)-1,3-benzoxazol-2-yl]benzoate (29 mg, 0.086 mmol) in tetrahydrofuran (6 ml) at room temperature under nitrogen was added potassium trimethylsilanolate (36.7 mg, 0.257 mmol), and the resulting dark orange solution was stirred overnight. It was then concentrated in vacuo. To the residue was added dichloromethane (6 ml), oxalyl chloride (2M solution in dichloromethane) (0.257 ml, 0.514 mmol), and 1 drop of dimethylformamide. The mixture was stirred at room temperature for 1 h, and then concentrated in vacuo. To the residue was added tetrahydrofuran (6 ml), 1-{1-[5-(trifluoromethyl)pyridin-2-yl]piperidin-4-yl}methanamine (INTERMEDIATE 5, 33.3 mg, 0.129 mmol), and diisopropylethylamine (0.149 ml, 0.857 mmol). The reaction mixture was stirred at room temperature overnight, concentrated in vacuo, and purified by flash column chromatography. The recovered solid was triturated with hot methanol to afford the title compound. Mass spectrum (ESI) 566.2 (M+1). $^1$H NMR (500 MHz, CDCl$_3$) δ: 8.38 (s, 1H), 8.32 (d, J=8.5 Hz, 2H), 8.04 (s, 1H), 7.95 (d, J=8.4 Hz, 2H), 7.76 (s, 1H), 7.61 (dd, J=2.5 Hz, J=9.2 Hz, 1H), 6.65 (d, J=9.2 Hz, 1H), 6.32 (t, J=5.9 Hz, 1H), 4.46 (d, J=13.4 Hz, 2H), 3.44 (t, J=6.4 Hz, 2H), 2.94

(m, 2H), 2.00 (m, 1H), 1.96 (s, 3H), 1.91 (s, 3H), 1.90 (br d, J=12.6 Hz, 2H), 1.34 (m, 2H).

Example 117

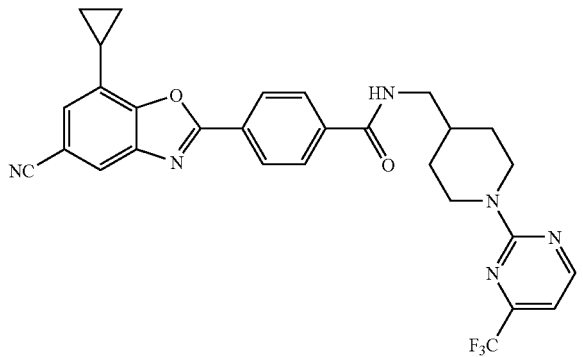

4-(5-Cyano-7-cyclopropyl-1,3-benzoxazol-2-yl)-N-({1-[4-(trifluoromethyl)pyrimidin-2-yl]piperidin-4-yl}methyl)benzamide A mixture of 4-(7-bromo-5-cyano-1,3-benzoxazol-2-yl)-N-({1-[4-(trifluoromethyl)pyrimidin-2-yl]piperidin-4-yl}methyl)benzamide (EXAMPLE 113, Step A) (59 mg, 0.10 mmol), cyclopropylboronic acid (86 mg, 1.0 mmol), potassium carbonate (138 mg, 1.0 mmol), and tetrakis(triphenylphosphine)palladium(0) (12 mg, 0.01 mmol) in dimethoxyethane (7 ml)/water (0.7 ml) was heated to reflux and stirred at this temperature for 4 d. The mixture was diluted with ethyl acetate, filtered, and concentrated. The residue was purified by flash column chromatography to afford the title compound. Mass spectrum (ESI) 547.2 (M+1). $^1$H NMR (500 MHz, DMSO-$d_6$) δ: 8.77 (t, J=5.5 Hz, 1H), 8.65 (d, J=4.8 Hz, 1H), 8.31 (d, J=8.2 Hz, 2H), 8.18 (s, 1H), 8.08 (d, J=8.3 Hz, 2H), 7.56 (s, 1H) 6.96 (d, J=4.8 Hz, 1H), 5.74 (s, 1H), 4.65 (br d, J=12.6 Hz, 2H), 3.22 (t, J=6.2 Hz, 2H), 2.95 (t, J=12.4 Hz, 2H), 2.40 (m, 1H), 1.93 (m, 1H), 1.81 (br d, J=11.9 Hz, 2H), 1.15 (m, 5H).

Example 118

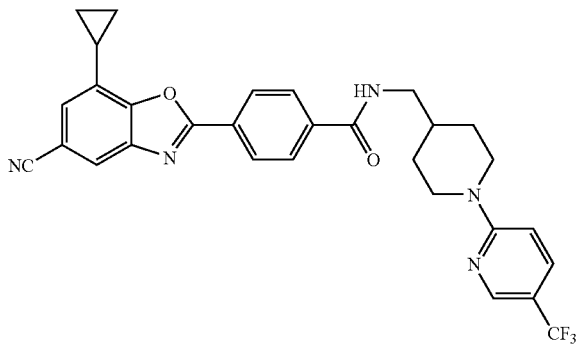

4-(5-Cyano-7-cyclopropyl-1,3-benzoxazol-2-yl)-N-({1-[5-(trifluoromethyl)pyridin-2-yl]piperidin-4-yl}methyl)benzamide The title compound was prepared from 4-(7-bromo-5-cyano-1,3-benzoxazol-2-yl)-N-({1-[5-(trifluoromethyl)pyridin-2-yl]piperidin-4-yl}methyl)benzamide (EXAMPLE 114, Step B) and cyclopropylboronic acid by a procedure analogous to that described in EXAMPLE 117. Mass spectrum (ESI) 546.3 (M+1). $^1$H NMR (500 MHz, CDCl$_3$) δ: 8.38 (s, 1H), 8.33 (d, J=8.3 Hz, 2H), 7.95 (d, J=8.1 Hz, 2H), 7.86 (s, 1H), 7.60 (br d, J=8.9 Hz, 1H), 7.23 (s, 1H), 6.65 (d, J=8.9 Hz, 1H), 6.38 (br s, 1H), 4.46 (d, J=13.1 Hz, 2H), 3.44 (t, J=6.4 Hz, 2H), 2.93 (t, J=12.1 Hz, 2H), 2.33 (m, 1H), 2.00 (m, 1H), 1.90 (d, J=12.3 Hz, 2H), 1.33 (m, 2H), 1.22 (m, 2H), 1.06 (m, 2H).

Example 119

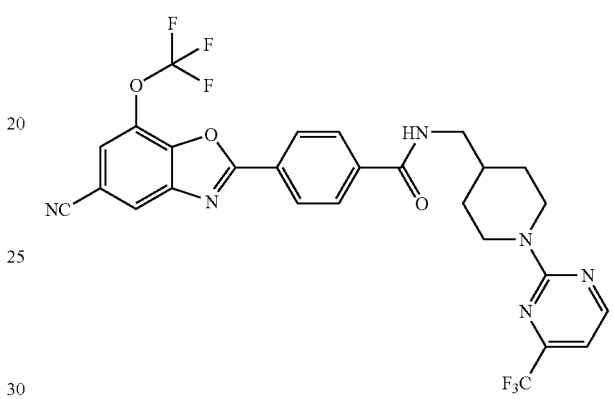

4-[5-Cyano-7-(trifluoromethoxy)-1,3-benzoxazol-2-yl]-N-({1-[4-(trifluoromethyl)pyrimidin-2-yl]piperidin-4-yl}methyl)benzamide Step A: 4-Hydroxy-3-(trifluoromethoxy)benzoic acid To a 0° C. solution of 4-hydroxy-3-(trifluoromethoxy)benzaldehyde (901 mg, 4.37 mmol) in acetone (10 ml) was added 4 ml of the Jones reagent. The ice bath was removed and the reaction was stirred at room temperature for ca. 1 h. Isopropanol was added to destroy the excess Jones reagent. The mixture was diluted with ethyl acetate, the precipitate was filtered off, and the filtrate concentrated in vacuo. The residue was diluted with 1M HCl and extracted 3 times with ethyl acetate. The combined organics were washed with brine, dried over sodium sulfate, and concentrated in vacuo to afford the title compound. Mass spectrum (ESI) 221.1 (M−1).

Step B: 4-Hydroxy-3-(trifluoromethoxy)benzamide

To a solution of 4-hydroxy-3-(trifluoromethoxy)benzoic acid (841 mg, 3.79 mmol) in dimethylformamide (10 ml) were added (benzotriazol-1-yloxy)tris(dimethylamino)phosphonium hexafluorophosphate (1.84 g, 4.17 mmol), hydroxybenzotriazole hydrate (563 mg, 4.17 mmol), diisopropylethylamine (1.99 ml, 11.4 mmol), and ammonium chloride (405 mg, 7.58 mmol). The resulting solution was stirred at room temperature for 2 h, and then diluted with ethyl acetate and washed with 0.5 M HCl and brine (2×). The organic layer was dried over sodium sulfate and concentrated in vacuo. The residue was purified by flash column chromatography using a Horizon Biotage, 65i Si column, eluting with 1 column volume of dichloromethane, followed by a linear gradient of ethyl acetate in dichloromethane from 0% to 100% over 10 column volumes to afford the title compound. Mass spectrum (ESI) 222.1 (M+1).

Step C: 4-Hydroxy-3-(trifluoromethoxy)benzonitrile

To a solution of 4-hydroxy-3-(trifluoromethoxy)benzamide (532 mg, 2.41 mmol) in dimethylformamide (3 ml) was added cyanuric chloride (223 mg, 1.21 mmol). The mixture was stirred for 25 and then water was added and the resulting solution was extracted 3 times with ethyl acetate. The combined organics were washed with brine, dried over sodium sulfate, and concentrated in vacuo to afford the title compound. Mass spectrum (ESI) 202.1 (M−1).

Step D: 4-Hydroxy-3-nitro-5-(trifluoromethoxy)benzonitrile

The title compound was prepared from 4-hydroxy-3-(trifluoromethoxy)benzonitrile by a procedure analogous to that described in INTERMEDIATE 1, Step A. Mass spectrum (ESI) 247.1 (M−1).

Step E: 3-Amino-4-hydroxy-5-(trifluoromethoxy)benzonitrile

The title compound was prepared from 4-hydroxy-3-nitro-5-(trifluoromethoxy)benzonitrile by a procedure analogous to that described in EXAMPLE 113, Step C. Mass spectrum (ESI) 219.0 (M+1).

Step F: 4-[5-Cyano-7-(trifluoromethoxy)-1,3-benzoxazol-2-yl]-N-({1-[4-(trifluoromethyl)pyrimidin-2-yl]piperidin-4-yl}methyl)benzamide The title compound was prepared from 3-amino-4-hydroxy-5-(trifluoromethoxy)benzonitrile and 4-{[({1-[4-(trifluoromethyl)pyrimidin-2-yl]piperidin-4-yl}methyl)amino]carbonyl}benzoic acid (INTERMEDIATE 25) by a procedure analogous to that described in EXAMPLE 109. Mass spectrum (ESI) 591.1 (M+1). $^1$H NMR (500 MHz, CDCl$_3$) δ: 8.47 (d, J=4.8 Hz, 1H), 8.36 (d, J=8.2 Hz, 2H), 8.06 (s, 1H), 7.97 (d, J=8.2 Hz, 2H), 7.59 (s, 1H), 6.72 (d, J=4.6 Hz, 1H), 6.33 (t, J=5.9 Hz, 1H), 4.87 (d, J=13.5 Hz, 2H), 3.45 (t, J=6.4 Hz, 2H), 2.93 (m, 2H), 2.00 (m, 1H), 1.90 (br d, J=11.6 Hz, 2H), 1.31 (m, 2H).

Example 120

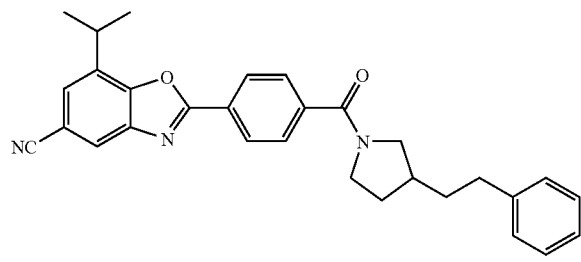

To a solution of 25 mg of 4-(5-cyano-7-isopropyl-1,3-benzoxazol-2-yl)benzoic acid (INTERMEDIATE 2) in dichloromethane (4 ml) at 0° C. was added 200 μL oxalyl chloride, and then 50 μl of dimethylformamide. The reaction was warmed to room temperature and then stirred for two h. The solution was concentrated and then co-concentrated with toluene. The solid was redissolved in dichloromethane, and 40 mg of 3-(2-phenylethyl)pyrrolidine, and 100 μl of diisopropylethylamine were added. The reaction was stirred for 1 h at room temperature, and then was concentrated. The residue was purified using a Biotage Parallex Flex HPLC system to provide the title compound (9 mg, 6.8%). Mass spectrum (ESI) 464.2 (M+1). $^1$H NMR signals are doubled and broadened because of restricted rotation about the amide C—N bond. $^1$H NMR (500 MHz, CDCl$_3$): δ 8.31 (d, J=2.5 Hz, 1H), 8.29 (d, J=3 Hz, 1H), 7.93 (m, 1H), 7.69 (app t, 2H), 7.51 (s, 1H), 7.10-7.33 (m, 5H), 3.90-3.96 (m, 1H), 3.63-3.80 (m, 1H), 3.44-3.54 (m, 3H), 3.07-3.32 (m, 1H), 2.55-2.73 (m, 3H), 2.04-2.27 (m, 2H), 1.81 (m, 1H), 1.58-1.75 (m, 6H), 1.45-1.46 (m, 6H), 1.25 (m, 1H).

Example 121

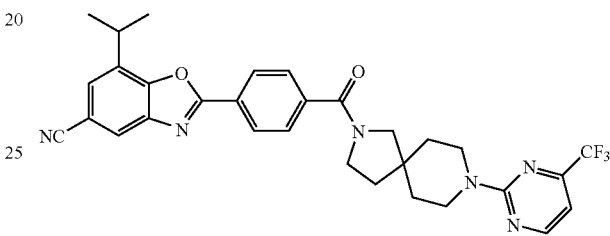

7-Isopropyl-2-[4-({8-[4-(trifluoromethyl)pyrimidin-2-yl]-2,8-diazaspiro[4.5]dec-2-yl}carbonyl)phenyl]-1,3-benzoxazole-5-carbonitrile Step A. tert-Butyl-2-[4-(5-cyano-7-isopropyl-1,3-benzoxazol-2-yl)benzoyl]-2,8-diazaspiro[4.5]decane-8-carboxylate The title compound was synthesized from 4-(5-cyano-7-isopropyl-1,3-benzoxazol-2-yl)benzoic acid (INTERMEDIATE 2) and tert-butyl 2,8-diazaspiro[4.5]decane-8-carboxylate following the procedure described in EXAMPLE 120. Mass spectrum (ESI) 529.2 (M+1).

Step B. 2-[4-(2,8-Diazaspiro[4.5]dec-2-ylcarbonyl)phenyl]-7-isopropyl-1,3-benzoxazole-5-carbonitrile To a solution of tert-butyl-2-[4-(5-cyano-7-isopropyl-1,3-benzoxazol-2-yl)benzoyl]-2,8-diazaspiro[4.5]decane-8-carboxylate (92 mg, 0.174 mmol) in dichloromethane (4 ml) was added trifluoroacetic acid (2 ml, 26.0 mmol). The mixture was stirred for 1 h at 25° C., at which point LC/MS analysis showed the desired amine. The mixture was concentrated and then co-concentrated with toluene to provide the title compound (94 mg, 0.173 mmol, 100% yield). Mass spectrum (ESI) 429.2 (M+).

Step C. 7-Isopropyl-2-[4-({8-[4-(trifluoromethyl)pyrimidin-2-yl]-2,8-diazaspiro[4.5]dec-2-yl}carbonyl)phenyl]-1,3-benzoxazole-5-carbonitrile To a solution of 2-[4-(2,8-diazaspiro[4.5]dec-2-ylcarbonyl)phenyl]-7-isopropyl-1,3-benzoxazole-5-carbonitrile (25 mg, 0.046 mmol) in methanol (2 ml) were added potassium carbonate (13 mg, 0.094 mmol) and 2-chloro-4-(trifluoromethyl)pyrimidine (10 μl, 0.083 mmol). The mixture was heated to 50° C. and stirred at this temperature overnight, at which point LC/MS analysis showed a peak at the desired molecular weight. The reaction mixture was purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (17.4 mg, 0.030 mmol, 65.7% yield). Mass spectrum (ESI) 575.2 (M+1).

Example 122

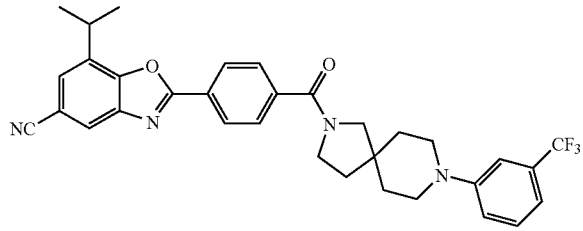

7-Isopropyl-2-[4-({8-[4-(trifluoromethyl)benzyl]-2,8-diazaspiro[4.5]dec-2-yl}carbonyl)phenyl]-1,3-benzoxazole-5-carbonitrile To a solution of 2-[4-(2,8-diazaspiro[4.5]dec-2-ylcarbonyl)phenyl]-7-isopropyl-1,3-benzoxazole-5-carbonitrile (25 mg, 0.046 mmol, EXAMPLE 121, Step B) in dichloromethane (2 ml) were added diisopropylethylamine (20 µl, 0.115 mmol) and 4-(trifluoromethyl)benzyl bromide (17 mg, 0.071 mmol). The mixture was stirred at room temperature overnight, at which point LC/MS analysis showed a peak at the desired molecular weight. The reaction mixture was purified by flash chromatography on a Biotage Horizon, 25S column, eluting with 1 column volume of 100% dichloromethane followed by a gradient of 0 to 100% ethyl acetate in dichloromethane over 10 column volumes to provide the title compound (21.4 mg, 0.036 mmol, 79% yield). Mass spectrum (ESI) 587.3 (M+1).

Intermediate 28

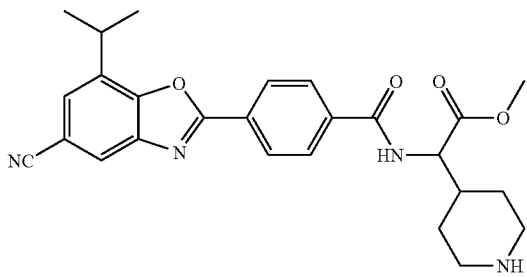

Methyl{[4-(5-cyano-7-isopropyl-1,3-benzoxazol-2-yl)benzoyl]amino}(piperidin-4-yl)acetate Step A. tert-Butyl-4-(1-{[4-(5-cyano-7-isopropyl-1,3-benzoxazol-2-yl)benzoyl]amino}-2-methoxy-2-oxoethyl)piperidine-1-carboxylate At room temperature, a 2-dram vial equipped with a magnetic stirrer was charged with 4-(5-cyano-7-isopropyl-1,3-benzoxazol-2-yl)benzoic acid (INTERMEDIATE 2), 4-(amino-methoxycarbonyl-methyl)-piperidine-1-carboxylic acid tert-butyl ester, bromo-tris-pyrrolidino phosphonium hexafluorophosphate, and dimethylformamide (5 ml). To this mixture was added of N,N-diisopropylethylamine, dropwise. The reaction mixture was allowed to stir at room temperature for 3 d. The residue was purified by flash chromatography using a Biotage SP 1, 40M silica cartridge, eluting with a linear gradient of 20% to 100% hexanes in ethyl acetate over 15 column volumes to provide the title compound. Mass spectrum (ESI) 559.3 (M+1).

Step B. Methyl {[4-(5-cyano-7-isopropyl-1,3-benzoxazol-2-yl)benzoyl]amino}(piperidin-4-yl)acetate To a 40-ml scintillation vial was added tert-butyl-4-(1-{[4-(5-cyano-7-isopropyl-1,3-benzoxazol-2-yl)benzoyl]amino}-2-methoxy-2-oxoethyl)piperidine-1-carboxylate (150 mg, 0.268 mmol) and 2 ml of a TFA-water solution [95:5]. The reaction was stirred for 16 h at room temperature and then poured into 5 g of crushed ice and basified with potassium carbonate. The product was extracted with dichloromethane (4×3 ml), and the combined organics were dried (magnesium sulfate), filtered and concentrated in vacuo to provide the title compound as an off-white solid. The crude product was used without further purification in the next step. Mass spectrum (ESI) 461.57 (M+1). $^1$H NMR (600 MHz, CDCl$_3$): δ 8.27 (d, J=8.4 Hz, 2H), 7.76 (d, J=8.4 Hz, 2H), 7.92 (d, J=1.1 Hz, 1H), 7.57 (s, 1H), 4.6 (d, J=7.1 Hz, 1H), 3.71 (s, 3H), 3.43 (m, 1H), 3.23 (m, 2H), 2.84 (m, 2H), 2.2 (m, 1H), 1.88 (d, J=13.8 Hz, 2H), 1.51 (m, 2H), 1.40 (d, J=6.8, 6H).

Example 123

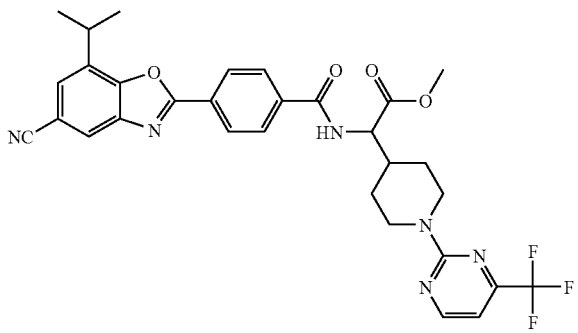

Methyl {[4-(5-cyano-7-isopropyl-1,3-benzoxazol-2-yl)benzoyl]amino}{1-[4-(trifluoromethyl)pyrimidin-2-yl]piperidin-4-yl}acetate The title compound was prepared from methyl{[4-(5-cyano-7-isopropyl-1,3-benzoxazol-2-yl)benzoyl]amino}(piperidin-4-yl)acetate (INTERMEDIATE 27) using the procedure described in EXAMPLE 121. Mass spectrum (ESI) 607.32 (M+1). $^1$H NMR (600 MHz, CDCl$_3$): δ 8.45 (d, J=4.8 Hz, 1H), 8.32 (d, J=8.2 Hz, 2H), 7.96 (d, J=8.2 Hz, 2H), 7.93 (d, J=1.4 Hz, 1H), 7.5 (s, 1H), 6.78 (d, J=8.2 Hz, 1H), 6.71 (d, J=4.8 Hz, 1H), 4.91 (m, 3H), 3.82 (s, 3H), 3.47 (m, 2H), 2.44 (t, J=12.85 Hz, 1H), 2.26 (m, 1H), 1.89 (d, J=13.1 Hz, 1H), 1.76 (d, J=12.3 Hz, 1H), 1.44 (d, J=7, 6H).

Following the procedures described in EXAMPLES 120-122, the compounds listed in Tables 8 and 9 were prepared.

The symbol "X1" on each substituent group shows the point of attachment of the substituent group to the structure at the top of the table.

TABLE 8

| EXAMPLE | R1, R2 | MS (M + 1) |
|---|---|---|
| 124 | | 633.1 |
| 125 | | 601.3 |
| 126 | | 589.1 |
| 127 | | 524.2 |

TABLE 8-continued

| EXAMPLE | R1, R2 | MS (M + 1) |
|---|---|---|
| 128 | | 512.1 |
| 129 | | 465.2 |
| 130 | | 465.2 |

TABLE 9

| EXAMPLE | R | MS (M + 1) |
|---|---|---|
| 131 | | 524.2 |
| 132 | | 493.3 |

TABLE 9-continued

[Structure: benzoxazole with isopropyl, CN, and phenyl-C(=O)NH-R substituents]

| EXAMPLE | R | MS (M+1) |
|---|---|---|
| 133 | [Structure: X₁-CH₂-azetidine-N-pyrimidine-CF₃] | 521.0 |

What is claimed is:

1. A compound having Formula 1a, or a pharmaceutically acceptable salt thereof:

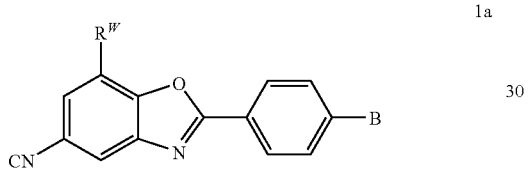

1a wherein $R^W$ is selected from the group consisting of $C_1$-$C_4$alkyl which is optionally substituted with 1-3 F, $C_{2-3}$ alkenyl, —OCH$_3$, —OCF$_3$, —SCH$_3$, —SCF$_3$, cyclopropyl, —C(=O)OC$_{1-3}$alkyl, and phenyl which is optionally substituted with 1-3 substituents independently selected from halogen, CH$_3$, CF$_3$, —OCH$_3$, and —OCF$_3$;

B is selected from the group consisting of:
(a) —C(=O)N(R$^3$)(CR$^4$R$^5$)$_x$(CR$^6$R$^7$)$_y$D$^2$,
(b) —C(=O)N(R$^3$)(CR$^4$R$^5$)$_p$(CR$^6$R$^7$)$_q$D$^3$, and
(c) —C(=O)D$^3$;

R$^3$ is selected from the group consisting of H and CH$_3$;
R$^4$ is selected from the group consisting of H, CH$_3$, —C(=O)OH, and —C(=O)OCH$_3$;
R$^5$ is H;
R$^6$ is H;
R$^7$ is selected from the group consisting of H and phenyl, which is optionally substituted with 1-3 groups independently selected from halogen, CH$_3$, CF$_3$, —OCH$_3$, and —OCF$_3$;
x is 0 or 1;
y is 0;
p is 1;
q is 0 or 1;
D$^2$ is a cyclic group selected from (a) 4-membered and 6-8 membered saturated and partly unsaturated heterocyclic groups, and (b) a spirocyclic group having two rings joined by a spirocyclic linkage through a carbon atom wherein each ring is a 5-7-membered ring, wherein D$^2$ comprises one ring member —N(R$^8$)—, optionally 1-2 ring members independently selected from —O— and —S—, optionally one carbonyl group, and optionally 1-2 double bonds, wherein D$^2$ or a ring of D$^2$ is optionally fused to a phenyl ring or to a $C_5$-$C_7$Cycloalkyl, wherein D$^2$ is connected to the right hand side of the structure represented by Formula I through a carbon atom of D$^2$, wherein D$^2$ is optionally substituted with 1-3 substituents independently selected from halogen, —CN, —NO$_2$, —N(R$^3$)$_2$—, $C_1$-$C_3$alkyl, CF$_3$, —OCH$_3$, phenyl, pyridyl, and —OCF$_3$, and optionally with 1 group $C_1$-$C_5$alkylene-phenyl, wherein phenyl and pyridyl in all uses are optionally substituted with 1-3 substituent groups independently selected from halogen, CH$_3$, CF$_3$, —OCH$_3$, and —OCF$_3$;

D$_3$ is a heterocyclic group selected from (a) a saturated or partly unsaturated 4-8 membered monocyclic heterocyclic group, (b) a saturated or partly unsaturated bicyclic heterocyclic group wherein each ring is a 5-8-membered ring, and (c) a spirocyclic group having two rings joined by a spirocyclic linkage through a carbon atom wherein each ring is a 5-7-membered ring, wherein D$^3$ comprises one N atom which is connected to the right hand side of the structure represented by Formula I, and D$^3$ optionally comprises (a) 1-2 heteroatoms independently selected from O and S, (b) optionally one group —N(R$^8$)—, (c) optionally 1-2 double bonds, and (d) optionally one carbonyl group, wherein D$^3$ or a ring of D$^3$ is optionally fused to a phenyl group, and D$^3$ is optionally substituted with 1-3 substituents independently selected from halogen, —CN, —NO$_2$, —N(R$^3$)$_2$—, $C_1$-$C_3$alkyl, CF$_3$, —OCH$_3$, phenyl, pyridyl, and —OCF$_3$, and optionally with 1 group $C_1$-$C_5$alkylene-phenyl, wherein phenyl and pyridyl in all uses are optionally substituted with 1-3 substituent groups independently selected from halogen, CH$_3$, CF$_3$, —OCH$_3$, and —OCF$_3$;

R$^8$ is selected from the group consisting of $C_1$-$C_9$alkyl, —C(=O)OC$_1$-$C_9$alkyl, —C(=O)C$_1$-$C_9$alkyl, —S(O)$_{1-2}$C$_1$-$C_9$alkyl, —C(=O)N(R$^9$)$_2$, —C$_1$-$C_3$alkylene-C(=O)OC$_1$-$C_6$alkyl, —C$_1$-$C_5$alkylene-OC$_1$-$C_9$alkyl, and one cyclic group D$^4$ bonded to the N to which R$^8$ is connected or to a difunctional linking group L$^4$ which is bonded to the N to which R$^8$ is connected, wherein the $C_1$-$C_9$alkyl and $C_1$-$C_6$alkyl groups in all uses are optionally substituted with 1-9 halogens;

Wherein D$^4$ is selected from the group consisting of (a) phenyl, (b) naphthyl, (c) $C_3$-$C_8$cycloalkyl optionally having 1-2 double bonds, (d) a saturated or partially unsaturated monocyclic or bicyclic 4-10 membered heterocycle having 1-3 heteroatoms independently selected from N, O, and S and optionally one —C(=O)— group, said heterocycle optionally having 1-2 double bonds, and (e) a monocyclic or bicyclic 5-12 membered heteroaromatic group having 1-3 heteroatoms independently selected from N, S, and O and optionally having one —C(=O)— group;

L$^4$ is selected from the group consisting of —C(=O)—, —C(=O)O—, —S(O)$_2$—, —C(=O)N(R$^3$)—, —S(O)$_2$N(R$^3$)—, —C$_1$-C$_7$alkylene-, —C(=O)C$_1$-C$_7$alkylene-, —C(=O)CH=CH—, —CH$_2$C(=O)—, $C_2$-$C_3$alkenylene, —C(=O)C$_1$-C$_7$alkylene-N(R$^3$)—, —C(=O)OC$_1$-C$_7$alkylene-, —S(O)$_2$C$_1$-C$_7$alkylene-, —C(=O)N(R$^3$)C$_1$-C$_7$alkylene-, —S(O)$_2$N(R$^3$)C$_1$-C$_7$alkylene-, —C$_1$-C$_7$alkylene-N(R$^3$)S(O)$_2$—, —C$_1$-C$_7$alkylene-S(O)$_2$N(R$^3$)—, —C$_1$-C$_7$alkylene-N(R$^3$)C(=O)—, and —C$_1$-C$_7$alkylene-C(=O)N(R$^3$)—, wherein —C$_1$-C$_7$alkylene- optionally comprises a double bond between two adjacent carbons and optionally comprises a difunctional group selected from O, S, —S(O)$_2$—, —NR$^3$—, —C(=O)—, —N(R$^3$)C (=O)—, and —N(R$^3$)S(O)$_2$— between two adjacent carbons, wherein D$^4$ is optionally substituted with 1-3 substituents independently selected from halogen, —CN, —NO$_2$, —OH, C$_1$-C$_7$alkyl, C$_2$-C$_7$alkenyl, CF$_3$, —OC$_1$-C$_5$alkyl, —C$_1$-C$_5$alkylene-OC$_1$-C$_5$alkyl, —OCF$_3$, —N(R$^3$)$_2$—, —C(=O)OH, and —C(=O)OC$_1$-C$_7$alkyl, and is optionally substituted with one cyclic group D$^6$ bonded directly to D$^4$ or connected to D$^4$ through a linking group L$^6$, wherein D$^6$ has the same selections as D$^4$, L$^6$ has the same selections as L$^4$, and D$^6$ is optionally substituted with 1-3 substituents independently selected from halogen, —CN, —NO$_2$, —OH, C$_1$-C$_7$alkyl, C$_2$-C$_7$alkenyl, CF$_3$, —OC$_1$-C$_5$alkyl, —C$_1$-C$_5$alkylene-OC$_1$-C$_5$alkyl, —OCF$_3$, —N(R$^3$)$_2$—, —C(=O)OH, —C(=O)OC$_1$-C$_7$alkyl, and optionally one phenoxy, wherein the C$_1$-C$_7$alkyl, C$_2$-C$_7$alkenyl, and —OC$_1$-C$_5$alkyl groups in all uses in substituents on D4 and D6 are optionally substituted with 1-5 halogens; and Each R$^9$ is independently selected from the group consisting of H, C$_1$-C$_7$alkyl, C$_2$-C$_7$alkenyl, and C$_2$-C$_7$alkynyl, wherein said C$_1$-C$_7$alkyl, C$_2$-C$_7$alkenyl, and C$_2$-C$_7$alkynyl are optionally substituted with 1-9 halogens.

2. The compound of claim 1 having Formula Ia, or a pharmaceutically acceptable salt thereof, wherein:

D$^2$ is selected from the group consisting of azetidine, piperidine, morpholine, a saturated 7-membered heterocyclic ring which comprises one —O— and one —N— in the ring, and a spirocyclic group comprising a cyclopentane ring and a piperidine ring joined by a spirocyclic linkage through a commonly shared carbon atom, wherein D$^2$ is connected to the right hand side of the structure of Formula Ia through a carbon atom of D$^2$, wherein said carbon atom of D$^2$ that is connected to the right hand side of Formula Ia is optionally substituted with one group selected from phenyl, pyridyl, and C$_1$-C$_3$alkyl optionally substituted with 1-3F, wherein the phenyl and pyridyl groups are optionally substituted with one group selected from CH$_3$, CF$_3$, —OCH$_3$, —OCF$_3$, and halogen, and D$^2$ is optionally also substituted on another carbon atom of the ring with one substitutent selected from CH$_3$, CF$_3$, —OCH$_3$, —OCF$_3$ and halogen, and the nitrogen atom in the ring of D$^2$ is attached to the group R$^8$.

3. The compound of claim 1 having formula Ia, or a pharmaceutically acceptable salt thereof, wherein:

D$^3$ is selected from the group consisting of (a) a 5-7-membered saturated cyclic amine; (b) a 6-7 membered saturated cyclic diamine; and (c) a 5-6 membered saturated cyclic amine connected by a spirocyclic linkage through a shared carbon atom to a 5-6 membered cyclic ether, a 5-6 membered cycloalkyl, or a second 5-6 membered saturated cyclic amine, wherein one N atom of D$^3$ is connected to the right hand side of the structure of Formula Ia, and the second N atom of D$^3$, if present, is connected to the group R$^8$, wherein D$^3$ is optionally substituted with one substitutent group selected from CH$_3$, CF$_3$, —OCH$_3$, —OCF$_3$, halogen, phenyl, and —(CH$_2$)$_{1-3}$-phenyl, wherein phenyl and the phenyl group of (CH$_2$)$_{1-3}$phenyl are optionally substituted with one group selected from F, Cl, CH$_3$, CF$_3$, —OCH$_3$ and —OCF$_3$.

4. The compound of claim 1 having formula Ia, or a pharmaceutically acceptable salt thereof, wherein:

R$^8$ is selected from the group consisting of C$_1$-C$_8$alkyl, optionally substituted with 1-7F, —C(=O)C$_1$-C$_8$alkyl, —C(=O)OC$_1$-C$_5$alkyl, and a cyclic group D$^4$ which is bonded directly to the N to which R$^8$ is connected or is bonded to a difunctional linking group L$^4$ which is bonded to the N to which R$^8$ is connected;

D$^4$ is selected from the group consisting of pyrimidinyl, pyridyl, phenyl, C$_3$-C$_6$cycloalkyl, naphthyl, and quinolyl, and is optionally substituted with 1-3 groups independently selected from halogen, C$_1$-C$_4$alkyl, C$_2$-C$_5$alkenyl, CF$_3$, —OC$_1$-C$_4$alkyl, —OCF$_3$, —CO$_2$H, —CO$_2$C$_1$-C$_3$alkyl, —N(CH$_3$)$_2$, —NO$_2$, —CN, and optionally one cyclic group D$^6$ which is bonded directly to D$^4$ or is bonded to a difunctional linking group L$^6$ which is bonded to D$^4$; and L$^4$ is selected from the group consisting of —(CH$_2$)$_{1-3}$—, —C(=O)—, —C(=O)(CH$_2$)$_{1-3}$—, —C(=O)CH(C$_2$H$_5$)—, —C(=O)CH=CH—, —C(=O)OCH$_2$—, —C(=O)NHCH$_2$—, —C(=O)(CH$_2$)$_{1-2}$NH—, —CH$_2$C(=O)—, —SO$_2$—, and —S(O)$_2$(CH$_2$)$_3$—.

5. The compound of claim 4, having formula Ia, or a pharmaceutically acceptable salt thereof, wherein:

D$^6$ is selected from the group consisting of piperidinyl, phenyl, cyclopropyl, cyclohexyl, cyclohexenyl, and pyrazolyl, and is optionally substituted with 1-3 substituents independently selected from C$_1$-C$_4$alkyl optionally substituted with 1-3F, —OC$_1$-C$_4$alkyl optionally substituted with 1-3F, halogen, and optionally one phenoxy;

and L$^6$ is optionally C$_2$-C$_3$alkenylene.

6. The compound of claim 1 having Formula Ia, or a pharmaceutically acceptable salt thereof, wherein:

D$^2$ is selected from the group consisting of azetidine, piperidine, morpholine, a saturated 7-membered heterocyclic ring which comprises one —O— and one —N— in the ring, and a spirocyclic group comprising a cyclopentane ring and a piperidine ring joined by a spirocyclic linkage through a commonly shared carbon atom, wherein D$^2$ is connected to the right hand side of the structure of Formula Ia through a carbon atom of D$^2$, wherein said carbon atom of D$^2$ that is connected to the right hand side of Formula Ia is optionally substituted with one group selected from phenyl, pyridyl, and C$_1$-C$_3$alkyl optionally substituted with 1-3F, wherein the phenyl and pyridyl groups are optionally substituted with one group selected from CH$_3$, CF$_3$, —OCH$_3$, —OCF$_3$, and halogen, and D$^2$ is optionally also substituted on another carbon atom of the ring with one substitutent selected from CH$_3$, CF$_3$, —OCH$_3$, —OCF$_3$ and halogen, and the nitrogen atom in the ring of D$^2$ is attached to the group R$^8$;

D$^3$ is selected from the group consisting of (a) a 5-7-membered saturated cyclic amine; (b) a 6-7 membered saturated cyclic diamine; and (c) a 5-6 membered saturated cyclic amine connected by a spirocyclic linkage through a shared carbon atom to a 5-6 membered cyclic ether, a 5-6 membered cycloalkyl, or a second 5-6 membered saturated cyclic amine, wherein one N atom of D$^3$ is connected to the right hand side of the structure of Formula Ia, and the second N atom of D$^3$, if present, is connected to the group R$^8$, wherein D$^3$ is optionally substituted with one substitutent group selected from CH$_3$, CF$_3$, —OCH$_3$, —OCF$_3$, halogen, phenyl, and —(CH$_2$)$_{1-3}$-phenyl, wherein phenyl and the phenyl group of (CH$_2$)$_{1-3}$phenyl are optionally substituted with one group selected from F, Cl, CH$_3$, CF$_3$, —OCH$_3$ and —OCF$_3$;

R$^8$ is selected from the group consisting of C$_1$-C$_8$alkyl, optionally substituted with 1-7F, —C(=O)C$_1$-C$_8$alkyl, —C(=O)OC$_1$-C$_5$alkyl, and a cyclic group D$^4$ which is bonded directly to the N to which R$^8$ is connected or is bonded to a difunctional linking group L$^4$ which is bonded to the N to which R$^8$ is connected;

D$^4$ is selected from the group consisting of pyrimidinyl, pyridyl, phenyl, C$_3$-C$_6$cycloalkyl, naphthyl, and quinolyl, and is optionally substituted with 1-3 groups independently selected from halogen, C$_1$-C$_4$alkyl, C$_2$-C$_5$alkenyl, CF$_3$, —OC$_1$-C$_4$alkyl, —OCF$_3$, —CO$_2$H, —CO$_2$C$_1$-C$_3$alkyl, —N(CH$_3$)$_2$, —NO$_2$, —CN, and optionally one cyclic group D$^6$ which is bonded directly to D$^4$ or is bonded to a difunctional linking group L$^6$ which is bonded to D$^4$;

L$^4$ is selected from the group consisting of —(CH$_2$)$_{1-3}$—, —C(=O)—, —C(=O)(CH$_2$)$_{1-3}$—, —C(=O)CH(C$_2$H$_5$)—, —C(=O)CH=CH—, —C(=O)OCH$_2$—, —C(=O)NHCH$_2$—, —C(=O)(CH$_2$)$_{1-2}$NH—, —CH$_2$C(=O)—, —SO$_2$—, and —S(O)$_2$(CH$_2$)$_3$—;

D$^6$ is selected from the group consisting of piperidinyl, phenyl, cyclopropyl, cyclohexyl, cyclohexenyl, and pyrazolyl, and is optionally substituted with 1-3 substituents independently selected from C$_1$-C$_4$alkyl optionally substituted with 1-3F, —OC$_1$-C$_4$alkyl optionally substituted with 1-3F, halogen, and optionally one phenoxy;

and L$^6$ is optionally C$_2$-C$_3$alkenylene.

7. The compound of claim 1, wherein R$^W$ is isopropyl.

8. The compound of claim 1, which is selected from the group consisting of the following compounds, or a pharmaceutically acceptable salt thereof:

| Ex. | Structures |
|---|---|
| 1 | 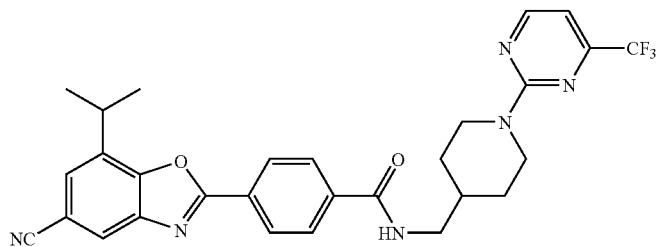 |
| 7 | 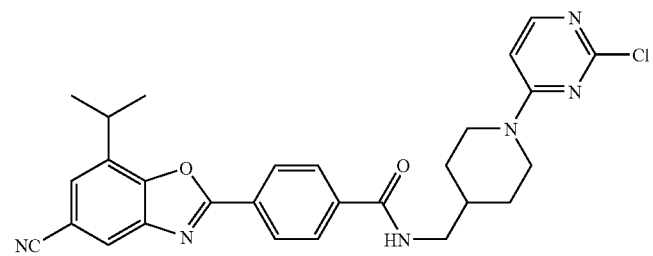 |
| 8 | 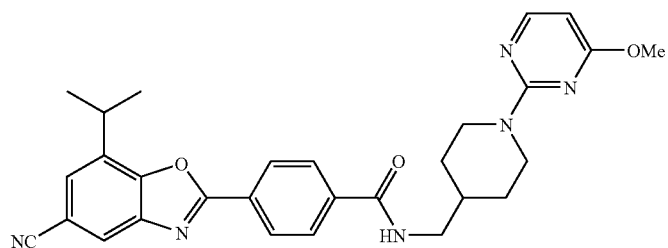 |
| 9 | 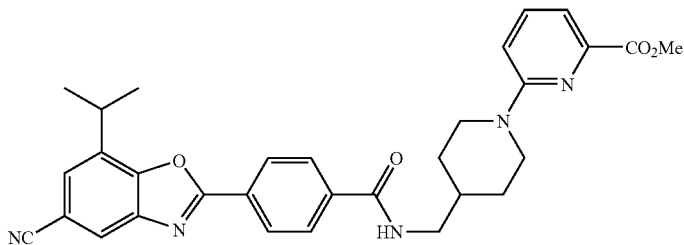 |

| Ex. | Structures |
|---|---|
| 10 | 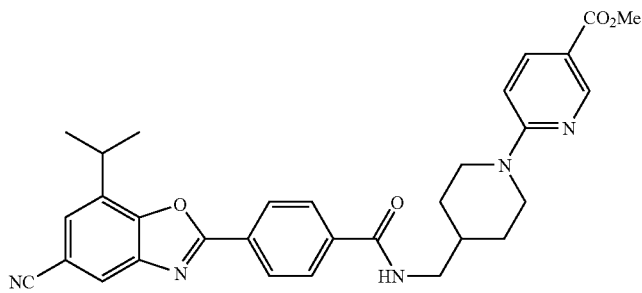 |
| 11 | 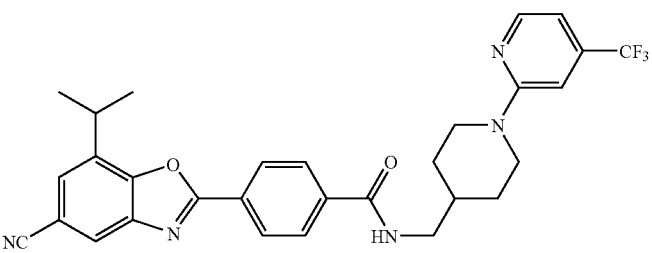 |
| 12 | 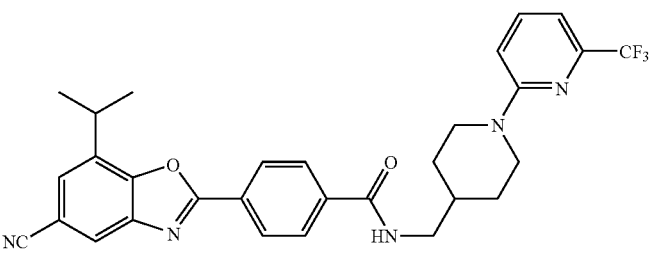 |
| 13 | 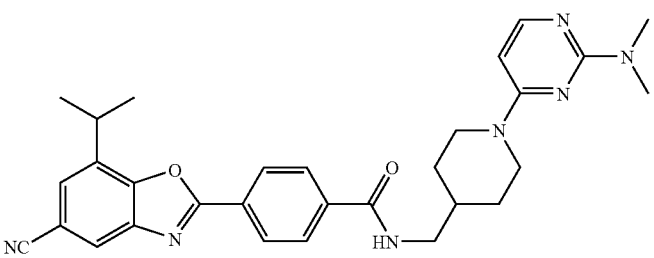 |
| 14 | 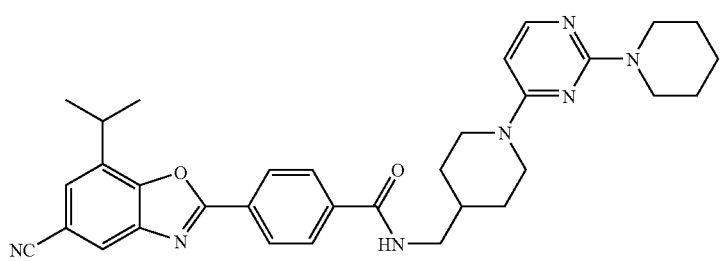 |
| 15 | 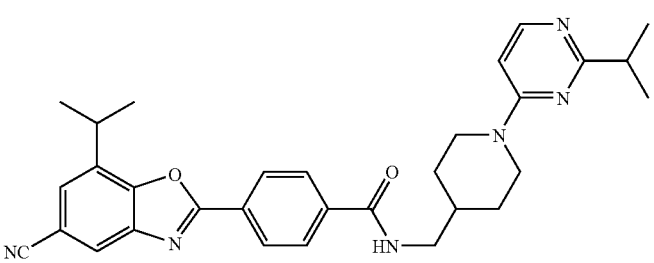 |

-continued
| Ex. | Structures |
|---|---|
| 16 | 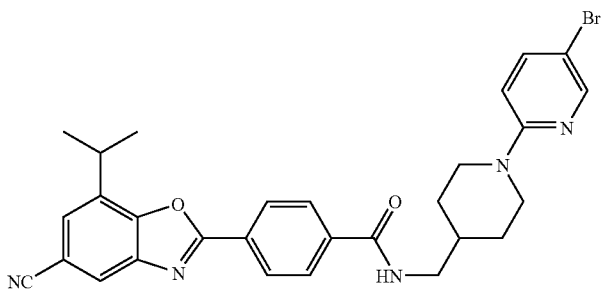 |
| 25 | 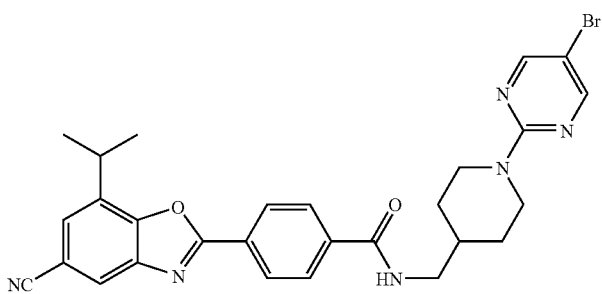 |
| 26 | 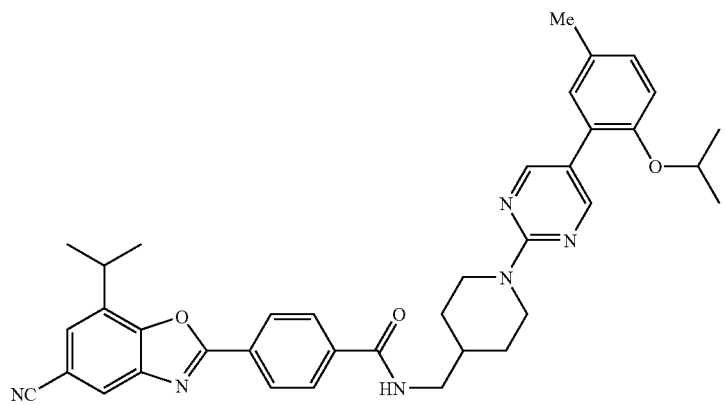 |
| 35 | 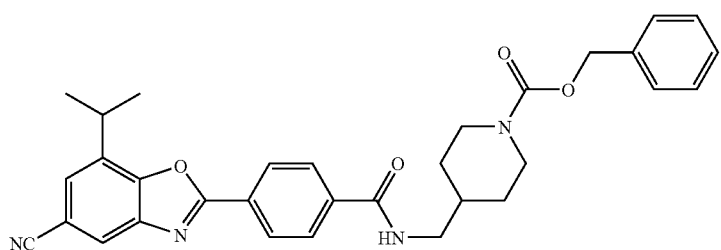 |
| 36 | 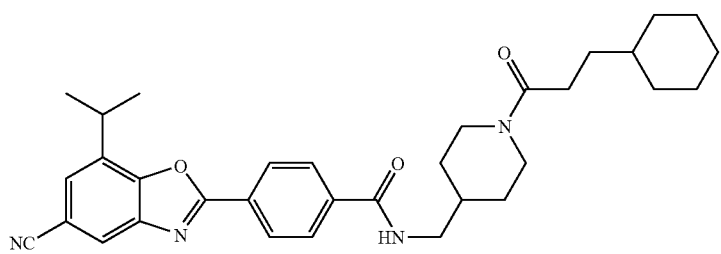 |

| Ex. | Structures |
|---|---|
| 37 | 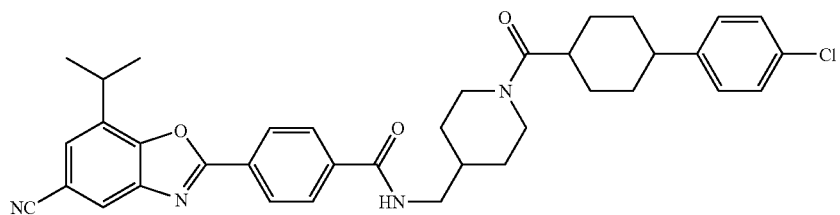 |
| 38 | 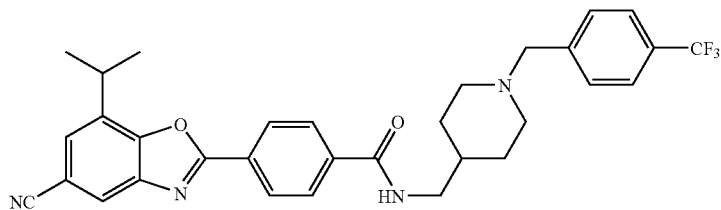 |
| 39 | 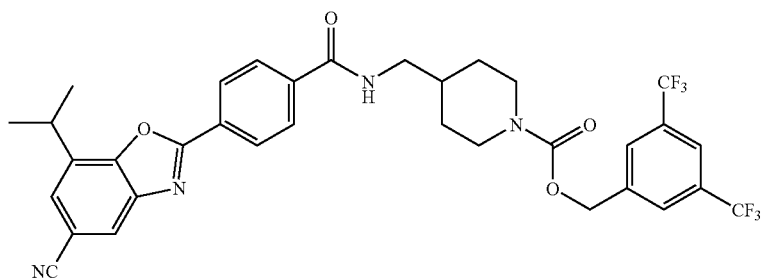 |
| 40 | 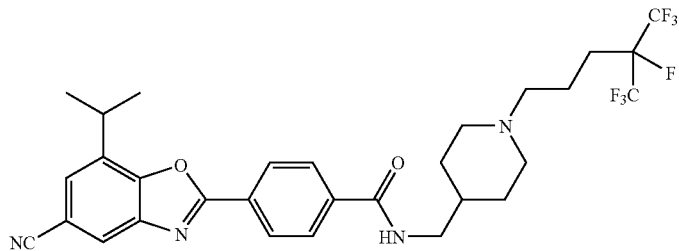 |
| 41 | 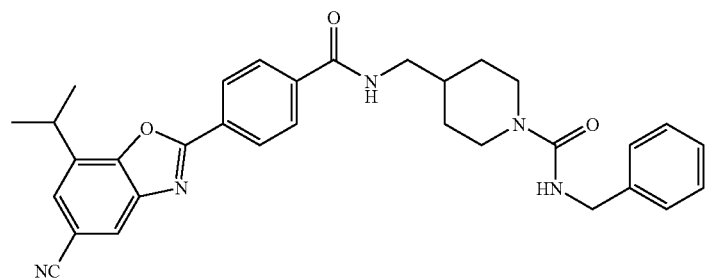 |

| Ex. | Structures |
|---|---|
| 42 | 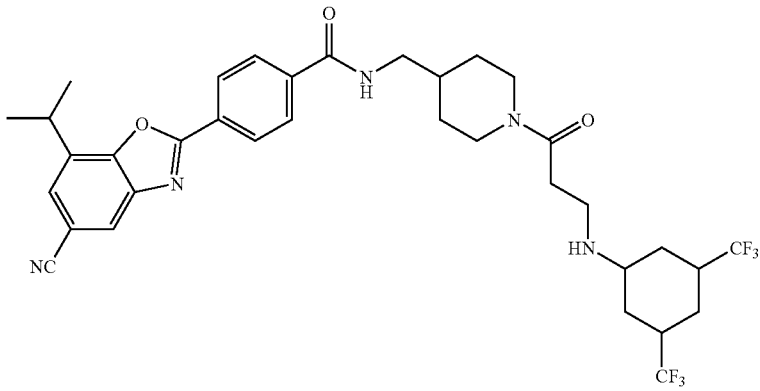 |
| 65 | 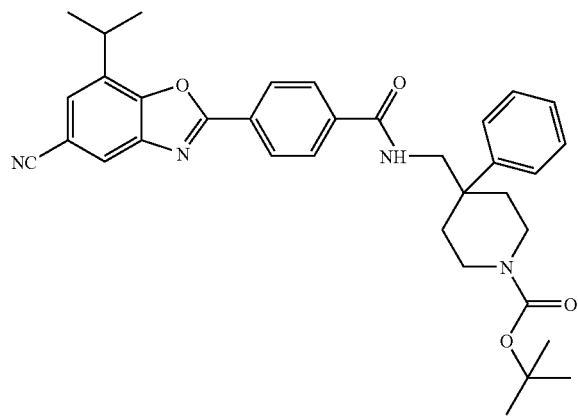 |
| 66 | 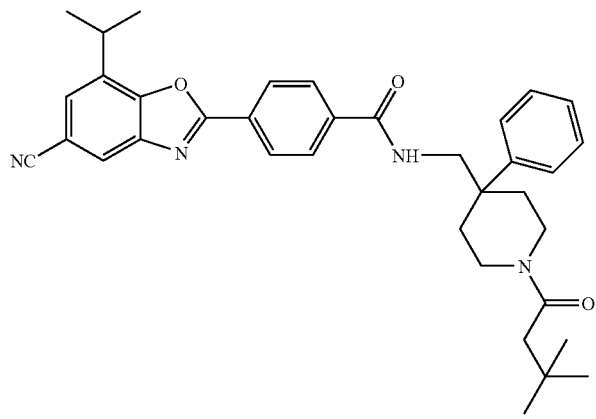 |

-continued
| Ex. | Structures |
|---|---|
| 67 | 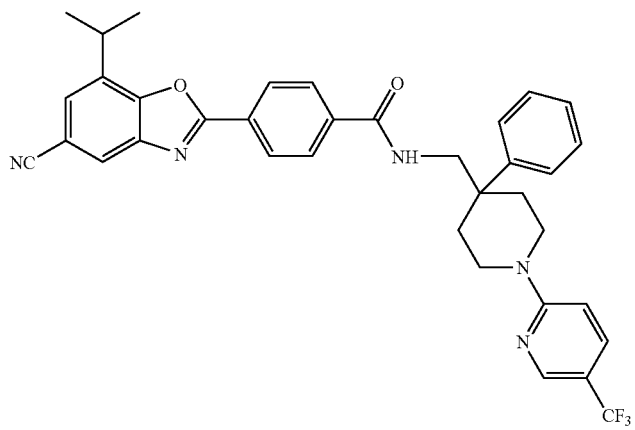 |
| 68 | 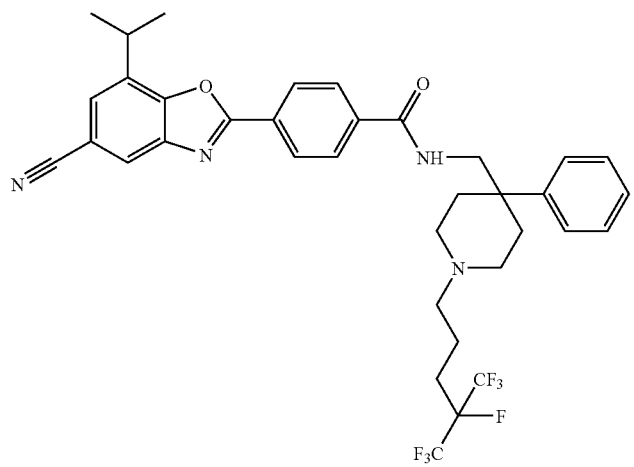 [SMILES: CC(C)c1cc(C#N)cc2nc(-c3ccc(C(=O)NCC4(c5ccccc5)CCN(CCCC(F)(C(F)(F)F)C(F)(F)F)CC4)cc3)oc12] |
| 69 | 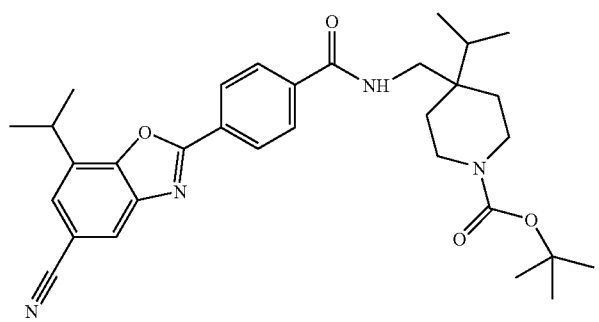 [SMILES: CC(C)c1cc(C#N)cc2nc(-c3ccc(C(=O)NCC4(C(C)C)CCN(C(=O)OC(C)(C)C)CC4)cc3)oc12] |
| 70 | 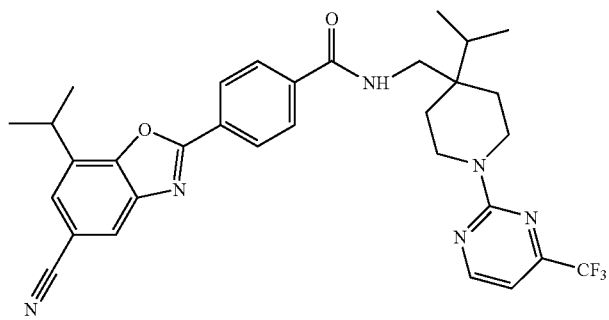 [SMILES: CC(C)c1cc(C#N)cc2nc(-c3ccc(C(=O)NCC4(C(C)C)CCN(c5nccc(C(F)(F)F)n5)CC4)cc3)oc12] |

-continued
| Ex. | Structures |
|---|---|
| 79 | 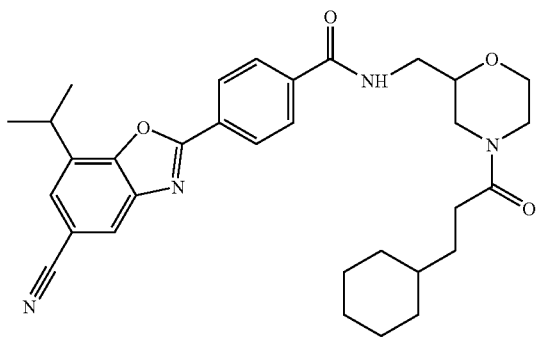 [SMILES: CC(C)c1cc(C#N)cc2nc(-c3ccc(C(=O)NCC4CN(C(=O)CCC5CCCCC5)CCO4)cc3)oc12] |
| 80 | 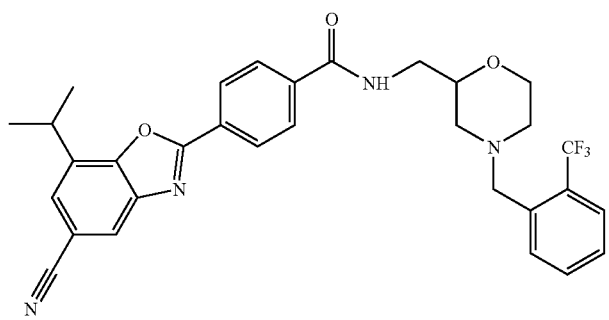 [SMILES: CC(C)c1cc(C#N)cc2nc(-c3ccc(C(=O)NCC4CN(Cc5ccccc5C(F)(F)F)CCO4)cc3)oc12] |
| 81 | 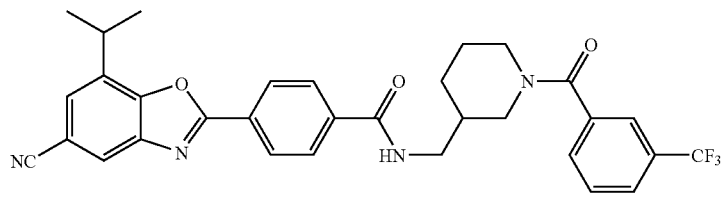 |
| 99 | 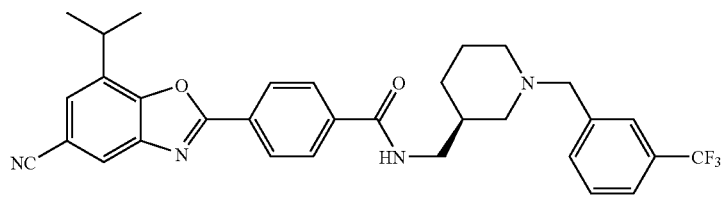 |
| 100 | 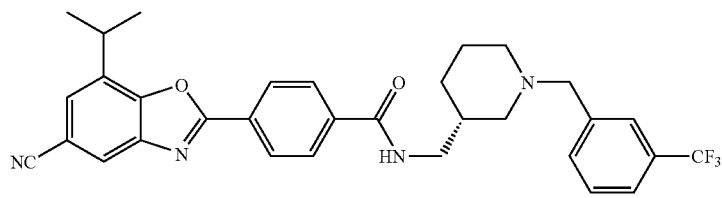 |
| 101 | 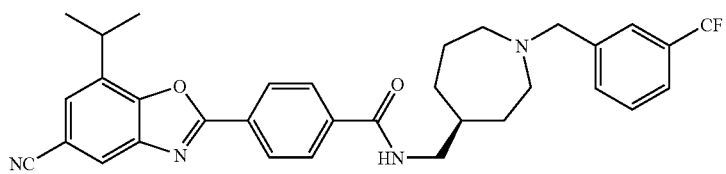 |

| Ex. | Structures |
|---|---|
| 102 | 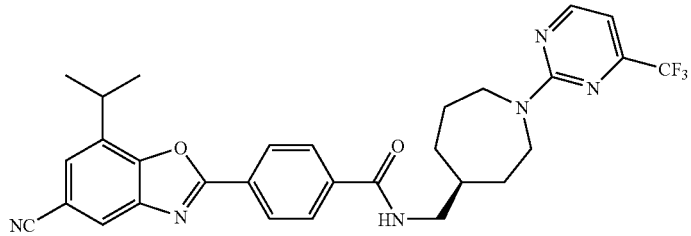 |
| 105 | 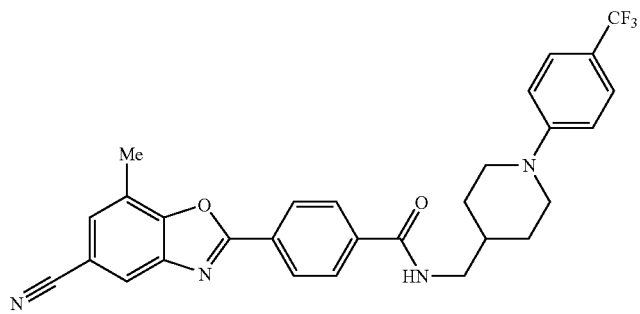 [SMILES: Cc1cc(C#N)cc2nc(-c3ccc(C(=O)NCC4CCN(c5ccc(C(F)(F)F)cc5)CC4)cc3)oc12] |
| 106 | 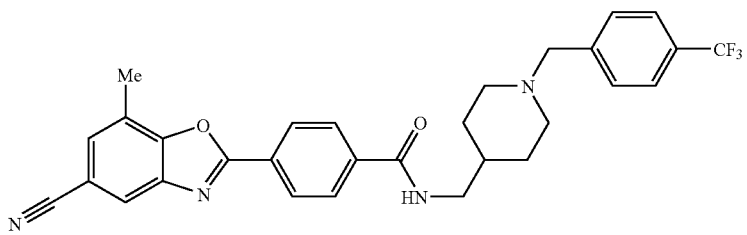 [SMILES: Cc1cc(C#N)cc2nc(-c3ccc(C(=O)NCC4CCN(Cc5ccc(C(F)(F)F)cc5)CC4)cc3)oc12] |
| 107 | 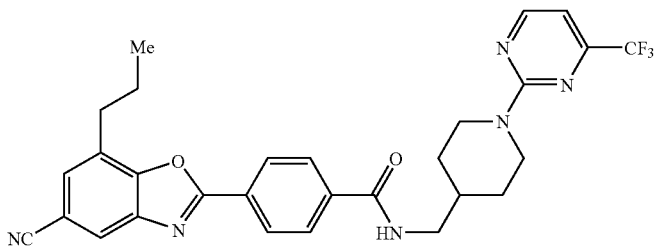 |
| 108 | 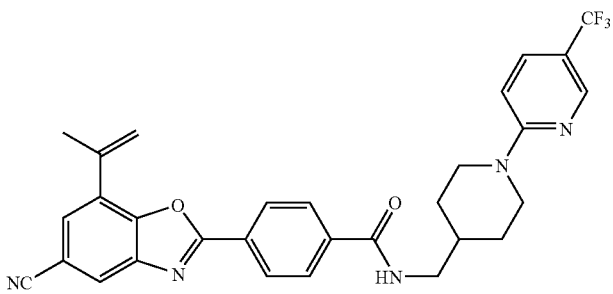 |
| 109 | 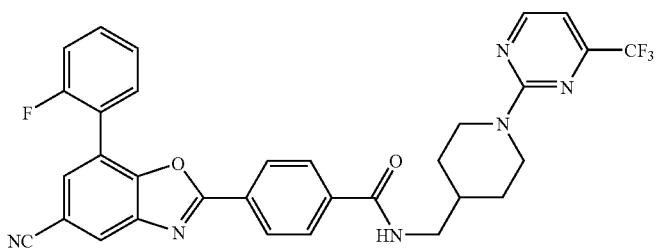 |

| Ex. | Structures |
|---|---|
| 110 | 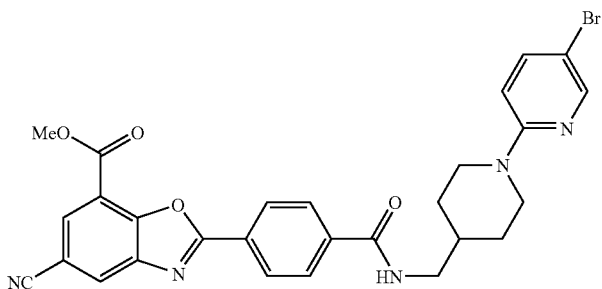 |
| 111 | 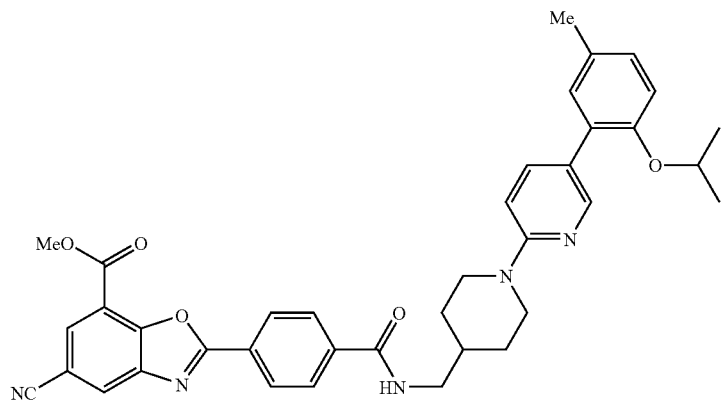 |
| 112 | 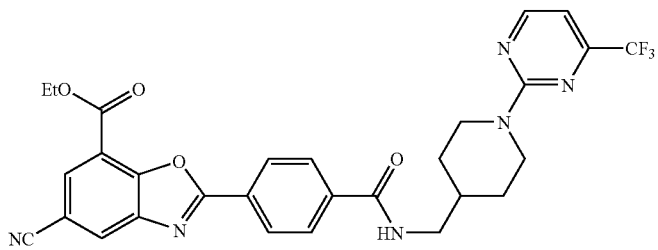 |
| 113 | 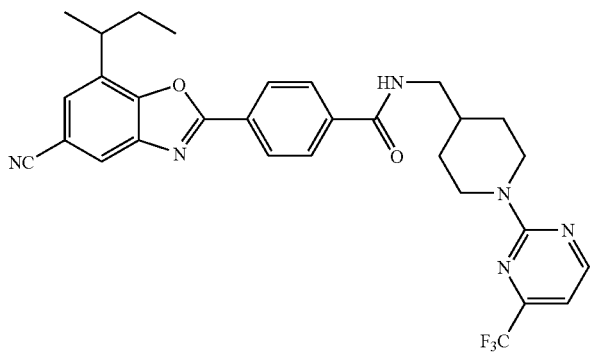 |

| Ex. | Structures |
|---|---|
| 114 | 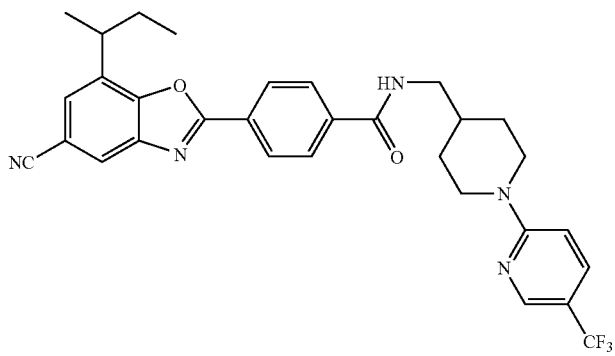 |
| 115 | 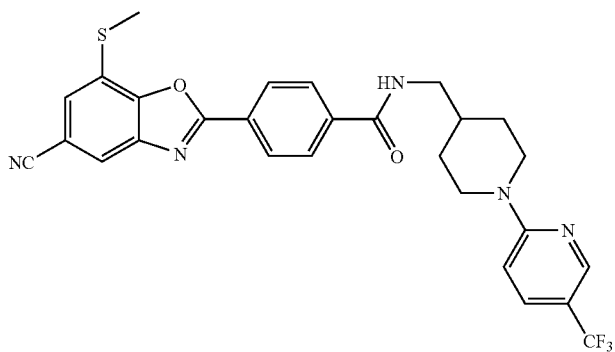 |
| 116 | 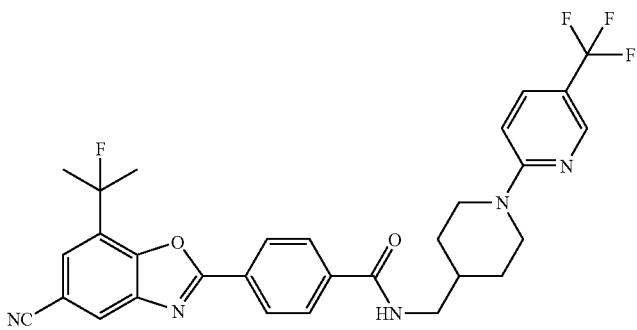 |
| 117 | 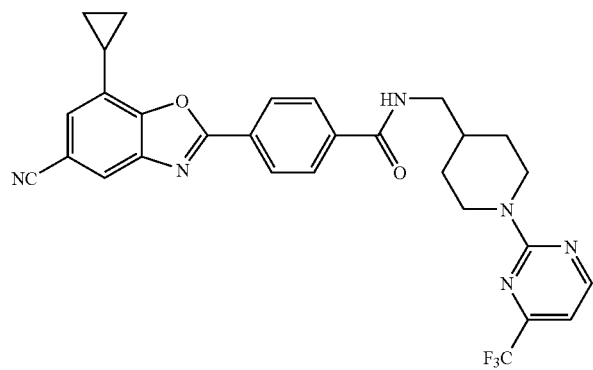 |

| Ex. | Structures |
|---|---|
| 118 | 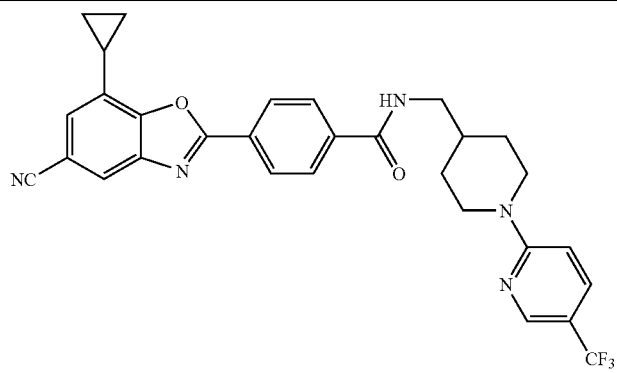 |
| 119 | 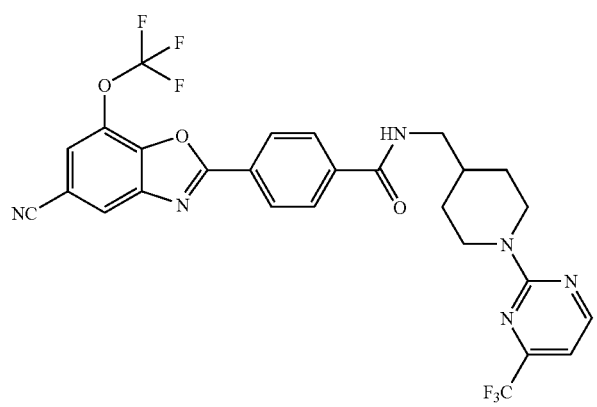 |
| 120 | 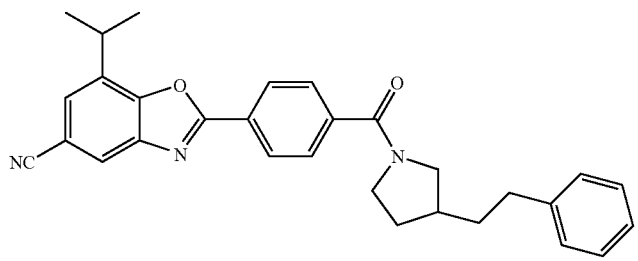 |
| 121 | 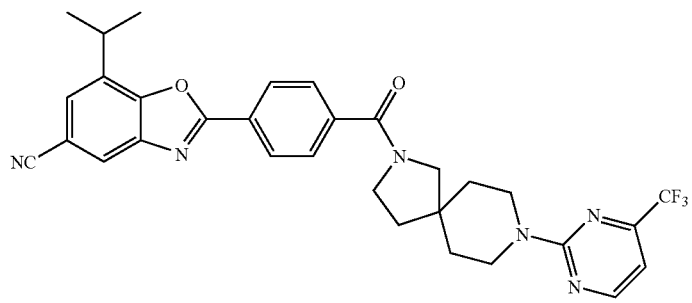 |

| Ex. | Structures |
|---|---|
| 122 | 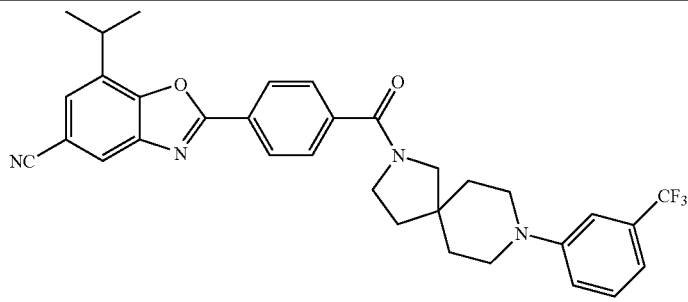 |
| 123 | 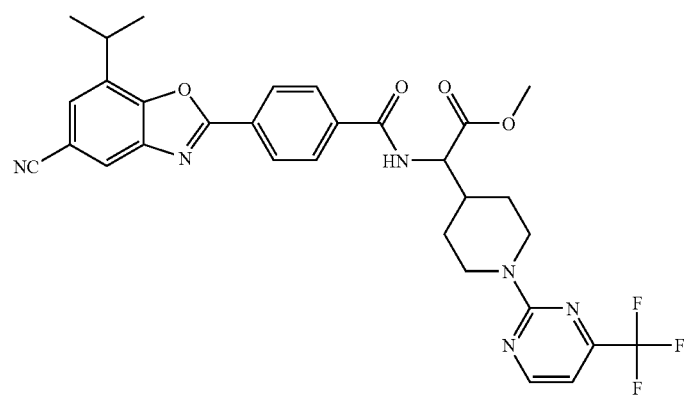 |
9. The compound of claim 1, which is selected from the group consisting of the following compounds, or a pharmaceutically acceptable salt thereof:
(a)
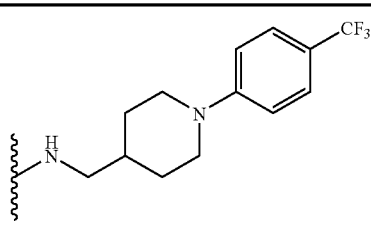
| EXAMPLE | wherein R is |
|---|---|
| 2 | 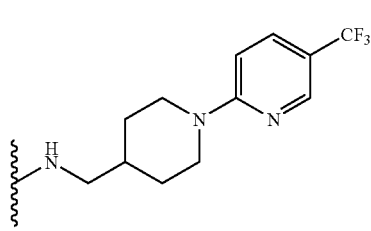 [SMILES: *NCC1CCN(c2ccc(C(F)(F)F)cn2)CC1] |
| 3 | (see below) |
(a)
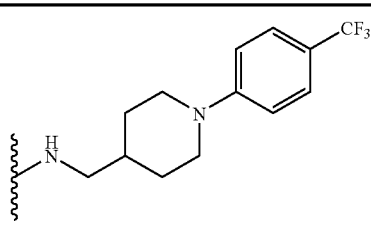
| EXAMPLE | wherein R is |
|---|---|
| 4 | 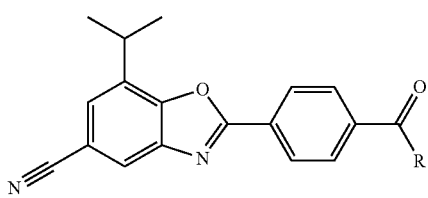 |
| 5 | 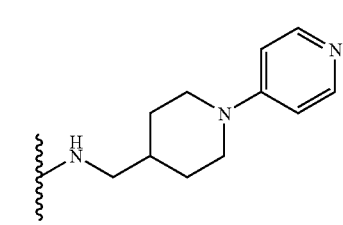 |
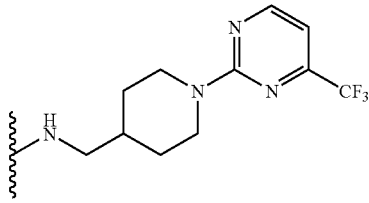 [SMILES: *NCC1CCN(c2nccc(C(F)(F)F)n2)CC1]

115
-continued
(a)
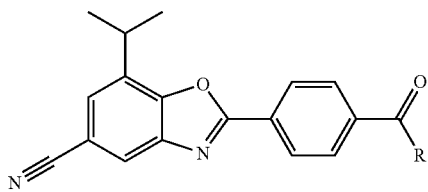
| EXAMPLE | wherein R is |
|---|---|
| 6 | 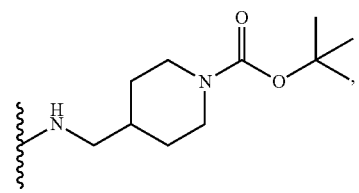 |
(b)
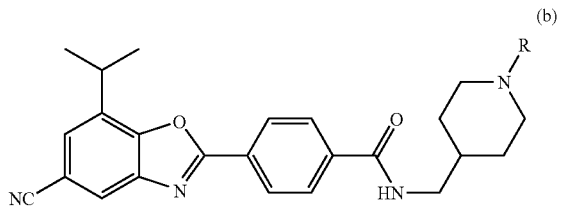
| EXAMPLE | wherein R is |
|---|---|
| 17 | 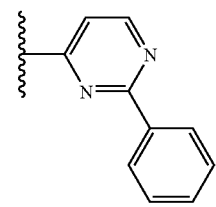 [SMILES: *c1ccnc(-c2ccccc2)n1] |
| 18 | 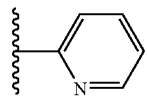 |
| 19 | 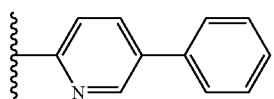 [SMILES: *c1ccc(-c2ccccc2)cn1] |
116
-continued
(b)
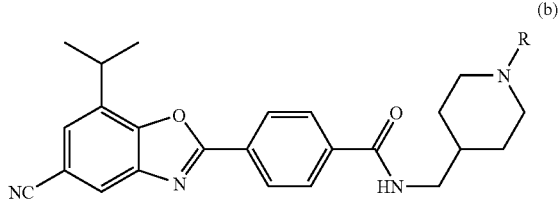
| EXAMPLE | wherein R is |
|---|---|
| 20 | 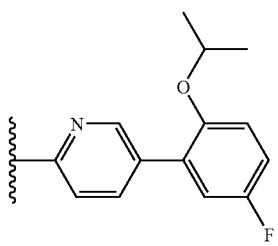 [SMILES: *c1ccc(-c2cc(F)ccc2OC(C)C)cn1] |
| 21 | 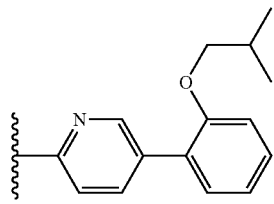 [SMILES: *c1ccc(-c2ccccc2OCC(C)C)cn1] |
| 22 | 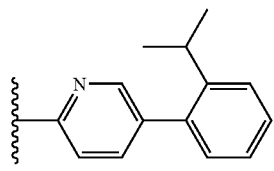 [SMILES: *c1ccc(-c2ccccc2C(C)C)cn1] |
| 23 | 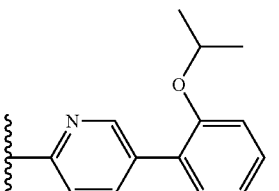 |
| 24 | 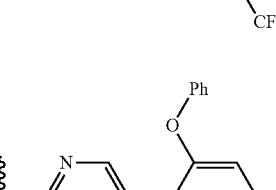 |
|  | 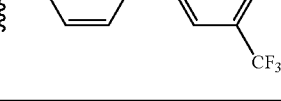 |

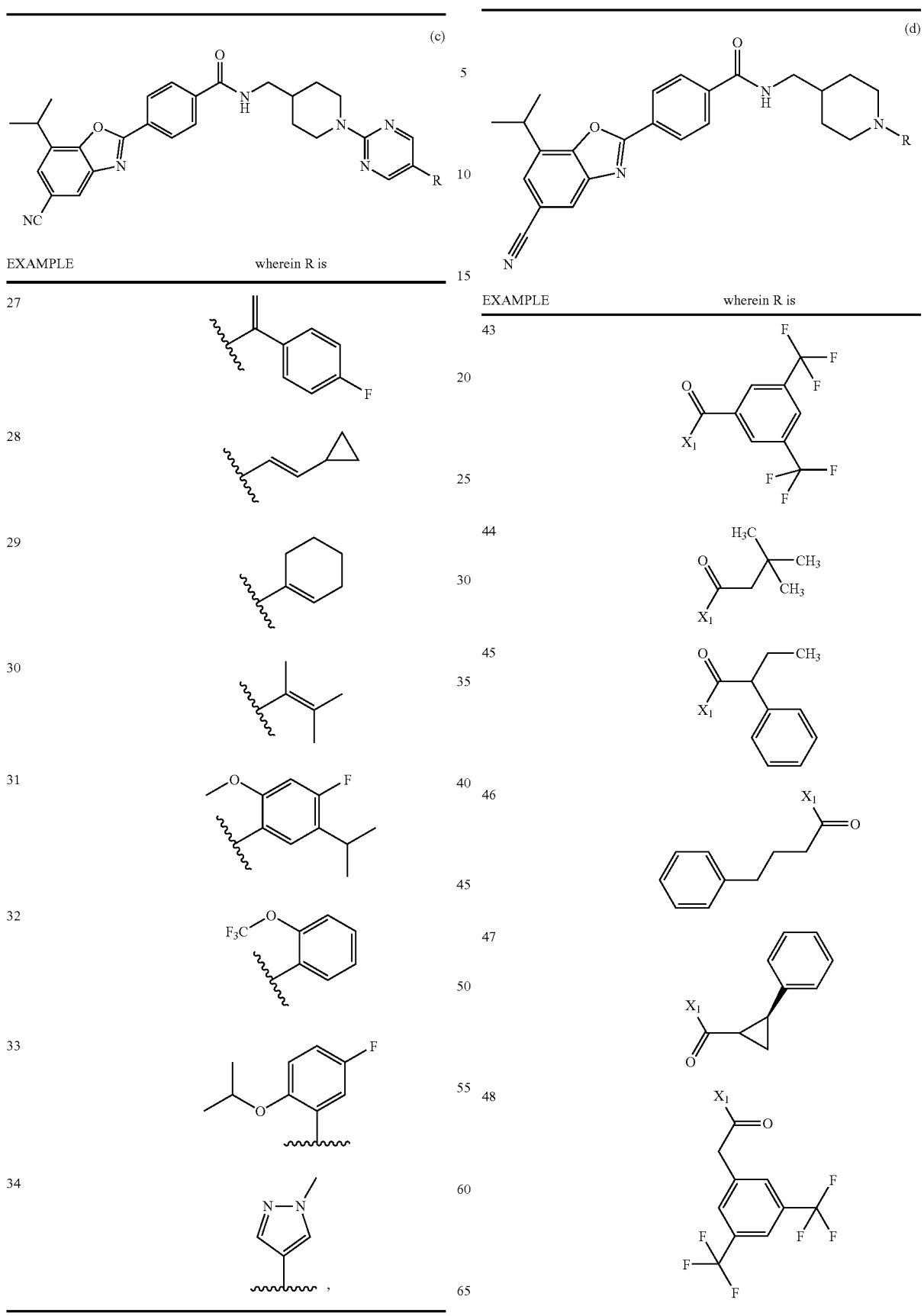

-continued (d)

[Structure: 7-isopropyl-5-cyano-benzoxazole-2-yl-phenyl-C(O)NH-CH2-piperidine-N-R]

| EXAMPLE | wherein R is |
|---|---|
| 49 | X₁–C(O)–CH₂CH₂CH₂–cyclohexyl |
| 50 | X₁–C(O)–(CH₂)₇–CH₃ |
| 51 | X₁–CH₂CH₂CH₂–cyclohexyl |
| 52 | X₁–S(O)₂–[3,5-bis(trifluoromethyl)phenyl] |
| 53 | X₁–S(O)₂–CH₂CH₂CH₂–phenyl |
| 54 | X₁–C(O)–CH=CH–phenyl |
| 55 | X₁–S(O)₂–[4-butylphenyl] |
| 56 | X₁–C(O)–CH₂CH₂–[3,5-bis(trifluoromethyl)phenyl] |

-continued (d)

| EXAMPLE | wherein R is |
|---|---|
| 57 | 2-(trifluoromethyl)benzyl |
| 58 | 3-(trifluoromethyl)benzyl |
| 59 | 3-chlorobenzyl |
| 60 | 3-cyanobenzyl |
| 61 | 6-methoxypyridin-2-yl |
| 62 | 4,6-dimethylpyrimidin-2-yl |

-continued (d)

| EXAMPLE | wherein R is |
|---|---|
| 63 | 4-(trifluoromethyl)cyclohexyl |
| 64 | 3-(trifluoromethyl)cyclohexyl |

(e)

| EXAMPLE | wherein R is |
|---|---|
| 71 | (1-methyl-4-phenylpiperidin-4-yl)methyl |
| 72 | [4-phenyl-1-(4-(trifluoromethyl)pyrimidin-2-yl)piperidin-4-yl]methyl |

-continued
(e)
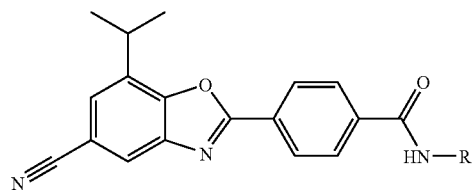
| EXAMPLE | wherein R is |
|---|---|
| 73 | 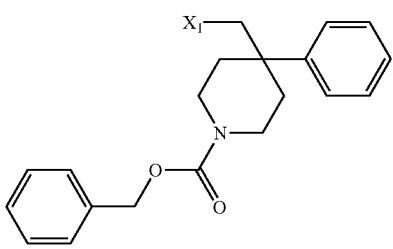 |
| 74 | 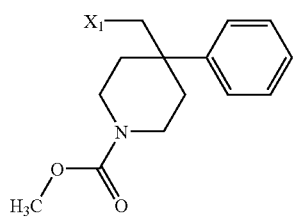 |
| 75 | 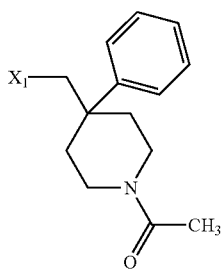 |
| 76 | 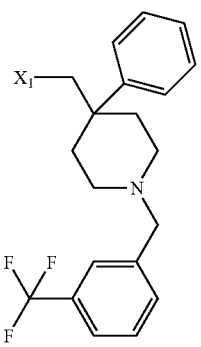 |
-continued
(e)
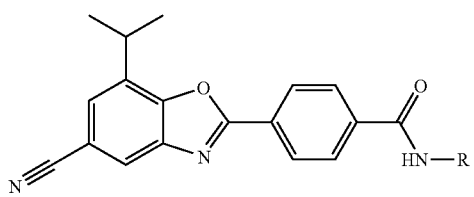
| EXAMPLE | wherein R is |
|---|---|
| 77 | 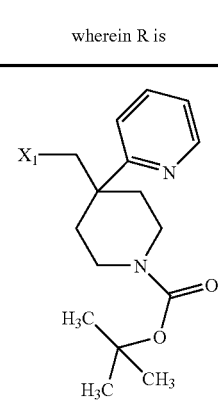 |
| 78 | 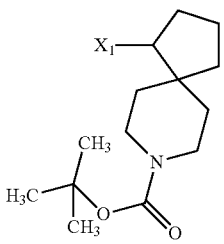 |
(f)
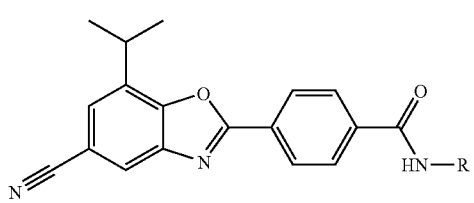
| EXAMPLE | wherein R is |
|---|---|
| 82 | 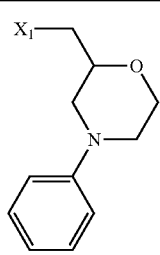 |

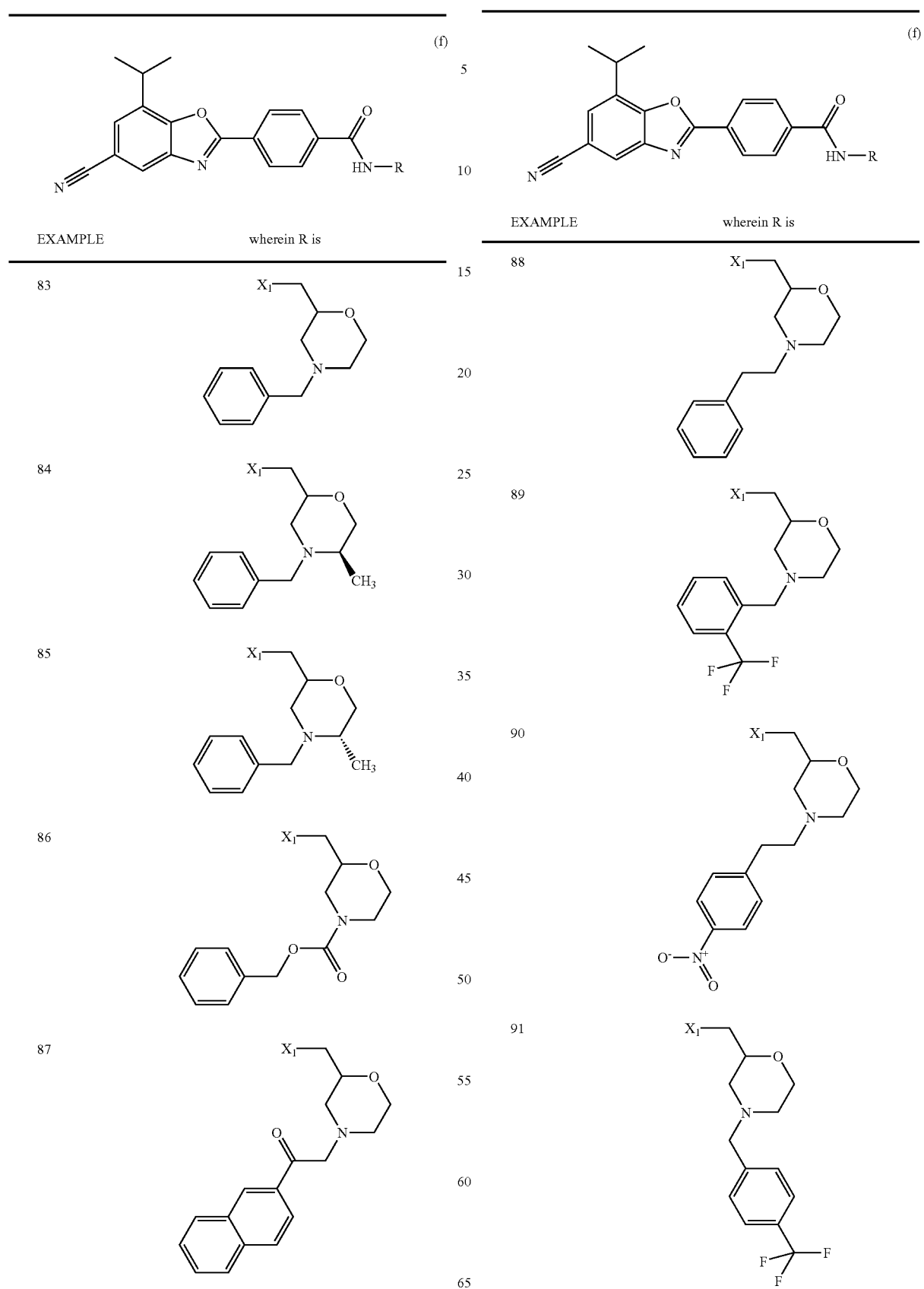

| | (f) |
|---|---|
| 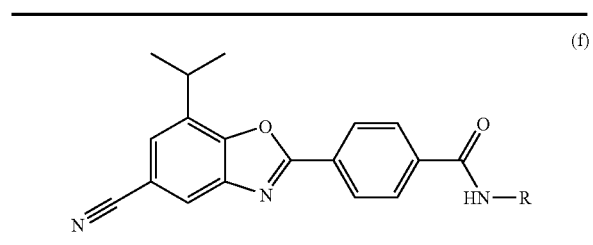 | |
| EXAMPLE | wherein R is |
|---|---|
| 92 | 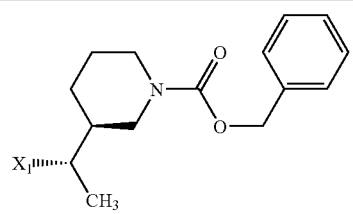 |
| 93 | 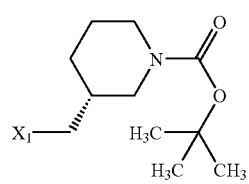 |
| 94 | 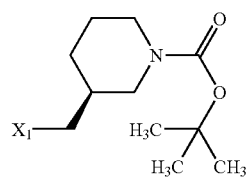 |
| 95 | 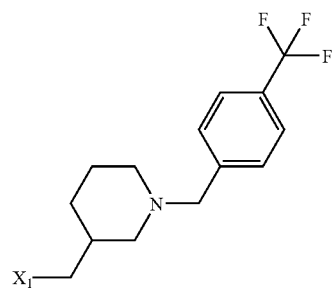 |
| 96 | 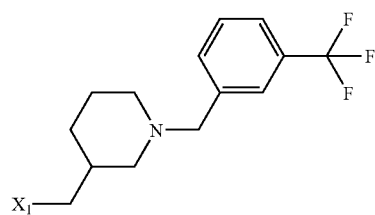 |
| 97 | 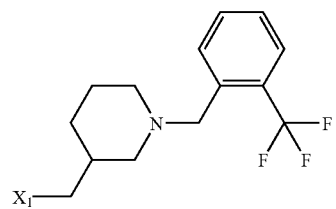 |
| | (f) |
|---|---|
| 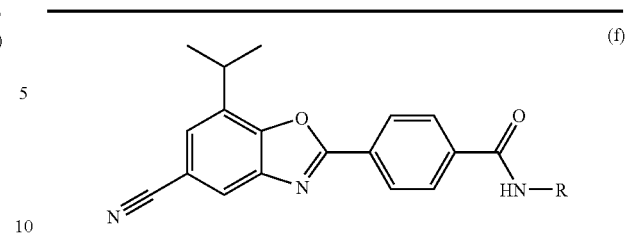 | |
| EXAMPLE | wherein R is |
|---|---|
| 98 | 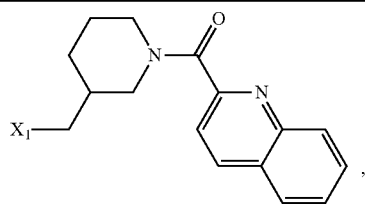 |
| | (g) |
|---|---|
| 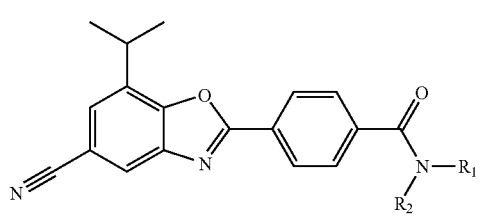 | |
| EXAMPLE | wherein R1, R2, and N form a cyclic amine |
|---|---|
| 124 | 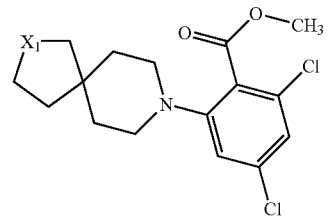 |
| 125 | 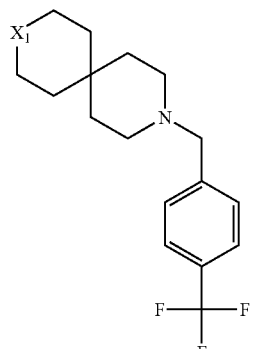 |
| 126 | 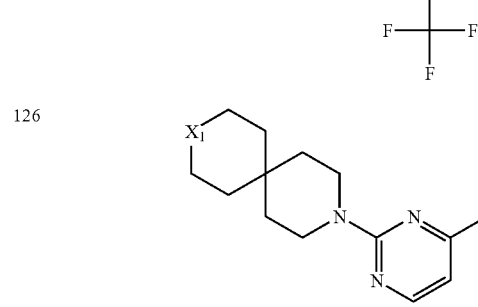 |

| EXAMPLE | (g) wherein R1, R2, and N form a cyclic amine |
|---|---|
| 127 | 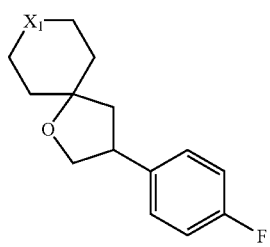 |
| 128 | 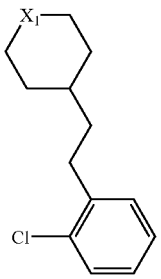 |
| 129 | 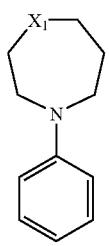 |
| 130 | 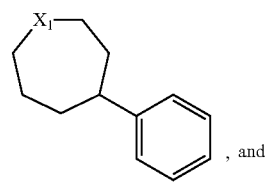, and |

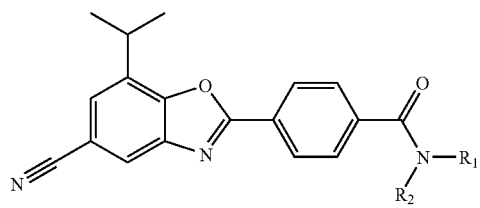

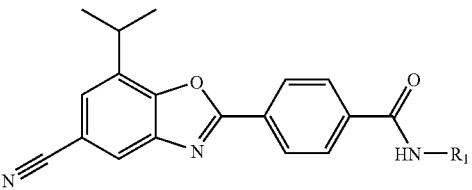

| EXAMPLE | (h) wherein R is |
|---|---|
| 131 | 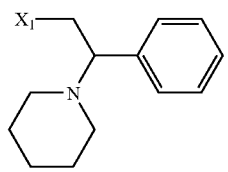 |
| 132 | |
| 133 | | wherein the symbol "X1" represents the point of attachment of the R substituent.

10. A pharmaceutical composition comprising the compound of claim 1 or a pharmaceutically acceptable salt thereof, a pharmaceutically acceptable carrier, and one or more active ingredients selected from the group consisting of:

(i) HMG-CoA reductase inhibitors;
(ii) bile acid sequestrants;
(iii) niacin and related compounds;
(iv) PPARα agonists;
(v) cholesterol absorption inhibitors;
(vi) acyl CoA:cholesterol acyltransferase (ACAT) inhibitors;
(vii) phenolic anti-oxidants;
(viii) microsomal triglyceride transfer protein (MTP)/ApoB secretion inhibitors;
(ix) anti-oxidant vitamins;
(x) thyromimetics;
(xi) LDL (low density lipoprotein) receptor inducers;
(xii) platelet aggregation inhibitors;
(xiii) vitamin B12 (also known as cyanocobalamin);
(xiv) folic acid or a pharmaceutically acceptable salt or ester thereof;
(xv) FXR and LXR ligands;
(xvi) agents that enhance ABCA1 gene expression; and
(xvii) ileal bile acid transporters.

11. A pharmaceutical composition comprising the compound of claim 1, or a pharmaceutically acceptable salt thereof, and a pharmaceutically acceptable carrier.

12. A method of treating atherosclerosis in a patient in need of treatment comprising the administration of a therapeutically effective amount of the compound of claim 1 to said patient, or a pharmaceutically acceptable salt thereof.

13. A method of raising HDL-C in a patient in need of treatment comprising the administration of a therapeutically effective amount of the compound of claim 1 to said patient, or a pharmaceutically acceptable salt thereof.

14. A method of lowering LDL-C in a patient in need of treatment comprising the administration of a therapeutically effective amount of the compound of claim 1 to said patient, or a pharmaceutically acceptable salt thereof.

\* \* \* \* \*

UNITED STATES PATENT AND TRADEMARK OFFICE
CERTIFICATE OF CORRECTION

PATENT NO. : 8,445,480 B2  Page 1 of 1
APPLICATION NO. : 12/664757
DATED : May 21, 2013
INVENTOR(S) : Hunt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 374 days.

Signed and Sealed this
Eighth Day of September, 2015

Michelle K. Lee
*Director of the United States Patent and Trademark Office*